United States Patent [19]
Moore et al.

[11] Patent Number: 6,013,626
[45] Date of Patent: *Jan. 11, 2000

[54] CRYPTOPHYCINS FROM SYNTHESIS

[75] Inventors: Richard E. Moore, Honolulu; Marcus A. Tius, Kailua; Russell A. Barrow; Jian Liang, both of Honolulu, all of Hi.; Thomas H. Corbett, Grosse Point; Frederick A. Valeriote, Shelby Township, both of Mich.; Trimurtulu Golakoti; Thomas K. Hemscheidt, both of Honolulu, Hi.

[73] Assignees: The University of Hawaii, Honolulu, Hi.; Wayne State University, Detroit, Mich.

[ * ] Notice: This patent is subject to a terminal disclaimer.

[21] Appl. No.: 08/400,057

[22] Filed: Mar. 7, 1995

Related U.S. Application Data

[63] Continuation-in-part of application No. PCT/US94/14740, Dec. 21, 1994, which is a continuation-in-part of application No. 08/249,955, May 27, 1994, abandoned, which is a continuation of application No. 08/172,632, Dec. 21, 1993, abandoned.

[51] Int. Cl.[7] .......................... A61K 38/00; A61K 38/12; C07K 5/12
[52] U.S. Cl. .................. 514/9; 514/11; 514/270; 930/270; 530/317
[58] Field of Search .......................... 514/9, 11; 930/270; 530/317

[56] References Cited

U.S. PATENT DOCUMENTS 4,845,086  7/1989  Sesin ........................................ 514/183

OTHER PUBLICATIONS

Smith et al., Cancer Research vol. 54 (Jul. 1994) 3779–84.
Ttimurtulu et al., JACS vol. 116, 4729–37 (1994).
Kubayoshi et al, Chem. Pharm. Bull. vol. 42(16) (Oct. 1994) pp. 2196–98.
Goodman & Gilman, "The Pharmacological Basis of Therapeutics" 6th Ed. (MacMillan Publishing 1980) pp. 1249–1255; 1738–1740.

*Primary Examiner*—Cecilia J. Tsang
*Assistant Examiner*—Bennett Celsa
*Attorney, Agent, or Firm*—Gray Cary Ware & Freidenrich LLP; Stephen E. Reiter; Stanley H. Kim

[57] ABSTRACT

A cryptophycin compound is provided having the structure:

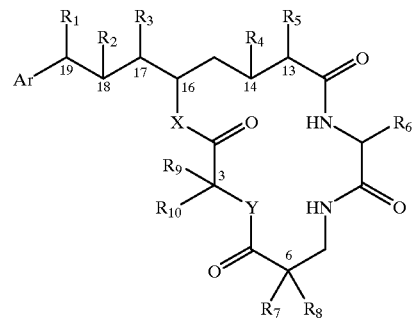

Further provided are methods of producing cryptophycins by total synthesis and methods of using cryptophycins in pharmaceuticals. It is a further object of this invention to use cryptophycins to inhibit the proliferation of mammalian cells. Moreover, methods of using cryptophycins to treat neoplasia is also provided.

25 Claims, 10 Drawing Sheets

Scheme 1

Scheme 2

Scheme 3

$^a$LiOH, acetone, 25°C, 95%; $^b$FDPP, DIEA, DMF, 25°C, 65%; $^c$CH$_3$CN, 50% aq HF (95/5), 25°C, 95%.

Scheme 4

[a](Boc)₂O, Et₃N, CH₃OH, 25°C, 93%; [b]RuCl₃, NaIO₄, CCl₄, CH₃CN, H₂O, 25°C, 66%; [c]DMAP, DCC, CH₂Cl₂, 0°C-25°C, 75%; [d]THF, morpholine, Pd(PPh₃)₄, 25°C, 95%.

Scheme 5

[a] DCC, DMAP, CH$_2$Cl$_2$, 0°C–25°C, 84%; [b] Zn, THF, CH$_3$CO$_2$H, sonicate, 25°C; [c] CF$_3$CO$_2$H, neat, 25°C, 91% (two steps); [d] FDPP, DIEA, DMF, 25°C, 61%; [e] m-CPBA, CH$_2$Cl$_2$, 0°C–25°C, 48%; [f] HCl, DME H$_2$O), 25°C, 95%.

CRYPTOPHYCINS FROM SYNTHESIS

RELATED APPLICATIONS

This is a continuation-in-part of International Application No. PCT/US94/14740, filed Dec. 21, 1994, which is a continuation-in-part of U.S. Application No. 08/249,955, filed May 27, 1994, now abandoned, which is a continuation of U.S. Application No. 08/172,632, filed Dec. 21, 1993, now abandoned. These patent applications are hereby incorporated by reference.

This invention was made in part with U.S. Government support under Grant Nos. CA/12623 and CA53001 from The National Cancer Institute, Department of Health and Human Services. Accordingly, the U.S. Government may have certain rights in this invention.

BACKGROUND OF THE INVENTION

Neoplastic diseases, characterized by the proliferation of cells not subject to the normal control of cell growth, are a major cause of death in humans. Clinical experience in cancer chemotherapy has demonstrated that new and more effective drugs are desirable to treat these diseases. Such clinical experience has also demonstrated that drugs which disrupt the microtubule system of the cytoskeleton can be effective in inhibiting the proliferation of neoplastic cells.

The microtubule system of eucaryotic cells is a major component of the cytoskeleton and is in a dynamic state of assembly and disassembly; that is, heterodimers of tubulin are polymerized and form microtubule. Microtubules play a key role in the regulation of cell architecture, metabolism, and division. The dynamic state of Microtubule is critical to their normal function. With respect to cell division, tubulin is polymerized into Microtubule that form the mitotic spindle. The Microtubule are then depolymerized when the mitotic spindle's use has been fulfilled. Accordingly, agents which disrupt the polymerization or depolymerization of Microtubule, and thereby inhibit mitosis, comprise some of the most effective cancer chemotherapeutic agents in clinical use.

Such anti-mitotic agents or poisons may be classified into three groups on the basis of their molecular mechanism of action. The first group consists of agents, including colchicine and colcemid, which inhibit the formation of Microtubule by sequestering tubulin. The second group consist of agents, including vinblastine and vincristine, which induce the formation of paracrystalline aggregates of tubulin. Vinblastine and vincristine are well known anticancer drugs: their action of disrupting mitotic spindle Microtubule preferentially inhibits hyperproliferative cells. The third group consists of agents, including taxol, which promotes the polymerization of tubulin and thus stabilizes Microtubule.

However, merely having activity as an antimitotic poison does not guarantee efficacy against a tumor cell, and certainly not a tumor cell which exhibits a drug-resistant phenotype. Vinca alkaloids such as vinblastine and vincristine are effective against neoplastic cells and tumors, yet they lack activity against some drug-resistant tumors and cells. One basis for a neoplastic cell displaying drug resistance (DR) or multiple-drug resistance (MDR) is through the over-expression of P-glycoprotein. Compounds which are poor substrates for transport of P-glycoprotein should be useful in circumventing such a MDR phenotype.

Accordingly, the exhibition of the DR or MDR phenotype by many tumor cells and the clinically proven mode of action of anti-microtubule agents against neoplastic cells necessitates the development of anti-microtubule agents cytotoxic to non-drug resistant neoplastic cells as well as cytotoxic to neoplastic cells with a drug resistant phenotype.

With respect to methods of producing cryptophycins, no method for total synthesis of cryptophycins exists. Cryptophycin compounds are presently produced via isolation from blue-green alga or are semi-synthetic variations of such naturally produced compounds. The lack of a total synthetic method necessarily makes it difficult to produce stereospecific cryptophycins which can maximize activity and increase the stability of the compound. For example, research has shown that cryptophycins with an intact macrocyclic ring are more active. Accordingly, a total synthetic method which could produce cryptophycins with a macrocyclic ring that is more stable than naturally derived cryptophycins would be desirable. The present invention solves these problems.

BACKGROUND ART

Selected cryptophycin compounds, dioxandiazacyclohexadecenetetrones isolated or semi-synthesized from isolates from the blue-green algae (cyanobacteria) of the genus Nostoc, were previously characterized as antifungal agents with activity toward filamentous fungi, specifically the Aspergillus, Penicillium and Phoma species thereof; however, their mechanism of action was unknown. Five-cryptophycin compounds, herein designated Cryptophycins 1, 3, 5, 13 and 15, were disclosed in U.S. Pat. Nos. 4,946,835, 4,845,085, 4,845,086, and 4,868,208, such compounds either having been isolated from a strain of Nostoc sp. designated MB 5357 or having been synthesized from such an isolated compound. These issued patents are hereby incorporated by reference.

SUMMARY OF THE INVENTION

The present invention provides novel cryptophycin compounds having the following structure:

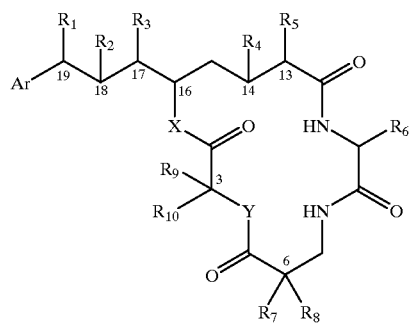

wherein

Ar is phenyl or any simple unsubstituted or substituted aromatic or heteroaromatic group;

$R_1$ is a halogen, SH, amino, monoalkylamino, dialkylamino, trialkylammonium, alkylthio, dialkylsufonium, sulfate, or phosphate;

$R_2$ is OH or SH; or $R_1$ and $R_2$ may be taken together to form an epoxide ring, an aziridene ring, an episulfide ring, a sulfate ring or a monoalkylphosphate ring; or $R_1$ and $R_2$ may be taken together to form a second bond between $C_{18}$ and $C_{19}$;

$R_3$ is a lower alkyl group;

$R_4$ is H;

$R_5$ is H;

$R_4$ and $R_5$ may be taken together to form a second bond between $C_{13}$ and $C_{14}$;

$R_6$ is a benzyl, hydroxybenzyl, alkoxybenzyl, halohydroxybenzyl, dihalohydroxybenzyl, haloalkoxybenzyl, or dihaloalkoxybenzyl group;

$R_7$ is H or a lower alkyl group;

$R_8$ is H or a lower alkyl group;

$R_9$ is H or a lower alkyl group;

$R_{10}$ is H or a lower alkyl group;

X is O, NH or alkylamino; and

Y is O, NH or alkylamino. The present invention further provides total synthetic methods for producing cryptophycins. The present invention also provides for the use of cryptophycins in pharmaceuticals. It is a further object of this invention to use cryptophycins to inhibit the proliferation of mammalian cells. In addition, the present invention provides methods of using cryptophycins to treat neoplasia.

DETAILED DESCRIPTION OF THE INVENTION

Figure 1:
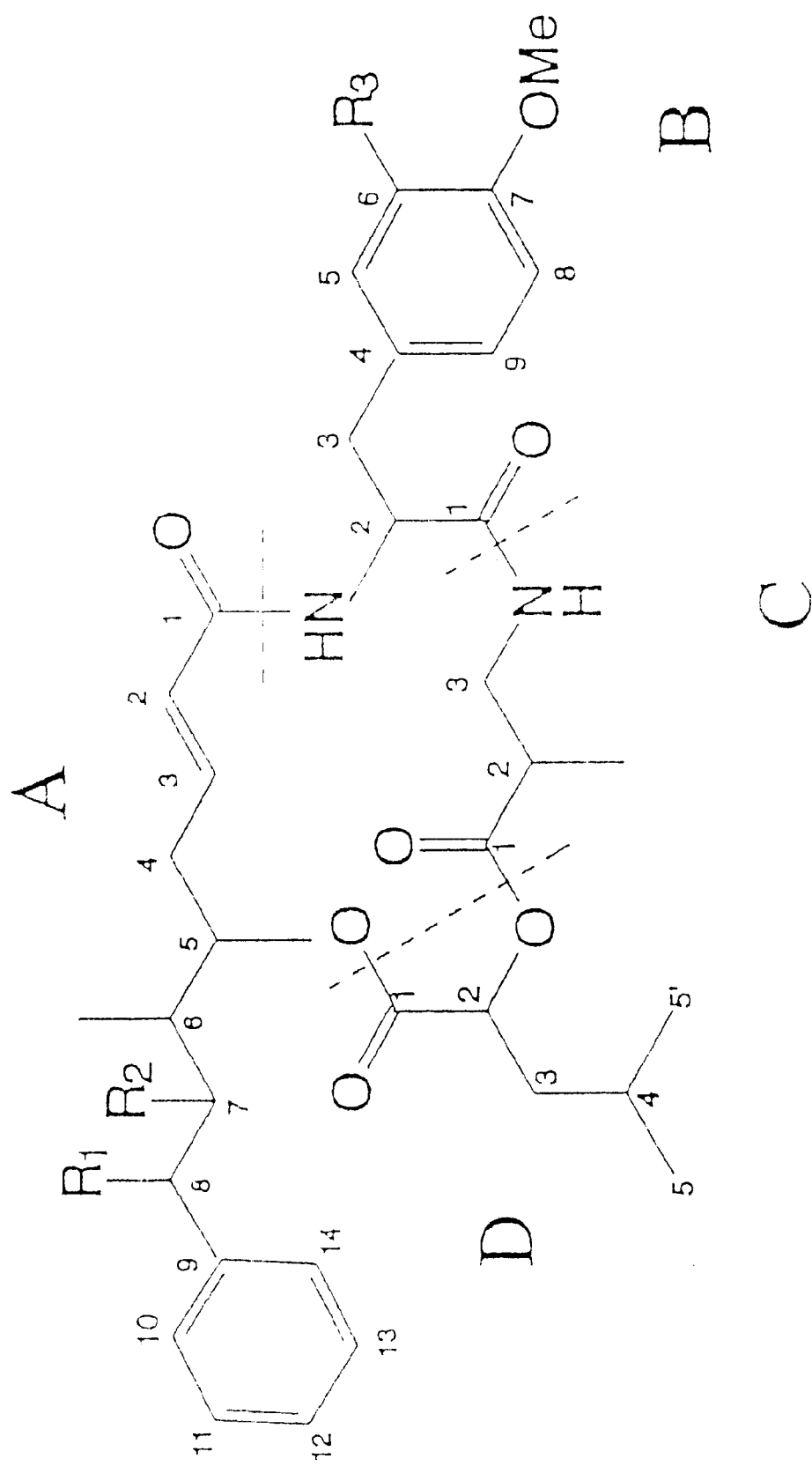
FIG. 1 provides a general structure of selected cryptophycin compounds of the present invention and a numbering system for the hydroxy acid units A and D and two amino acid units B and C in selected embodiments.

The present invention provides novel cryptophycin compounds having the following structure:

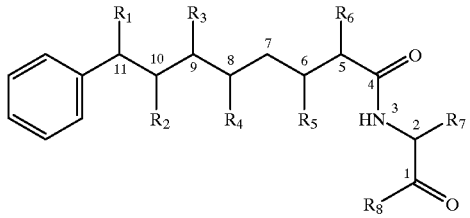

Wherein $R_1$ is H, OH, a halogen, O of a ketone group, $NH_2$, SH, a lower alkoxyl groups or a lower alkyl group;

$R_2$ is H, OH, O of a ketone group, $NH_2$, SH, a lower alkoxyl group or a lower alkyl group; or $R_1$ and $R_2$ may be taken together to form an epoxide ring, an aziridene ring, a sulfide ring or a second bond between $C_{10}$ and $C_{11}$; or $R_1$ and $R_4$ may be taken together to form a tetrahydrofuran ring;

$R_3$ is H or a lower alkyl group;

$R_4$ is OH, a lower alkanoyloxy group or a lower α-hydroxy alkanoyloxy group;

$R_5$ is H or an OH group;

$R_6$ is H; or $R_5$ and $R_6$ may be taken together to form a second bond between $C_5$ and $C_6$;

$R_7$ is a benzyl, hydroxybenzyl, methoxybenzyl, halohydroxybenzyl, dihalohydroxybenzyl, halomethoxybenzyl, or dihalomethoxybenzyl group;

$R_8$ is OH, a lower β-amino acid wherein $C_1$ is bonded to N of the β-amino acid, or an esterified lower β-amino acid wherein $C_1$ is bonded to N of the esterified lower β-amino acid group;

$R_4$ and $R_8$ may be taken together to form a didepsipeptide group consisting of a lower β-amino acid bonded to a lower α-hydroxy alkanoic acid; and $R_5$ and $R_8$ may be taken together to form a didepsipeptide group consisting of a lower β-amino acid bonded to a lower α-hydroxy alkanoic acid; and with the following provisos;

$R_1$ H, a lower alkyl group, or a lower alkoxyl group only if $R_2$ is OH, O of a ketone group, $NH_2$, SH;

$R_2$ is H, a lower alkyl group, or a lower alkoxyl group only if $R_1$ is OH, O of a ketone group, $NH_2$, SH;

when $R_1$ is OH, $R_2$ is OH, $R_3$ is methyl, $R_5$ and $R_6$ are taken together to form a second bond between $C_5$ and $C_6$, $R_4$ and $R_8$ are taken together to form the didepsipeptide group with the structure X:

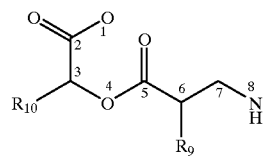

wherein $O_1$ of X corresponds to $R_4$, $N_8$ of X corresponds to $R_8$, $R_9$ is methyl, and $R_{10}$ is isobutyl, $R_7$ is not 3-chloro-4-methoxybenzyl;

when $R_1$ and $R_2$ are taken together to form an epoxide ring, $R_3$ is methyl, $R_5$ and $R_6$ are taken together to form a second bond between $C_5$ and $C_6$, $R_4$ and $R_8$ are taken together to form a didepsipeptide with the structure X, $R_9$ is methyl, and $R_{10}$ is isobutyl, $R_7$ is not 3-chloro-4-methoxybenzyl;

when $R_1$ and $R_2$ are taken together to form a second bond between $C_{10}$ and $C_{11}$, $R_3$ is methyl, $R_5$ and $R_6$ are taken together to form a second bond between $C_5$ and $C_6$, $R_4$ and $R_8$ are taken together to form a didepsipeptide with the structure X, $R_9$ is methyl, and $R_{10}$ is isobutyl, $R_7$ is not 3-chloro-4-methoxybenzyl; and when $R_1$ and $R_2$ are taken together to form an epoxide group, $R_3$ is methyl, $R_5$ and $R_6$ are taken together to form a second bond between $C_5$ and $C_6$, $R_4$ is bonded to the carboxy terminus of leucic acid, and $R_8$ is bonded to the nitrogen terminus of either 3-amino-2-methylpropionic acid or 3-amino-2-methylpropionic acid methyl ester, $R_7$ is not 3-chloro-4-methoxybenzyl.

The invention further provides cryptophycin compounds wherein at least one of the groups attached to $C_2$, $C_8$, $C_9$, $C_{10}$, and $C_{11}$ has R sterochemistry. In a further embodiment of the invention, at least one of the groups attached to $C_2$, $C_8$, $C_9$, $C_{10}$, and $C_{11}$ has S sterochemistry.

The invention further provides cryptophycin compounds in accordance with the above structure where the structure of the didepsipeptide that is formed when $R_4$ or $R_5$ is taken together with $R_8$ is the following structure X:

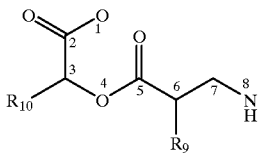

wherein $O_1$ of X corresponds to $R_4$ or $R_5$, $N_8$ of X corresponds to $R_8$, $R_9$ is H or a lower alkyl group, and $R_{10}$ is H or a lower alkyl group.

As used herein, "lower β-amino acid" means any β-amino acid having three to eight carbons and includes linear and non-linear hydrocarbon chains; for example, 3-amino-2-methylpropionic acid. As used herein, "esterified lower β-amino acid" means any β-amino acid having three to five carbons where the hydrogen of the carboxylic acid group is substituted with a methyl group; for example 3-amino-2-methylpropionic acid methyl ester. As used herein, "lower alkanoyloxy group" means an alkanoyloxy group of one to seven carbons and includes linear and non-linear hydrocarbon chains. As used herein, "lower α-hydroxyalkanoyloxy group" means an α-hydroxyalkanoyloxy group of two to seven carbons and includes linear and non-linear hydrocarbon chains; for example, 2-hydroxy-4-methylvaleric acid.

As used herein, "lower alkoxyl group" means any alkyl group of one to five carbons bonded to an oxygen atom. As used herein, "lower alkyl group" means an alkyl group of one to five carbons and includes linear and non-linear hydrocarbon chains including, for example, methyl, ethyl, propyl, isopropyl, butyl, isobutyl, tert-butyl, sec-butyl, methylated butyl groups, pentyl, tert-pentyl, sec-butyl, and methylated pentyl groups. As used herein, "allylically substituted alkene" means any alkene which contains an alkyl substitution on it.

As used herein, "epoxide ring" means a three-membered ring whose backbone consists of two carbons and an oxygen atom. As used herein, "aziridine ring" means a three-membered ring whose backbone consists of two carbons and a nitrogen atom. As used herein, "sulfide ring" means a three-membered ring whose backbone consists of two carbons and a sulfur atom. As used herein, "episulfide ring" means a three-membered ring whose backbone consists of two carbons and a sulfur atom. As used herein, "sulfate ring" means a five-membered ring consisting of a carbon—carbon-oxygen-sulfur-oxygen backbone with two additional oxygen atoms connected to the sulfur atom. As used herein, "monoalkylphosphate ring" means a five-membered ring consisting of a carbon—carbon-oxygen-phosphorus-oxygen backbone with two additional oxygen atoms, one of which bears a lower alkyl group, connected to the phosphorus atom.

As used herein, "simple unsubstituted aromatic group" refers to common aromatic rings having 4n+2 pi electrons in a monocyclic conjugated system (for example, furyl, pyrrolyl, thienyl, pyridyl) or a bicyclic conjugated system (for example, indolyl or naphthyl).

As used herein, "simple substituted aromatic group" refers to a phenyl group substituted with single group (e.g. a lower alkyl group or a halogen).

As used herein, "heteroaromatic group" refers to aromatic rings which contain one or more non-carbon substituents such as oxygen, nitrogen, or sulfur.

As used herein, "halogen" refers to those members of the group on the periodic table historically known as the halogens. Methods of halogenation include, but are not limited to, the addition of hydrogen halides, substitution at high temperature, photohalogenation, etc., and such methods are known to those of ordinary skill in the art.[1,2]

An example of a novel cryptophycin compound of the present invention is when $R_1$ and $R_2$ are taken together to form an epoxide group, $R_3$ is methyl, $R_5$ and $R_6$ are taken together to form a second bond between $C_5$ and $C_6$ such that there is a double bond, $R_7$ is 4-methoxybenzyl, and $R_4$ and $R_8$ are taken together to form the didepsipeptide with the structure X where $R_9$ is methyl and $R_{10}$ is isobutyl. The structure of this cryptophycin compound, Cryptophycin 2, is the following:

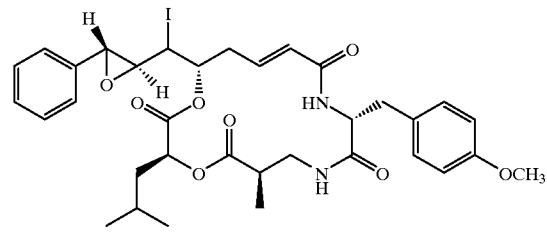

CRYPTOPHYCIN 2

A further example of a novel cryptophycin compound of the present invention is when $R_1$ and $R_2$ are taken together to form a second bond between the $C_{10}$ and $C_{11}$ carbons such that there is a double bond, $R_3$ is methyl, $R_5$ and $R_6$ are taken together to form a second bond between $C_5$ and $C_6$ such that there is a double bond, $R_7$ is 4-methoxybenzyl, and $R_4$ and $R_8$ are taken together to form the didepsipeptide with the structure X where $R_9$ is methyl and $R_{10}$ is isobutyl. The structure of this cryptophycin compound, Cryptophycin 4, is the following:

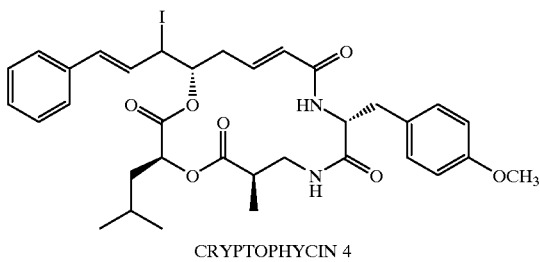

CRYPTOPHYCIN 4

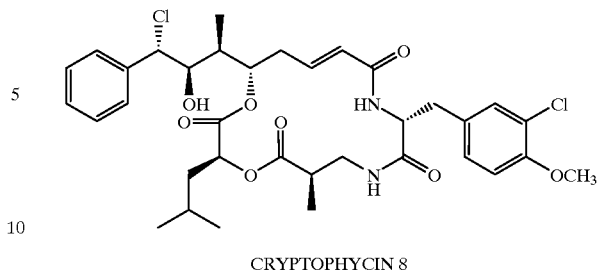

CRYPTOPHYCIN 8

A further example of a novel cryptophycin compound of the present invention is when $R_1$ and $R_4$ are taken together to form a tetrahydrofuran ring, $R_2$ is an OH group, $R_3$ is methyl, $R_5$ and $R_6$ are taken together to form a second bond between $C_5$ and $C_6$ such that there is a double bond, $R_7$ is 3-chloro-4-methoxybenzyl, and $R_8$ is a (2-carbomethoxypropyl)amino group. The structure of this cryptophycin compound, Cryptophycin 6, is the following:

A further example of a novel cryptophycin compound of the present invention is when $R_1$ is a methoxy group, $R_2$ is an OH group, $R_3$ is methyl, $R_5$ and $R_6$ are taken together to form a second bond between $C_5$ and $C_6$ such that there is a double bond, $R_7$ is 3-chloro-4-methoxybenzyl, and $R_4$ and $R_8$ are taken together to form the didepsipeptide with the structure X where $R_9$ is methyl and $R_{10}$ is isobutyl. The structure of this cryptophycin compound, Cryptophycin 9, is the following:

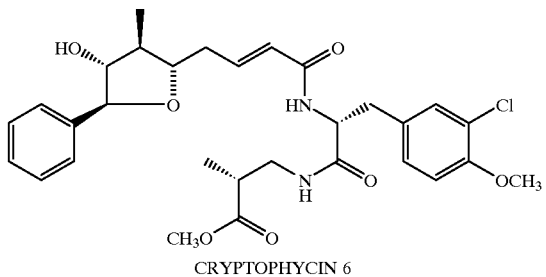

CRYPTOPHYCIN 6

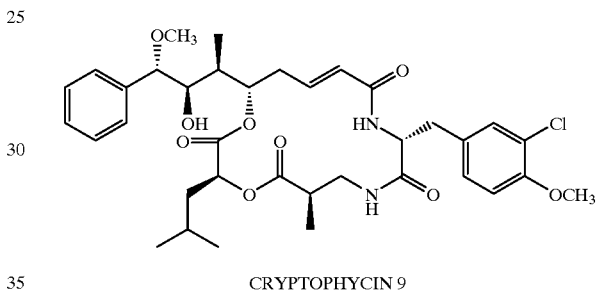

CRYPTOPHYCIN 9

A further example of a novel cryptophycin compound of the present invention is when $R_1$ and $R_4$ are taken together to form a tetrahydrofuran ring, $R_2$ and $R_8$ are OH groups, $R_3$ is methyl, $R_5$ and $R_6$ are taken together to form a second bond between $C_5$ and $C_6$ such that there is a double bond, $R_7$ is 3-chloro-4-methoxybenzyl. The structure of this cryptophycin compound, Cryptophycin 7, is the following:

A further example of a novel cryptophycin compound of the present invention is when $R_1$ is a methoxy group, $R_2$ and $R_4$ are OH groups, $R_3$ is methyl, $R_5$ and $R_6$ are taken together to form a second bond between $C_5$ and $C_6$ such that there is a double bond, $R_7$ is 3-chloro-4-methoxybenzyl, and $R_8$ is a (2-carboxypropyl)amino group. The structure of this cryptophycin compound, Cryptophycin 10, is the following:

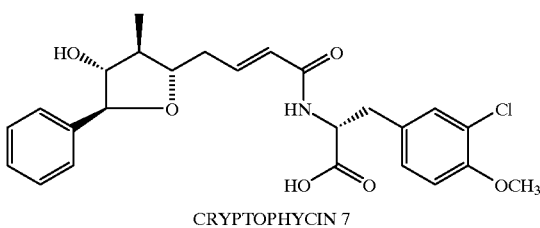

CRYPTOPHYCIN 7

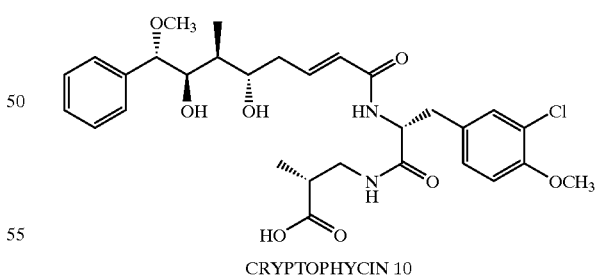

CRYPTOPHYCIN 10

A further example of a novel cryptophycin compound of the present invention is when $R_1$ is a chloro group, $R_2$ is an OH group, $R_3$ is methyl, $R_5$ and $R_6$ are taken together to form a second bond between $C_5$ and $C_6$ such that there is a double bond, $R_7$ is 3-chloro-4-methoxybenzyl, and $R_4$ and $R_8$ are taken together to form the didepsipeptide with the structure X where $R_9$ is methyl and $R_{10}$ is isobutyl. The structure of this cryptophycin compound, Cryptophycin 8, is the following:

A further example of a novel cryptophycin compound of the present invention is when $R_1$ and $R_4$ are taken together to form a tetrahydrofuran ring, $R_2$ is an OH group, $R_3$ is methyl, $R_5$ and $R_6$ are taken together to form a second bond between $C_5$ and $C_6$ such that there is a double bond, $R_7$ is 3-chloro-4-methoxybenzyl, and $R_8$ is a (2-carboxypropyl) amino group. The structure of this cryptophycin compound, Cryptophycin 12, is the following:

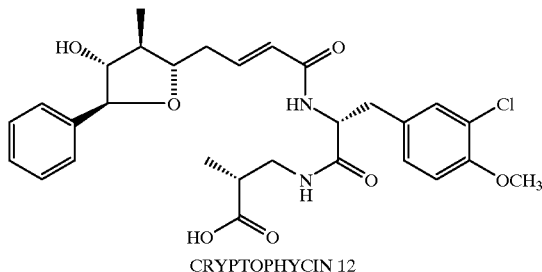

CRYPTOPHYCIN 12

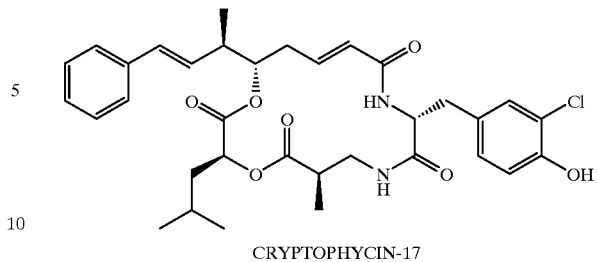

CRYPTOPHYCIN-17

A further example of a novel cryptophycin compound of the present invention is when $R_1$ and $R_2$ are taken together to form a second bond between the $C_{10}$ and $C_{11}$ carbons such that there is a double bond, $R_3$ is methyl, $R_4$ is an OH group, $R_5$ and $R_6$ are taken together to form a second bond between $C_5$ and $C_6$ such that there is a double bond, $R_7$ is 3-chloro-4-methoxybenzyl, and $R_8$ is a (2-carboxypropyl)amino group. The structure of this cryptophycin compound, Cryptophycin 14, is the following:

A further example of a novel cryptophycin compound of the present invention is when $R_1$ and $R_2$ are taken together to form a second bond between the $C_{10}$ and $C_{11}$ carbons such that there is a double bond, $R_3$ is methyl, $R_5$ and $R_6$ are taken together to form a second bond between $R_5$ and $R_6$ such that there is a double bond, $R_7$ is 3-chloro-4-methoxybenzyl, and $R_4$ and $R_8$ are taken together to form the didepsipeptide with the structure X where $R_9$ is methyl and $R_{10}$ is sec-butyl. The structure of this cryptophycin compound, Cryptophycin 18, is the following:

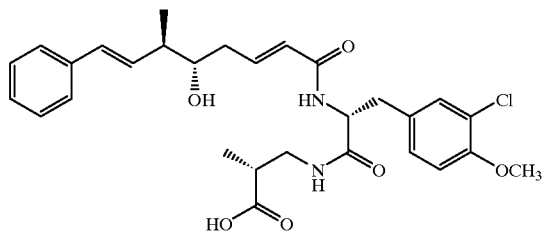

CRYPTOPHYCIN 14

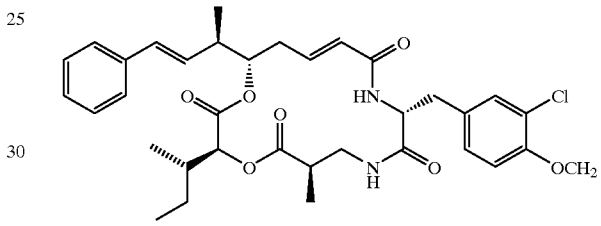

CRYPTOPHYCIN-18

A further example of a novel cryptophycin compound of the present invention is when $R_1$ and $R_2$ are taken together to form an epoxide group, $R_3$ is methyl, $R_4$ is an OH group, $R_5$ and $R_6$ are taken together to form a second bond between $C_5$ and $C_6$ such that there is a double bond, $R_7$ is 3-chloro-4-hydroxybenzyl, and $R_4$ and $R_8$ are taken together to form the didepsipeptide with the structure X where $R_9$ is methyl and $R_{10}$ is isobutyl. The structure of this cryptophycin compound, Cryptophycin 16, is the following:

A further example of a novel cryptophycin compound of the present invention is when $R_1$ and $R_2$ are taken together to form a second bond between the $C_{10}$ and $C_{11}$ carbons such that there is a double bond, $R_3$ is methyl, $R_5$ and $R_6$ are taken together to form a second bond between $R_5$ and $R_6$ such that there is a double bond, $R_7$ is 3-chloro-4-methoxybenzyl, and $R_4$ and $R_8$ are taken together to form the didepsipeptide with the structure X where $R_9$ is methyl and $R_{10}$ isopropyl. The structure of this cryptophycin compound, Cryptophycin 19, is the following:

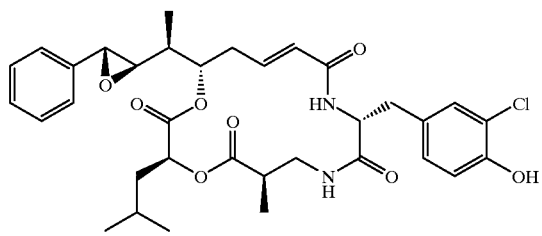

CRYPTOPHYCIN-16

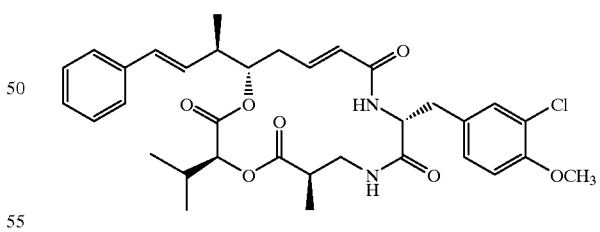

CRYPTOPHYCIN-19

A further example of a novel cryptophycin compound of the present invention is when $R_1$ and $R_2$ are taken together to form a second bond between the $C_{10}$ and $C_{11}$ carbons such that there is a double bond, $R_3$ is methyl, $R_5$ and $R_6$ are taken together to form a second bond between $R_5$ and $R_6$ such that there is a double bond, $R_7$ is 3-chloro-4-hydroxybenzyl, and $R_4$ and $R_8$ are taken together to form the didepsipeptide with the structure X where $R_9$ is methyl and $R_{10}$ isobutyl. The structure of this cryptophycin compound, Cryptophycin 17, is the following:

A further example of a novel cryptophycin compound of the present invention is when $R_1$ and $R_2$ are taken together to form an epoxide group, $R_3$ is methyl, $R_5$ and $R_6$ are taken together to form a second bond between $R_5$ and $R_6$ such that there is a double bond, $R_7$ is 3-chloro-4-methoxybenzyl, and $R_4$ and $R_8$ are taken together to form the didepsipeptide with the structure X where $R_9$ is hydrogen and $R_{10}$ isobutyl. The structure of this cryptophycin compound, Cryptophycin 21, is the following:

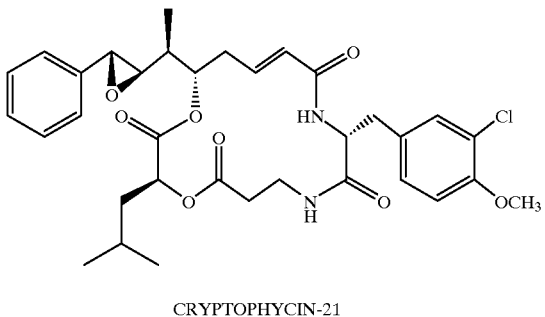

CRYPTOPHYCIN-21

A further example of a novel cryptophycin compound of the present invention is when $R_1$ and $R_2$ are taken together to form an epoxide group, $R_3$ is methyl, $R_5$ and $R_6$ are taken together to form a second bond between $R_5$ and $R_6$ such that there is a double bond, $R_7$ is 3,5-chloro-4-dichloro-4-hydroxybenzyl, and $R_4$ and $R_8$ are taken together to form the didepsipeptide with the structure X where $R_9$ is methyl and $R_{10}$ isobutyl. The structure of this cryptophycin compound, Cryptophycin 23, is the following:

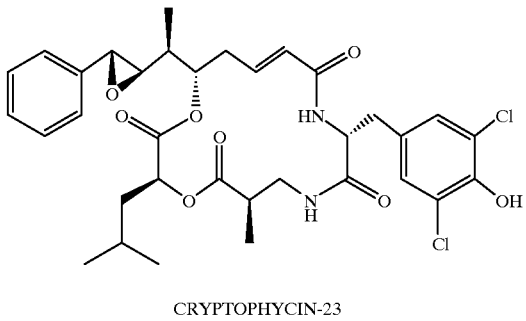

CRYPTOPHYCIN-23

A further example of a novel cryptophycin compound of the present invention is when $R_1$ and $R_2$ are taken together to form an epoxide group, $R_3$ is methyl, $R_5$ and $R_6$ are taken together to form a second bond between $R_5$ and $R_6$ such that there is a double bond, $R_7$ is 4-methoxybenzyl, and $R_4$ and $R_8$ are taken together to form the didepsipeptide with the structure X where $R_9$ is hydrogen and $R_{10}$ isobutyl. The structure of this cryptophycin compound, Cryptophycin 24, is the following:

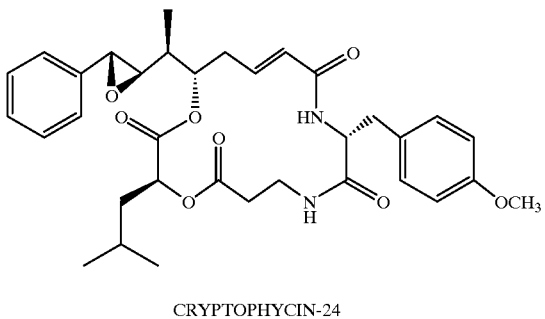

CRYPTOPHYCIN-24

A further example of a novel cryptophycin compound of the present invention is when $R_1$ and $R_2$ are taken together to form a second bond between $C_{10}$ and $C_{11}$ carbons such that there is a double bond, $R_3$ is methyl, $R_4$ is hydroxy, $R_6$ is hydrogen, $R_7$ is 3-chloro-4-methoxybenzyl, and $R_5$ and $R_8$ are taken together to form the didepsipeptide with the structure X where $R_9$ is methyl and $R_{10}$ is isobutyl. The structure of this cryptophycin compound, Cryptophycin 26, is the following:

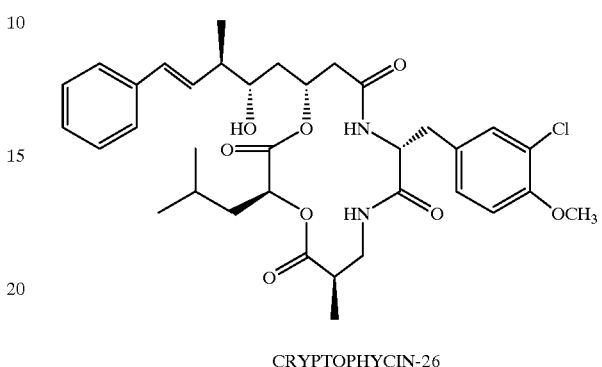

CRYPTOPHYCIN-26

A further example of a novel cryptophycin compound of the present invention is when $R_1$ and $R_2$ are taken together to form a second bond between $C_{10}$ and $C_{11}$ carbons such that there is a double bond, $R_3$ is hydrogen, $R_5$ and $R_6$ are taken together to form a second bond between $C_5$ and $C_6$ such that there is a double bond, $R_7$ is 3-chloro-4-methoxybenzyl, and $R_4$ and $R_8$ are taken together to form the didepsipeptide with the structure X where $R_9$ is methyl and $R_{10}$ is isobutyl. The structure of this cryptophycin compound, Cryptophycin 28, is the following:

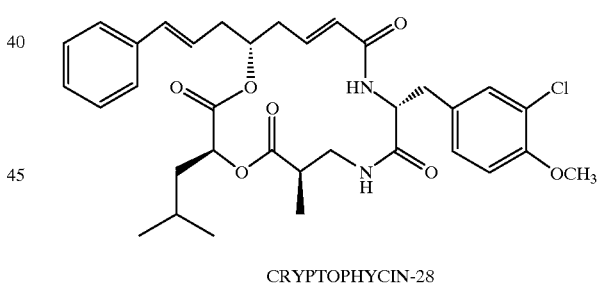

CRYPTOPHYCIN-28

A further example of a novel cryptophycin compound of the present invention is when $R_1$ and $R_2$ are taken together to form a second bond between $C_{10}$ and $C_{11}$ carbons such that there is a double bond, $R_3$ is methyl, $R_5$ and $R_6$ are taken together to form a second bond between $C_5$ and $C_6$ such that there is a double bond, $R_7$ is 3-chloro-4-methoxybenzyl, and $R_4$ and $R_8$ are taken together to form the didepsipeptide with the structure X where $R_9$ is hydrogen and $R_{10}$ is isobutyl. The structure of this cryptophycin compound, Cryptophycin 29, is the following:

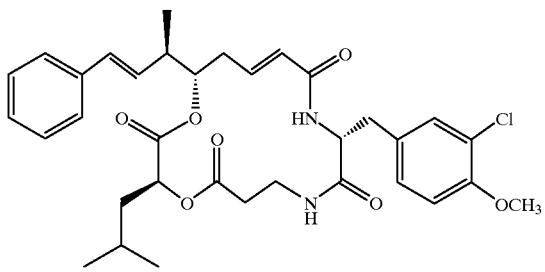

CRYPTOPHYCIN-29

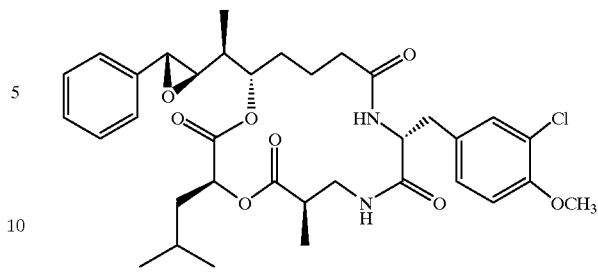

CRYPTOPHYCIN-35

A further example of a novel cryptophycin compound of the present invention is when $R_1$ and $R_2$ are taken together to form a second bond between $C_{10}$ and $C_{11}$ carbons such that there is a double bond, $R_3$ is methyl, $R_5$ is hydroxy, $R_6$ is hydrogen, $R_7$ is 3-chloro-4-methoxybenzyl, and $R_4$ and $R_8$ are taken together to form the didepsipeptide with the structure X where $R_9$ is methyl and $R_{10}$ is isobutyl. The structure of this cryptophycin compound, Cryptophycin 30, is the following:

A further example of a novel cryptophycin compound of the present invention is when $R_1$ and $R_2$ are taken together to form an epoxide group, $R_3$ is methyl, $R_5$ and $R_6$ are taken together to form a second bond between $C_5$ and $C_6$ such that there is a double bond, $R_7$ is 3,-chloro-methoxybenzyl, and $R_4$ and $R_8$ are taken together to form the didepsipeptide with the structure X where $R_9$ is methyl and $R_{10}$ is isobutyl. The structure of this cryptophycin compound, Cryptophycin 40, is the following:

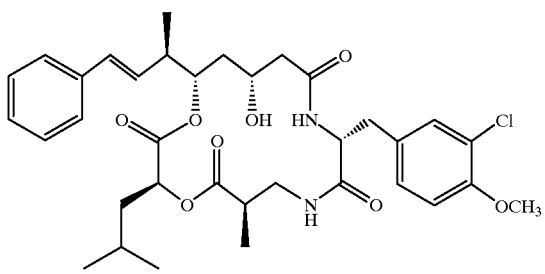

CRYPTOPHYCIN-30

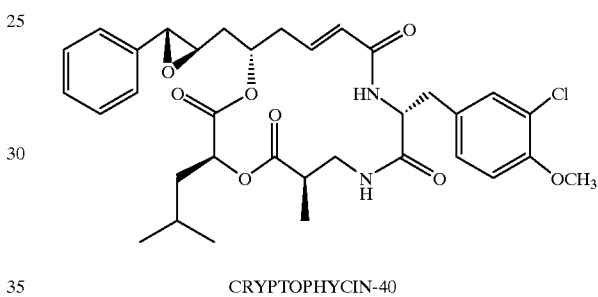

CRYPTOPHYCIN-40

A further example of a novel cryptophycin compound of the present invention is when $R_1$ and $R_2$ are taken together to form an epoxide group, $R_3$ is methyl, $R_5$ and $R_6$ are taken together to form a second bond between $C_5$ and $C_6$ such that there is a double bond, $R_7$ is 3,5-chloro-4-methoxybenzyl, and $R_4$ and $R_8$ are taken together to form the didepsipeptide with the structure X where $R_9$ is methyl and $R_{10}$ is isobutyl. The structure of this cryptophycin compound, Cryptophycin 31, is the following:

A further example of a novel cryptophycin compound of the present invention is when $R_1$ and $R_2$ are taken together to form a second bond between the $C_{10}$ and $C_{11}$ carbons such that there is a double bond, $R_3$ is methyl, $R_5$ and $R_6$ are taken together to form a second bond between $C_5$ and $C_6$ such that there is a double bond, $R_7$ is 3,5-dichloro-4-hydroxybenzyl, and $R_4$ and $R_8$ are taken together to form the didepsipeptide with the structure X where $R_9$ is methyl and $R_{10}$ is isobutyl. The structure of this cryptophycin compound, Cryptophycin 45, is the following:

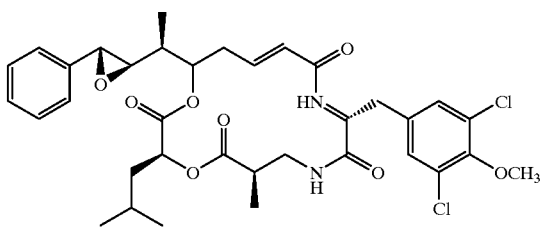

CRYPTOPHYCIN-31

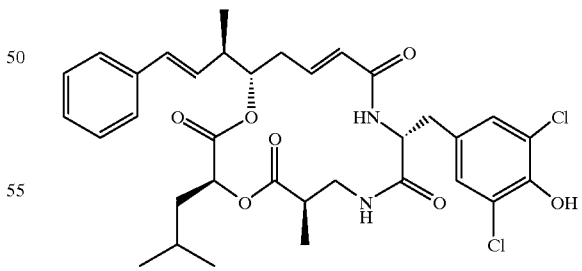

CRYPTOPHYCIN-45

A further example of a novel cryptophycin compound of the present invention is when $R_1$ and $R_2$ are taken together to form an epoxide group, $R_3$ is methyl, $R_5$ is hydrogen, $R_6$ is hydrogen, $R_7$ is 3,-chloro-4-methoxybenzyl, and $R_4$ and $R_8$ are taken together to form the didepsipeptide with the structure X where $R_9$ is methyl and $R_{10}$ is isobutyl. The structure of this cryptophycin compound, Cryptophycin 35, is the following:

A further example of a novel cryptophycin compound of the present invention is when $R_1$ and $R_2$ are taken together to form an epoxide group, $R_3$ is methyl, $R_5$ and $R_6$ are taken together to form a second bond between $C_5$ and $C_6$ such that there is a double bond, $R_7$ is 3,-chloro-methoxybenzyl, and $R_4$ and $R_8$ are taken together to form the didepsipeptide with the structure X where $R_9$ is methyl and $R_{10}$ is propyl. The structure of this cryptophycin compound, Cryptophycin 49, is the following:

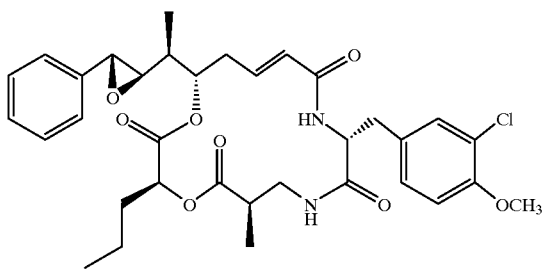

CRYPTOPHYCIN-49

A further example of a novel cryptophycin compound of the present invention is when $R_1$ and $R_2$ are taken together to form a second bond between the $C_{10}$ and $C_{11}$ carbons such that there is a double bond, $R_3$ is methyl, $R_5$ and $R_6$ are taken together to form a second bond between $C_5$ and $C_6$ such that there is a double bond, $R_7$ is 3-dichloro-4-methoxybenzyl, and $R_4$ and $R_8$ are taken together to form the didepsipeptide with the structure X where $R_9$ is methyl and $R_{10}$ is propyl. The structure of this cryptophycin compound, Cryptophycin 50, is the following:

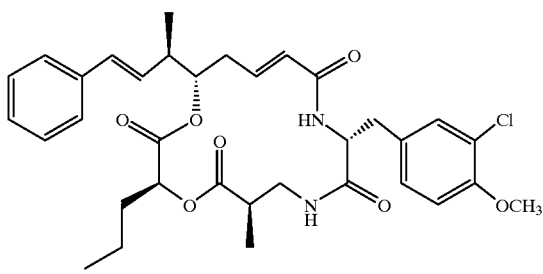

CRYPTOPHYCIN-50

A further example of a novel cryptophycin compound of the present invention is when $R_1$ and $R_2$ are taken together to form an epoxide group, $R_3$ is methyl, $R_5$ and $R_6$ are taken together to form a second bond between $C_5$ and $C_6$ such that there is a double bond, $R_7$ is 3,-chloro-methoxybenzyl, and $R_4$ and $R_8$ are taken together to form the didepsipeptide with the structure X where $R_9$ is methyl and $R_{10}$ is sec-butyl. The structure of this cryptophycin compound, Cryptophycin 54, is the following:

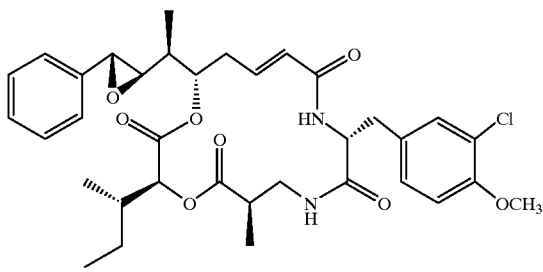

CRYPTOPHYCIN-54

Of the above compounds, Cryptophycins 2, 4, 16–19, 21, 23, 24, 26, 28–31, 40, 43, 45, 49, 50, and 54 are metabolites produced by a strain of Nostoc sp. of blue-green algae (cyanobacteria) which has been cultured, with these compounds subsequently isolated from this culture. Cryptophycins 6 and 7 are artifacts that are produced if the isolation procedure utilizes solvents containing methanol. Cryptophycins 8, 9, 10–12, 14, and 35 are derivatives of these naturally-produced metabolites, having been chemically modified with the methods described in the Experimental Section of this application, with alternate methods to create the exemplified compounds, as well as the non-exemplified compounds, available to those of ordinary skill in the art.

The present invention provides methods of producing the above cryptophycin compounds through the culturing of a strain of the Nostoc sp. The morphological characteristics of the Nostoc sp. of blue-green algae (cyanobacteria), as provided in U.S. Pat. No. 4,946,835, are that they are filamentous and consist of vegetative cells. In longer filaments, heterocysts occasionally are observed in an intercalary position. Akinetes are not observed. Reproduction is by hormogonia in addition to random trichome breakage. The basis for an identification of a Nostoc sp. can be found in J. Gen. Micro., 111:1–61 (1979).

The invention further provides that a Nostoc sp. may be cultured and that novel cryptophycin metabolites, as well as previously disclosed cryptophycin metabolites, may be isolated from this culture. In a preferred embodiment of the present invention, the Nostoc sp. strain designated GSV 224 is the strain which is cultivated and from which are isolated compounds represented by the following structure:

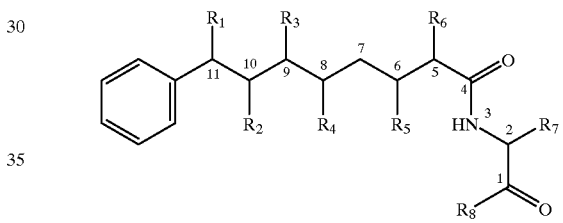

Wherein $R_1$ is H, OH, a halogen, O of a ketone group, $NH_2$, SH, a lower alkoxyl groups or a lower alkyl group;

$R_2$ is H, OH, O of a ketone group, $NH_2$, SH, a lower alkoxyl group or a lower alkyl group; or $R_1$ and $R_2$ may be taken together to form an epoxide ring, an aziridene ring, a sulfide ring or a second bond between $C_{10}$ and $C_{11}$; or $R_1$ and $R_4$ may be taken together to form a tetrahydrofuran ring;

$R_3$ is H or a lower alkyl group;

$R_4$ is OH, a lower alkanoyloxy group or a lower α-hydroxy alkanoyloxy group;

$R_5$ is H or an OH group;

$R_6$ is H; or $R_5$ and $R_6$ may be taken together to form a second bond between $C_5$ and $C_6$;

$R_7$ is a benzyl, hydroxybenzyl, methoxybenzyl, halohydroxybenzyl, dihalohydroxybenzyl, halomethoxybenzyl, or dihalomethoxybenzyl group;

$R_8$ is OH, a lower β-amino acid wherein $C_1$ is bonded to N of the β-amino acid, or an esterified lower β-amino acid wherein $C_1$ is bonded to N of the esterified lower β-amino acid group;

$R_4$ and $R_8$ may be taken together to form a didepsipeptide group consisting of a lower β-amino acid bonded to a lower α-hydroxy alkanoic acid; and $R_5$ and $R_8$ may be taken together to form a didepsipeptide group consisting of a lower β-amino acid bonded to a lower α-hydroxy alkanoic acid; and with the following provisos;

$R_1$ H, a lower alkyl group, or a lower alkoxyl group only if $R_2$ is OH, O of a ketone group, $NH_2$, SH.

In a preferred embodiment of the invention, chemically modifying a cryptophycin metabolite isolated by the above method provides a distinct compound also having this structure. Procedures for chemically modifying cryptophycin compounds to produce additional compounds within the scope of the present invention are available to those of ordinary skill in the art. Moreover, additional procedures are described in greater detail in the Experimental Section of this application.

In addition to the novel cryptophycin compounds of the present invention, the present invention provides novel methods of producing, as well as using, the above structure which includes the following previously disclosed cryptophycin species, Cryptophycins 1, 3, 5, 13 and 15. The structures of these compounds are the following:

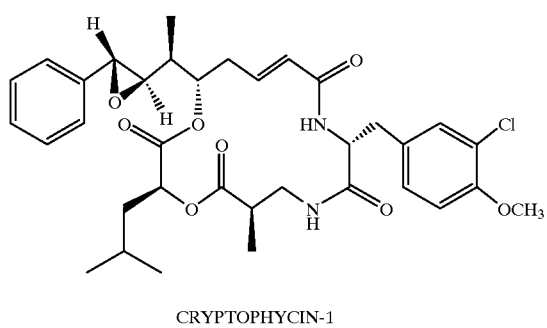

CRYPTOPHYCIN-1

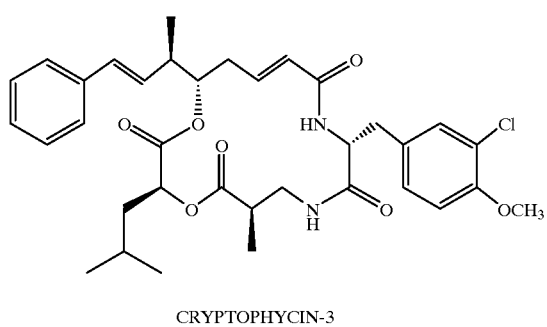

CRYPTOPHYCIN-3

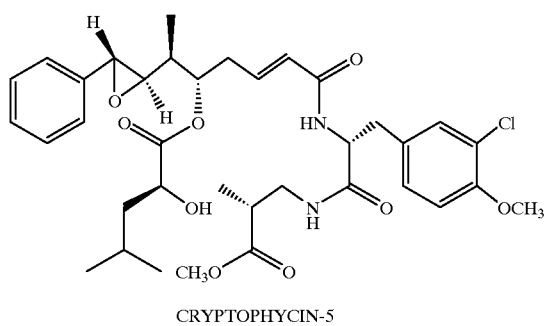

CRYPTOPHYCIN-5

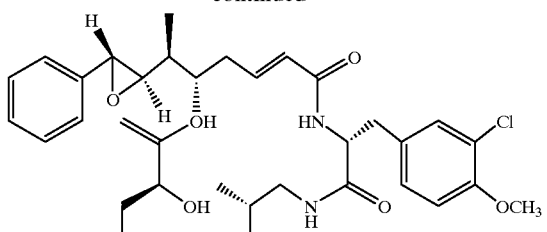

CRYPTOPHYCIN-13

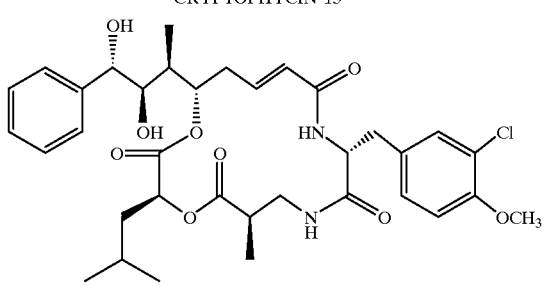

CRYPTOPHYCIN-15

The invention provided herewith is directed to any strain of the Nostoc sp. and preferably to the Nostoc sp. GSV 224 strain to produce cryptophycin compounds. To that end, the GSV 224 strain of Nostoc sp. was deposited on Oct. 7, 1993 pursuant to the Budapest Treaty on the International Deposit of Microorganisms for the Purposes of Patent Procedure with the Patent Culture Depository of the American Type Culture Collection, 12301 Parklawn Drive, Rockville, Md. 20582 U.S.A. under ATCC Accession No. 55483. Other strains of Nostoc sp., in particular strain MB 5357 previously deposited by Merck and Co. under ATCC accession No. 53789, are strains contemplated to be utilized to practice the present invention.

As is the case with other organisms, the characteristics of Nostoc sp. are subject to variation. For example, recombinants, variants, or mutants of the specified strains may be obtained by treatment with various known physical and chemical mutagens, such as ultraviolet ray, X-rays, gamma rays, and N-methyl-N'-nitro-N-nitrosoguanidine. All natural and induced variants, mutants, and recombinants of the specified strains which retain the characteristic of producing a cryptophycin compound are intended to be within the scope of the claimed invention.

The cryptophycin compounds of the present invention can be prepared by culturing a strain of Nostoc sp. under submerged aerobic conditions in a suitable culture medium until substantial antibiotic activity is produced. Other culture techniques, such as surface growth on solidified media, can also be used to produce these compounds. The culture medium used to grow the specified strains can include any of one of many nitrogen and carbon sources and inorganic salts that are known to those of ordinary skill in the art. Economy in production, optimal yields, and ease of product isolation are factors to consider when choosing the carbon sources and nitrogen sources to be used. Among the nutrient inorganic salts which can be incorporated in the culture media are the customary soluble salts capable of yielding iron, potassium, sodium, magnesium, calcium, ammonium, chloride, carbonate, phosphate, sulfate, nitrate, and like ions.

Essential trace elements which are necessary for the growth and development of the organisms should also be include din the culture medium. Such trace elements commonly occur as impurities in other constituents of the medium in amounts sufficient to meet the growth requirements of the organisms. It may be desirable to add small amounts (i.e. 0.2 mL/L) of an antifoam agent such as polypropylene glycol (M.W. about 2000) to large scale cultivation media if foaming becomes a problem.

For production of substantial quantities of the cryptophycin compounds, submerged aerobic cultivation in tanks can be used. Small quantities may be obtained by shake-flask culture. Because of the time lag in metabolite production commonly associated with inoculation of large tanks with the organisms, it is preferable to use a vegatative inoculum. The vegetative inoculum is prepared by inoculating a small volume of culture medium with fragments of the vegetative trichome or heterocyst-containing form of the organism to obtain a fresh, actively growing culture of the organism. The vegative inoculum is then transferred to a larger tank. The medium used for the vegetative inoculum can be the same as that used for larger cultivations or fermentation, but other media can also be used.

The organisms may be grown at temperatures between about 20° C. and 30° C. and an incident illumination intensity of about 100 to 200 $\mu$mol photons $m^{-2}Sec^{-1}$ (photosynthetically active radiation).

As is customary in aerobic submerged culture processes of this type, carbon dioxide gas is introduced into the culture by addition to the sterile air stream bubbled through the culture medium. For efficient production of the cryptophycin compounds, the proportion of carbon dioxide should be about 1% (at 24° C. and one atomosphere of pressure).

The prior art, specifically U.S. Pat. No. 4,946,835, provides methods of cultivating Nostoc sp., the contents of which are hereby incorporated by reference.

Cryptophycin compound production can be followed during the cultivation by testing samples of the broth against organisms known to be sensitive to these antibiotics. One useful assay organism is *Candida albicans*.

Following their production under submerged aerobic culture conditions, cryptophycin compounds of the invention can be recovered from the culture and from the culture media by methods known to those of ordinary skill in this art. Recovery is generally accomplished by initially filtering the culture medium to separate the algal cells and then freeze-drying the separated cells. The freeze-dried alga can be extracted with a suitable solvent such as ethanol, methanol, isopropanol, or dichloromethane. The cryptophycins can be separated by subjecting this extract, as well as the culture media, to rapid chromatography on reversed-phase column. The cryptophycins can be purified by reversed-phase high-performance liquid chromatography (HPLC).

As will be apparent from their structures, the cryptophycin compounds have groups which are capable of chemical modification. The genus compound of the present invention contemplates those cryptophycins which exhibit anti-neoplastic activity. For example, the derivatives exemplified in the present invention include compounds having the epoxide oxygen of hydroxy groups on C-7 and C-8 of Unit A or the leucic acid group of unit B of FIG. 1. Such derivatives of the novel and previously disclosed compounds which display the desired anti-neoplastic acitivity are included in the claimed invention. Moreover, the relationship between the structure of the cryptophycin compounds and anti-neoplastic activity is provide in the Experimental Section hereinbelow.

While selected cryptophycin compounds are known to be metabolites produced by the alga of the present invention, other cryptophycin compounds, e.g. Cryptophycins 8–15, can be derived from the metabolites using published techniques which are known to those of ordinary skill in the art; for example, the syntheses disclosed in U.S. Pat. Nos. 4,868,208, 4,845,086, and 4,845,085, the contents of which are hereby incorporated by reference, or by utilizing other methods which are known to those of ordinary skill in the art. Moreover, the present invention provides methods of producing derivatives in the Experimental Section.

Cryptophycins are potent antitumor and antifungal depsipeptides from blue-green algae (cyanobacteria) belonging to the Nostocaceae. The first cryptophycin, Cryptophycin 1, was isolated from terrestrial Nostoc sp. ATCC 53789 and found to be very active against fungi, especially strains of Cryptococcus (R. E. Schwartz et al., *J. Ind. Microbiol.* 1990, 5, 113–24). Cryptophycin 1 has also been isolated from terrestrial Nostoc sp. GSV 224, along with twenty-four additional cryptophycin analogs as minor constituents of the alga, and found to be very active against subcutaneously transplanted solid tumors in mice (G. Trimurtulu et al., *J. Am. Chem. Soc.* 1994, 116, 4729–4737; R. Barrow et al., *J. Am. Chem. Soc.* 1995, 117, March 8 issue). Two of the analogs from Nostoc sp. GSV 224, Cryptophycins 3 and 5, had been described previously as semi-synthetic analogs of Cryptophycin 1 (D. F. Sesin, U.S. Pat. No. 4,845,085, issued Jul. 4, 1989; D. F. Sesin et al., U.S. Pat. No. 4,868,208, issued Sep. 19, 1989). The cryptophycins showed significant tumor selective cytotoxicity in the Corbett assay and were equally cytotoxic against drug sensitive and drug resistant tumor cells. Cryptophycin 1 appeared to have the same mode of action as vinblastine, but differed from the latter drug in irreversibly inhibiting mircotubule assembly (C. D. Smith et al., *Cancer Res.* 1994, 54, 3779–84). One of the cryptophycins from Nostoc sp. GSV 224, Cryptophycin 24, has been isolated from a marine sponge and named arenastatin A (M. Kobayashi et al., *Tetrahedron Lett.* 1994, 35, 7969–72; M. Kobayashi et al., *Tennen Yuki Kagobustsu Toronkai Koen Yoshishu* 1994, 36st, 104–110).

Twenty-two additional cryptophycin compounds, herein designated Cryptophycins 2, 4, 6, 7, 16–19, 21, 23, 24, 26, 28–31, 40, 43, 45, 49, 50 and 54 are disclosed in U.S. patent application Ser. Nos. 08/172,632 filed Dec. 21, 1993 and 08/249,955 filed May 27, 1994 and International Application Ser. No. PCT/US94/14740 filed Dec. 21, 1994, such compounds either being metabolites isolated from a strain of Nostoc sp. or having been semi-synthesized from such metabolites. Also disclosed in these patent applications is the characterization of selected cryptophycin compounds as anti-microtubule agents with clinical-type activity expressed toward a broad spectrum of tumors implanted in mice, including DR and MDR tumors.

The present invention provides novel cryptophycin compounds having the following structure:

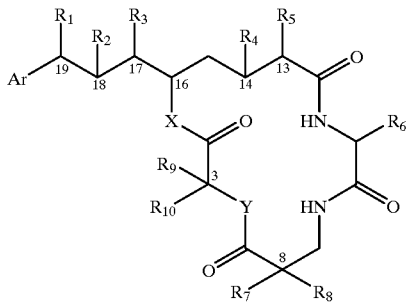

wherein

Ar is phenyl or any simple unsubstituted or substituted aromatic or heteroaromatic group;

$R_1$ is a halogen, SH, amino, monoalkylamino, dialkylamino, trialkylammonium, alkylthio, dialkylsufonium, sulfate, or phosphate;

$R_2$ is OH or SH; or $R_1$ and $R_2$ may be taken together to form an epoxide ring, an aziridene ring, an episulfide ring, a sulfate ring or a monoalkylphosphate ring; or $R_1$ and $R_2$ may be taken together to form a second bond between $C_{18}$ and $C_{19}$;

$R_3$ is a lower alkyl group;

$R_4$ is H;

$R_5$ is H;

$R_4$ and $R_5$ may be taken together to form a second bond between $C_{13}$ and $C_{14}$;

$R_6$ is a benzyl, hydroxybenzyl, alkoxybenzyl, halohydroxybenzyl, dihalohydroxybenzyl, haloalkoxybenzyl, or dihaloalkoxybenzyl group;

$R_7$ is H or a lower alkyl group;

$R_8$ is H or a lower alkyl group;

$R_9$ is H or a lower alkyl group;

$R_{10}$ is H or a lower alkyl group;

X is O, NH or alkylamino; and

Y is O, NH or alkylamino. In a preferred embodiment of this cryptophycin, $R_8$ of the cryptophycin is ethyl, propyl, isopropyl, butyl, isobutyl, pentyl or isopentyl. In another preferred embodiment of this cryptophycin, $R_7$ is ethyl, propyl, ispryopy, butyl, isobutyl, pentyl or isopentyl. In an additional preferred embodiment of this cryptophycin, $R_7$ is H, $R_8$ is methyl, $R_3$ is methyl; X and Y are not both O.

The present invention provides an additional preferred embodiment of this cryptophycin wherein $R_3$ is ethyl, propyl, isopropyl, butyl, isobutyl, pentyl or isopentyl. In an another preferred embodiment of this cryptophycin, $R_9$ is methyl, ethyl, propyl, butyl, isobutyl, pentyl or isopentyl. In a further preferred embodiment of this cryptophycin, $R_{10}$ is methyl, ethyl, propyl, butyl, isobutyl, pentyl or isopentyl.

The invention further provides cryptophycin compounds wherein at least one of the groups attached to $C_3$, $C_6$, $C_{10}$, $C_{16}$, $C_{17}$, and $C_{18}$ has R sterochemistry. In a further embodiment of the invention, at least one of the groups attached to $C_3$, $C_6$, $C_{10}$, $C_{16}$, $C_{17}$, and $C_{18}$ has S An example of a novel cryptophycin compound of the present invention is when $R_1$ and $R_2$ are taken together to form a second bond between $C_{18}$ and $C_{19}$, $R_3$, $R_7$ and $R_8$ are methyl, $R_4$ and $R_5$ are taken together to form a second bond between $C_{13}$ and $C_{14}$ such that there is a double bond, $R_6$ is 3-chloro-4-methoxybenzyl, $R_9$ is isobutyl, $R_{10}$ is hydrogen, and X and Y are oxygen. The structure of this cryptophycin compound, Cryptophycin 51, is the following:

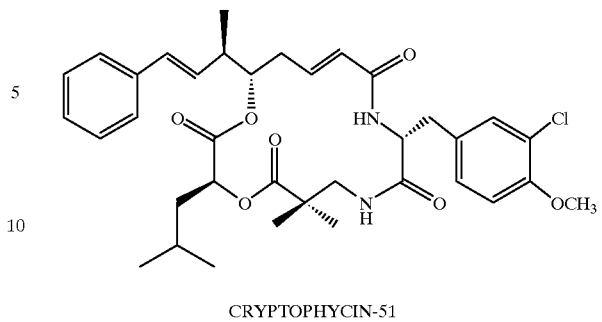

CRYPTOPHYCIN-51

CRYPTOPHYCIN 51

Another example of a novel cryptophycin compound of the present invention is when $R_1$ and $R_2$ are taken together to form a R,R-epoxide ring, $R_3$, $R_7$ and $R_8$ are methyl, $R_4$ and $R_5$ are taken together to form a second bond between $C_{13}$ and $C_{14}$ such that there is a double bond, $R_6$ is 3-chloro-4-methoxybenzyl, $R_9$ is isobutyl, $R_{10}$ is hydrogen, and X and Y are oxygen. The structure of this cryptophycin compound, Cryptophycin 52, is the following:

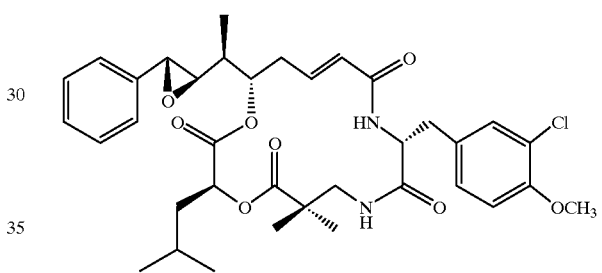

CRYPTOPHYCIN-52

CRYPTOPHYCIN 52

Another example of a novel cryptophycin compound of the present invention is when $R_1$ and $R_2$ are taken together to form a S,S-epoxide ring, $R_3$, $R_7$ and $R_8$ are methyl, $R_4$ and $R_5$ are taken together to form a second bond between $C_{13}$ and $C_{14}$ such that there is a double bond, $R_6$ is 3-chloro-4-methoxybenzyl, $R_9$ is isobutyl, $R_{10}$ is hydrogen, and X and Y are oxygen. The structure of this cryptophycin compound, Cryptophycin 53, is the following:

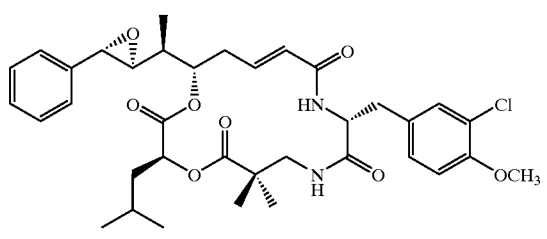

CRYPTOPHYCIN-53

CRYPTOPHYCIN 53

Another example of a novel cryptophycin compound of the present invention is when $R_1$ is chloro, $R_2$ is hydroxyl, $R_3$, $R_7$ and $R_8$ are methyl, $R_4$ and $R_5$ are taken together to form a second bond between $C_{13}$ and $C_{14}$ such that there is a double bond, $R_6$ is 3-chloro-4-methoxybenzyl, $R_9$ is isobutyl, $R_{10}$ is hydrogen, and X and Y are oxygen. The structure of this cryptophycin compound, Crytophycin 55, is the following:

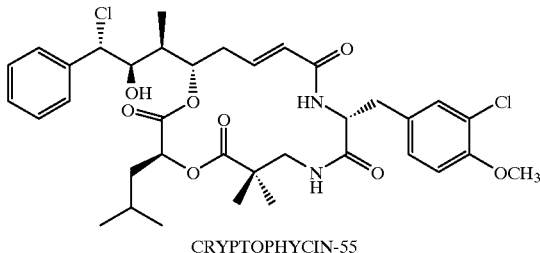

CRYPTOPHYCIN-55

CRYPTOPHYCIN 55

Another example of a novel cryptophycin compound of the present invention is when $R_1$ and $R_2$ are taken together to form an epoxide ring, $R_3$, $R_7$ and $R_8$ are methyl, $R_4$ and $R_5$ are hydrogen, $R_6$ is 3-chloro-4-methoxybenzyl, $R_9$ is isobutyl, $R_{10}$ is hydrogen, and X and Y are oxygen. The structure of this cryptophycin compound, Cryptophycin 57, is the following:

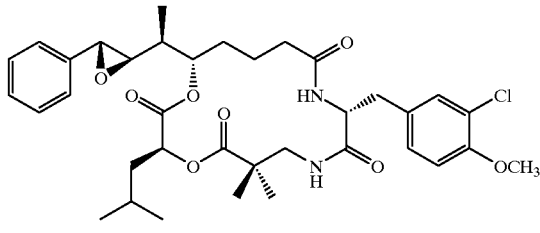

CRYPTOPHYCIN-57

CRYPTOPHYCIN 57

Another example of a novel cryptophycin compound of the present invention is when $R_1$ is chloro, $R_2$ is hydroxyl, $R_3$, $R_7$ and $R_8$ are methyl, $R_4$ and $R_5$ are hydrogen, $R_6$ is 3-chloro-4-methoxybenzyl, $R_9$ is isobutyl, $R_{10}$ is hydrogen, and X and Y are oxygen. The structure of this cryptophycin compound, Crytophycin 58, is the following:

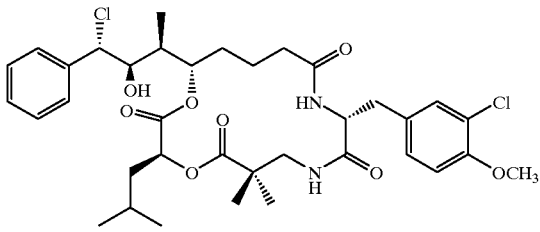

CRYPTOPHYCIN-58

CRYPTOPHYCIN 58

Another example of a novel cryptophycin compound of the present invention is when $R_1$ and $R_2$ are taken together to form a R,R-epoxide ring, $R_3$, $R_7$ and $R_8$ are methyl, $R_4$ and $R_5$ are taken together to form a second bond between $C_{13}$ and $C_{14}$ such that there is a double bond, $R_6$ is 3-chloro-4-methoxybenzyl, $R_9$ is isobutyl, $R_{10}$ is hydrogen, and X and Y are oxygen. This structure is known as Cryptophycin 61.

The present invention provides methods of producing the above cryptophycin compounds, as well as all previously known cryptophycins, through total synthesis.

The invention further provides that novel cryptophycin metabolites, as well as previously disclosed cryptophycin metabolites, may be synthesized using the methods provided in this invention.

The present invention provides a method for producing a cryptophycin comprising selecting an allylically substituted E alkene; rearranging the allylically substituted E alkene via a sterospecific Wittig rearrangement; converting this compound to a first δ-amino acid or δ-hydroxy acid; coupling the first acid to a second α-amino acid to form a first subunit; coupling a third B-amino acid to a fourth α-hydroxy acid or α-amino acid to form a first subunit; and coupling the first subunit to the second subunit to form a cryptophycin.

The present invention further provides a preferred embodiment of the method, wherein the cryptophycin produced has the following structure:

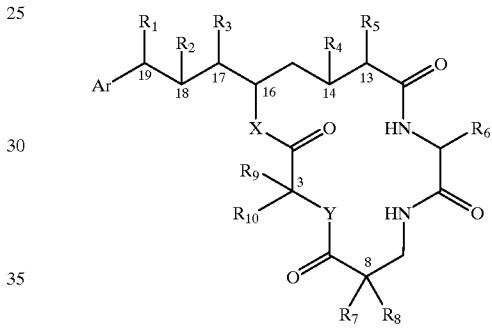

wherein

Ar is phenyl or any simple unsubstituted or substituted aromatic or heteroaromatic group;

$R_1$ is a halogen, SH, amino, monoalkylamino, dialkylamino, trialkylammonium, alkylthio, dialkylsufonium, sulfate, or phosphate;

$R_2$ is OH or SH; or $R_1$ and $R_2$ may be taken together to form an epoxide ring, an aziridene ring, an episulfide ring, a sulfate ring or a monoalkylphosphate ring; or $R_1$ and $R_2$ may be taken together to form a second bond between $C_{18}$ and $C_{19}$;

$R_3$ is a lower alkyl group;

$R_4$ is H;

$R_5$ is H;

$R_4$ and $R_5$ may be taken together to form a second bond between $C_{13}$ and $C_{14}$;

$R_6$ is a benzyl, hydroxybenzyl, alkoxybenzyl, halohydroxybenzyl, dihalohydroxybenzyl, haloalkoxybenzyl, or dihaloalkoxybenzyl group;

$R_7$ is H or a lower alkyl group;

$R_8$ is H or a lower alkyl group;

$R_9$ is H or a lower alkyl group;

$R_{10}$ is H or a lower alkyl group;

X is O, NH or alkylamino; and

Y is O, NH or alkylamino. In a preferred embodiment of the present invention, the method produces a cryptophycin wherein Ar is phenyl; $R_3$ is methyl; $R_6$ is methoxybenzyl; $R_7$ is H; $R_8$ is methyl; $R_9$ is isobutyl; $R_{10}$ is H; X is O; and Y is O.

In addition to the present invention providing cryptophycins with the above structure, the present invention provides methods of producing previously disclosed cryptophycins and prior cryptophycins. Cryptophycins 1, 8 and 35 were produced by total synthesis. Provided hereinbelow is a representation of previously disclosed and prior art cryptophycins produced by total synthesis:

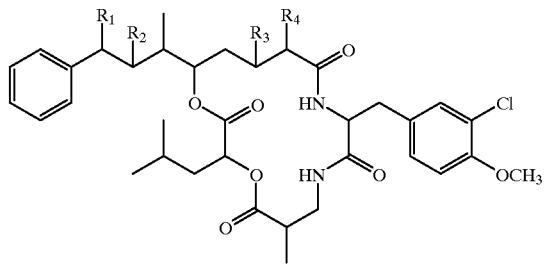

wherein
$R_1$ is a halogen; $R_2$ is OH; or
$R_1$ and $R_2$ may be taken together to form an epoxide ring;
$R_3$ is H; and $R_4$ is H; or
$R_3$ and $R_4$ may be taken together to form a second bond.

The present invention also provides a pharmaceutical composition useful for inhibiting the proliferation of a hyperproliferative mammalian cell comprising an effective amount of a cryptophycin with the following structure:

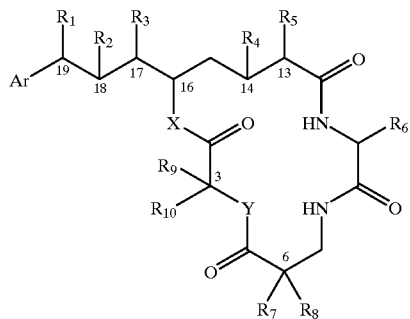

wherein
Ar is phenyl or any simple unsubstituted or substituted aromatic or heteroaromatic group;
$R_1$ is a halogen, SH, amino, monoalkylamino, dialkylamino, trialkylammonium, alkylthio, dialkylsufonium, sulfate, or phosphate;
$R_2$ is OH or SH; or
$R_1$ and $R_2$ may be taken together to form an epoxide ring, an aziridene ring, an episulfide ring, a sulfate ring or a monoalkylphosphate ring; or
$R_1$ and $R_2$ may be taken together to form a second bond between $C_{18}$ and $C_{19}$;
$R_3$ is a lower alkyl group;
$R_4$ is H;
$R_5$ is H;
$R_4$ and $R_5$ may be taken together to form a second bond between $C_{13}$ and $C_{14}$;
$R_6$ is a benzyl, hydroxybenzyl, alkoxybenzyl, halohydroxybenzyl, dihalohydroxybenzyl, haloalkoxybenzyl, or dihaloalkoxybenzyl group;
$R_7$ is H or a lower alkyl group;
$R_8$ is H or a lower alkyl group;
$R_9$ is H or a lower alkyl group;
$R_{10}$ is H or a lower alkyl group;
X is O, NH or alkylamino; and
Y is O, NH or alkylamino; together with a pharmaceutically acceptable carrier. In a preferred embodiment of the present invention, the pharmaceutical composition further comprises at least one additional anti-neoplastic agent.

The present invention also provides a method for inhibiting the proliferation of a mammalian cell comprising contacting the mammalian cell with a cryptophycin compound in an amount sufficient to inhibit the proliferation of the cell, the cryptophycin compound having the following structure:

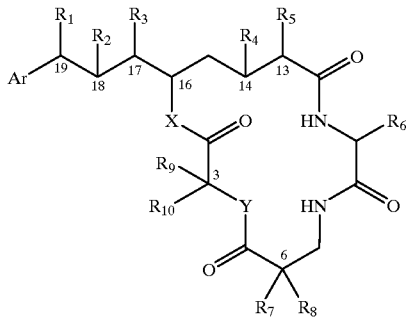

wherein
Ar is phenyl or any simple unsubstituted or substituted aromatic or heteroaromatic group;
$R_1$ is a halogen, SH, amino, monoalkylamino, dialkylamino, trialkylammonium, alkylthio, dialkylsufonium, sulfate, or phosphate;
$R_2$ is OH or SH; or
$R_1$ and $R_2$ may be taken together to form an epoxide ring, an aziridene ring, an episulfide ring, a sulfate ring or a monoalkylphosphate ring; or
$R_1$ and $R_2$ may be taken together to form a second bond between $C_{18}$ and $C_{19}$;
$R_3$ is a lower alkyl group;
$R_4$ is H;
$R_5$ is H;
$R_4$ and $R_5$ may be taken together to form a second bond between $C_{13}$ and $C_{14}$;
$R_6$ is a benzyl, hydroxybenzyl, alkoxybenzyl, halohydroxybenzyl, dihalohydroxybenzyl, haloalkoxybenzyl, or dihaloalkoxybenzyl group;
$R_7$ is H or a lower alkyl group;
$R_8$ is H or a lower alkyl group;
$R_9$ is H or a lower alkyl group;
$R_{10}$ is H or a lower alkyl group;
X is O, NH or alkylamino; and
Y is O, NH or alkylamino. In a preferred embodiment of the present invention, this method further comprises contacting the cell with at least one additional anti-neoplastic agent. In a preferred embodiment of the present invention, the mammalian cell contacted is hyperproliferative. In a further preferred embodiment of the present invention, the hyperproliferative cell is human.

The present invention also provides a method of inhibiting the proliferation of a hyperproliferative mammalian cell having a multiple drug resistant phenotype comprising contacting the cell with an amount of a cryptophycin compound effective to disrupt the dynamic state of microtubule polymerization and depolymerization to arrest cell mitosis, thereby inhibiting the proliferation of the cell, the cryptophycin compound having the following structure:

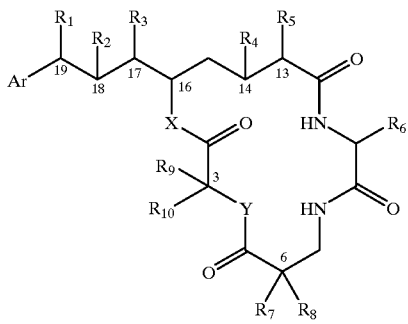

wherein

Ar is phenyl or any simple unsubstituted or substituted aromatic or heteroaromatic group;

$R_1$ is a halogen, SH, amino, monoalkylamino, dialkylamino, trialkylammonium, alkylthio, dialkylsulfonium, sulfate, or phosphate;

$R_2$ is OH or SH; or $R_1$ and $R_2$ may be taken together to form an epoxide ring, an aziridene ring, an episulfide ring, a sulfate ring or a monoalkylphosphate ring; or $R_1$ and $R_2$ may be taken together to form a second bond between $C_{18}$ and $C_{19}$;

$R_3$ is a lower alkyl group;

$R_4$ is H;

$R_5$ is H;

$R_4$ and $R_5$ may be taken together to form a second bond between $C_{13}$ and $C_{14}$;

$R_6$ is a benzyl, hydroxybenzyl, alkoxybenzyl, halohydroxybenzyl, dihalohydroxybenzyl, haloalkoxybenzyl, or dihaloalkoxybenzyl group;

$R_7$ is H or a lower alkyl group;

$R_8$ is H or a lower alkyl group;

$R_9$ is H or a lower alkyl group;

$R_{10}$ is H or a lower alkyl group;

X is O, NH or alkylamino; and

Y is O, NH or alkylamino. In a preferred embodiment of the present invention, the method further comprises contacting the cell with at least one additional anti-neoplastic agent. In a further preferred embodiment of the present invention, the mammalian cell is human.

The present invention also provides a method of alleviating a pathological condition caused by hyperproliferating mammalian cells comprising administering to a subject an effective amount of the pharmaceutical composition disclosed herein to inhibit proliferation of the cells. In a preferred embodiment of the present invention, the mammalian cells are human. In preferred embodiment of the present invention, the method further comprises administering to the subject at least one additional therapy directed to alleviating the pathological condition. In a preferred embodiment of the present invention, the pathological condition is characterized by the formation of neoplasms. In a further preferred embodiment of the present invention, the neoplasms are selected from the group consisting of mammory, small-cell lung, non-small-cell lung, colorectal, leukemia, melanoma, pancreatic adenocarcinoma, central nervous system (CNS), ovarian, prostate, sarcoma of soft tissue or bone, head and neck, gastric which includes pancreatic and esophageal, stomach, myeloma, bladder, renal, neuroendocrine which includes thyroid and non-Hodgkin's disease and Hodgkin's disease neoplasms.

The method for preparing the cryptophycin compounds is summarized in Scheme 1. The starting material is a 3E-alkene (a) substituted at C-2 with a XH group in the S-configuration where X is oxygen or NH. L-Alanine and L-lactic acid serve as inexpensive sources of the starting material a. The key step in the synthesis is a stereoselective [2,3] Wittig rearrangement (D. J.-S. Tsai et al., *J. Org. Chem.* 1984, 49, 1842–3; K. Mikami et al., *Tetrahedron* 1984, 25, 2303–2308; N. Sayo et al., *Chem Lett.* 1984, 259–62) of the propargyl ether of a (b) to the (3R,4R)-3-(XH-substituted)-4-alkylhept-5(E)-en-1-yne (c) where X is an oxygen or a protected nitrogen (e.g. t-butyldimethylsilylamino). Compound c can then be converted to the d-hydroxy or amino acid unit A precursor of the cryptophycin, methyl (5S,6R)-5-(XP-substituted)-6-alkyl-8-aryl-octa-2E,7E-die noate (d) where P is a suitable protecting group, using methods known to those of ordinary skill in the art.

One strategy for synthesizing a cryptophycin, which is composed of a d-hydroxy or amino acid unit A, an a-amino acid unit B, a b-amino acid unit C, and an a-hydroxy or amino acid unit D, is to assemble the macrocycle from two precursors representing moieties of the cryptophycin molecule, for example, an A-B precursor (e) containing the d-hydroxy or amino acid unit A and the a-amino acid unit B and a C-D precursor (f) containing the b-amino acid unit C and the a-hydroxy or amino acid unit D.

In the method described herein, a cryptophycin is assembled from A-B and C-D precursors in two steps by (1) connecting the termini of units A and D in the A-B and C-D precursors to form an acyclic C-D-A-B intermediate and (2) connecting the termini of units B and C to form the cyclic product.

In the synthesis of Cryptophycin 51 described in the Experimental Section, an ester linkage is formed between the d-hydroxy group of unit A in the A-B moiety and the carboxylic acid group of unit D in the C-D fragment to form an acyclic C-D-A-B intermediate and then an amide linkage is formed between the carboxylic acid group of unit B in the A-B moiety and the b-amino group of unit C in the C-D moiety. Compound K is the A-B moiety precursor, Compound P is the C-D moiety precursor, and Compound R is the acyclic C-D-A-B precursor of Cryptophycin 51. Compounds K and P have protecting groups on the carboxylic acid group of unit B and the b-amino group of unit C to limit coupling to ester formation between units A and D in step 1. These protecting groups are removed from the C-D-A-B intermediate so that amide formation can occur between units B and C in step 2.

The synthesis of methyl (5S,6R)-5-t-butyldimethylsilyloxy-6-methyl-8-phenyl-oc ta-2E,7E-dienoate (G), the unit A precursor of the Cryptophycin 51, is summarized in Scheme 1. (S)-trans-3-penten-2-ol (A), the starting material, was prepared by enzymatic resolution of the racemic compound. Reaction of A with propargyl chloride and base under phase-transfer condition formed propargyl ether B in 86% yield. Treatment of B with butyl lithium at −90° C. led to alcohol C in 71% yield. The desired 3R,4R anti compound C was the only product formed in the Wittig rearrangement. After protection of the hydroxyl group of C as the tert-butyldimethylsilyl ether (or tert-butyldimethylsilyl ether), hydroboration of the triple bond (H. C. Brown, Organic Synthesis Via Boranes, Wiley, 1975) led to an aldehyde D in 73% yield from C. Next D was converted into the trans a,b-unsaturated ester E by a Horner-Emmons reaction in 90% yield. Selective ozonolysis of the C6–C7 double bond in D gave alkehyde F in 83% yield. Finally a Wittig reaction of F with benzyltriphenylphosphonium chloride in the presence of butyllithium produced G in 80% yield. The overall yield of G from A was 26%.

The coupling of the unit A precursor G with the D-3-(3-chloro-4-methoxyphenyl)alanine unit B to produce the A-B precursor (K) is summarized in Scheme 2. Hydrolysis of the methyl ester group in G with lithium hydroxide in acetone produced carboxylic acid H in 95% yield. Coupling of H with trichloroethyl ester I to produce J could be accomplished in 65% yield by treating a solution of H in N,N-dimethylformamide (DMF) with a small excess of pentafluorophenyldiphenylphosphinate (FDPP), an equimolar quantity of the trifluoroacetate salt of I, followed by 3 equiv of diisopropylethylamine (DIEA) at 25° C. (S. Chen et al., *Tetrahedron Lett.* 1991, 32, 6711–4). Fluorodesilylation of J then led to K in 95% yield.

Protected amino acid I was prepared from D-tyrosine in five steps. First, D-tyrosine was chlorinated with sulfuryl chloride in glacial acetic acid (R. Zeynek, *Hoppe-Seyler's Z. f. Physiol. Chemie* 1926, 144, 247–254). Next N-(tert-butoxycarbonyl)-3-(3-chloro-4-hydroxyphenyl)-D-a lanine was obtained in 94% yield by treating a suspension of the amino acid in 50% aqueous dioxane with di-tert-butyldicarbonate in the presence of triethylamine. The resulting product was dimethylated with dimethyl sulfate in the presence of potassium carbonate in refluxing acetone in 84% yield. The methyl ester was then saponified with sodium hydroxide in aqueous dioxane to yield N-(tert-butoxycarbonyl)-3-(3-chloro-4-methoxyphenyl)-D-a lanine in 86% yield. Exposure of the BOC-protected amino acid to trichloroethanol, pyridine and DCC in dichloromethane led to trichloroethyl ester I in 65% yield. Treatment of this material with trifluoroacetic acid led to a quantitative yield of the trifluoroacetate salt of I.

The synthesis of (2S)-2-[3'(tert-butoxycarbonyl)amino-2', 2'-dimethylpropa noyloxy]-4-methylpentanoic acid (P), the C-D precursor, is summarized in Scheme 3. The starting point for the unit C portion of P was the aminoalcohol L. Protection of the amino group in L by treatment with di-tert-butyldicarbonate in the presence of triethylamine (93% yield), followed by oxidation of the primary alcohol with ruthenium tetroxide (p. H. J. Carlsen et al., *J. Org. Chem.* 1981, 46, 3936–8) gave carboxylic acid M (66% yield). L-Leucic acid was converted to allyl ester N in 93% yield under phase-transfer conditions, by exposing it to a mixture of allyl bromide in dichloromethane and aqueous sodium bicarbonate containing tetra-n-butylammonium chloride (S. Friedrich-Bochnitschek et al., *J. Org. Chem.* 1989, 54, 751–6). The coupling reaction of M with N was carried out with 4-dimethylaminopyridine (DMAP) and dicyclohexylcarbodiimide (DCC) in dichloromethane to produce O in 75% yield. Cleavage of the allyl ester in O was carried out in THF containing morpholine and catalytic tetrakis(triphenylphosphine)-palladium to give P in 95% yield (P. D. Jeffrey et al., *J. Org. Chem.* 1982, 47, 587–90).

Coupling of the A-B precursor (K) and the C-D precursor (P) was accomplished as shown in Scheme 4. Treatment of K and P with DCC/DMAP in dichloromethane led to the fully protected C-D-A-B intermediate (Q) in 84% yield. Reductive cleavage of the trichloroethyl ester group in Q was achieved using activated zinc dust in acetic acid. The BOC-protecting group was then removed by trifluoroacetic acid to give R as the trifluoroacetate salt in 91% overall yield from Q. Macrolactamization of R with FDPP led to Cryptophycin 51 in 61% yield (J. Dudash, Jr. et al., *Synth. Commun.* 1993, 23, 349–56). The overall yield from S-trans-3-penten-2-ol (A) was 7%.

Cryptophycin 51 served as the precursor of Cryptophycin 52, the R,R-epoxide, and Cryptophycin 53, the S,S-epoxide. In turn, Cryptophycin 52 served as the precursor of Cryptophycin 55, the 18R,19S-chlorohydrin, and Cryptophycin 57, the 13,14-dihydro analog. Cryptophycin 57 served as the precursor of Cryptophycin 58.

The novel cryptophycin compounds of the present invention are more stable towards hydrolysis and solvolysis than Cryptophycins 1 and 21. The ester bond connecting units C and D in Cryptophycin 1 is relatively sensitive to mild base hydrolysis, cleaving at pH 11 to a hydroxy acid with a half-life of 0.83 hour. The C-D ester bond in Cryptophycin 21, which lacks the methyl group on C-2 of unit C, opens at a faster rate with a half-life of 0.25 hour. The C-D ester bond is also sensitive to solvolysis. When methanol is used in the isolation scheme, considerable methanolysis of Cryptophycins 1 and 21. Cryptophycin 21 is much more susceptible to methanolysis than Cryptophycin 1. Cryptophycin 1 shows antitumor activity whereas Cryptophycin 21 is inactive, probably because the C-D ester bond of Cryptophycin 21 is hydrolyzed faster than the C-D ester bond of Cryptophycin 1 in vivo. Hydrolysis of the C-D ester bond may also explain in part the diminished in vivo activity of Cryptophycin 1 by intraperitoneal and subcutaneous routes of drug administration. The C-D ester bond of cryptophycins possessing two methyl groups on C-2 of unit C, such as the one found in Cryptophycin 52, is stable at pH 11.

The novel cryptophycin compounds of the present invention and the previously disclosed cryptophycin compounds can be therapeutically employed as anti-neoplastic agents and thereby used in methods to treat neoplastic diseases. As used herein, "neoplastic" pertains to a neoplasm, which is an abnormal growth, such growth occurring because of a proliferation of cells not subject to the usual limitations of growth. As used herein, "anti-neoplastic agent" is any compound, composition, admixture, co-mixture or blend which inhibits, eliminates, retards or reverses the neoplastic phenotype of a cell.

Chemotherapy, surgery, radiation therapy, therapy with biologic response modifiers, and immunotherapy are currently used in the treatment of cancer. Each mode of therapy has specific indications which are known to those of ordinary skill in the art, and one or all may be employed in an attempt to achieve total destruction of neoplastic cells. Chemotherapy utilizing one or more cryptophycins is provided by the present invention. Moreover, combination chemotherapy, chemotherapy utilizing cryptophycins in combination with other neoplastic agents, is also provided by the subject invention as combination therapy is generally more effective than the use of single anti-neoplastic agents. Thus, a further aspect of the present invention provides compositions containing a therapeutically effective amount of at least one new cryptophycin compound of the present invention, including nontoxic addition salts thereof, which serve to provide the above-recited therapeutic benefits. Such compositions can also be provided together with physiologically tolerable liquid, gel or solid carriers, diluents, adjuvants and excipients. Such carriers, diluents, adjuvants and excipients may be found in the *United States Pharmacopeia Vol. XXII and National Formulary Vol XVII*, U.S. Pharmacopeis Convention, Inc., Rockville, Md. (1989), the contents of which are herein incorporated by reference. Additional modes of treatment are provided in *AHFS Drug Information*, 1993 ed. by the American Hospital formulary Service, pp. 522–660, the contents of which are herein incorporated by reference.

The present invention further provides that the pharmaceutical composition used to treat neoplastic disease contains at least one cryptophycin compound and at least one additional anti-neoplastic agent. Anti-neoplastic compounds which may be utilized in combination with cryptophycin include those provided in *The Merck Index,* 11th ed. Merck & Co., Inc. (1989) pp. Ther 16–17, the contents of which are hereby incorporated by reference. In a further embodiment of the invention, anti-neoplastic agents may be antimetabolites which may include, but are not limited to, methotrexate, 5-fluorouracil, 6-mercaptopurine, cytosine arabinoside, hydroxyurea, and 2-chlorodeoxyadenosine. In another embodiment of the present invention, the anti-neoplastic agents contemplated are alkylating agents which may include, but are not limited to, cyclophosphamide, melphalan, busulfan, paraplatin, chlorambucil, and nitrogen mustard. In a further embodiment of the subject invention, the anti-neoplastic agents are plant alkaloids which may include, but are not limited to, vincristine, vinblastine, taxol, and etoposide. In a further embodiment of the present invention, the anti-neoplastic agents contemplated are antibiotics which may include, but are not limited to, doxorubicin (adriamycin), daunorubicin, mitomycin c, and bleomycin. In a further embodiment of the subject invention, the anti-neoplastic agents contemplated are hormones which may include, but are not limited to, calusterone, diomostavolone, propionate, epitiostanol, mepitiostane, testolactone, tamoxifen, polyestradiol phosphate, megesterol acetate, flutamide, nilutamide, and trilotane. In a further embodiment of the subject invention, the anti-neoplastic agents contemplated include enzymes which may include, but are not limited to, L-Asparaginase or aminoacridine derivatives which may include, but are not limited to, amsacrine. Additional anti-neoplastic agents include those provided in Skeel, Roland T., "Antineoplastic Drugs and Biologic Response Modifier: Classification, Use and Toxicity of Clinically Useful Agents," *Handbook of Cancer Chemotherapy* (3rd ed.), Little Brown & Co. (1991), the contents of which are herein incorporated by reference.

These compounds and compositions can be administered to mammals for veterinary use, such as for domestic animals, and clinical use in humans in a manner similar to other therapeutic agents. In general, the dosage required for therapeutic efficacy will vary according to the type of use and mode of administration, as well as the particularized requirements of individual hosts. Ordinarily, dosages will range from about 0.001 to 1000 mg/kg, more usually 0.01 to 10 mg/kg, of the host body weight. Alternatively, dosages within these ranges can be administered by constant infusion over an extended period of time, usually exceeding 24 hours, until the desired therapeutic benefits have been obtained. Indeed, drug dosage, as well as route of administration, must be selected on the basis of relative effectiveness, relative toxicity, growth characteristics of tumor and effect of cryptophycins on cell cycle, drug pharmacokinetics, age, sex, physical condition of the patient, and prior treatment.

The cryptophycin compounds, with or without additional anti-neoplastic agents, may be formulated into therapeutic compositions as natural or salt forms. Pharmaceutically acceptable non-toxic salts include the base addition salts (formed with free carboxyl or other anionic groups) which may be derived from inorganic bases such as, for example, sodium, potassium, ammonium, calcium, or ferric hydroxides, and such organic bases as isopropylamine, trimethylamine, 2-ethylamino ethanol, histidine, procaine, and the like. Such salts may also be formed as acid addition salts with any free cationic groups and will generally be formed with inorganic acids such as, for example, hydrochloric or phosphoric acids, or organic acids such as acetic, oxalic, tartaric, mandelic, and the like. Additional excipients which the further invention provides are those available to one of ordinary skill in the art, for example, that found in the *United States Pharmacopeia Vol. XXII and National Formulary Vol XVII,* U.S. Pharmacopeis Convention, Inc., Rockville, Md. (1989), which is herein incorporated by reference.

The suitability of particular carriers for inclusion in a given therapeutic composition depends on the preferred route of administration. For example, anti-neoplastic compositions may be formulated for oral administration. Such compositions are typically prepared either as liquid solution or suspensions, or in solid forms. Oral formulations usually include such normally employed additives such as binders, fillers, carriers, preservatives, stabilizing agents, emulsifiers, buffers and excipients as, for example, pharmaceutical grades of mannitol, lactose, starch, magnesium stearate, sodium saccharin, cellulose, magnesium carbonate, and the like. These compositions take the form of solutions, suspensions, tablets, pills, capsules, sustained release formulations, or powders, and typically contain 1%–95% of active ingredient, preferably 2%–70%.

Compositions of the present invention may also be prepared as injectable, either as liquid solutions, suspensions, or emulsions; solid forms suitable for solution in, or suspension in, liquid prior to injection may be prepared. Such injectables may be administered subcutaneously, intravenously, intraperitoneally, intramuscularly, intrathecally, or intrapleurally. The active ingredient or ingredients are often mixed with diluents or excipients which are physiologically tolerable and compatible with the active ingredient(s). Suitable diluents and excipients are, for example, water, saline, dextrose, glycerol, or the like, and combinations thereof. In addition, if desired, the compositions may contain minor amounts of auxiliary substances such as wetting or emulsifying agents, stabilizing or pH buffering agents.

The invention further provides methods for using cryptophycin compounds encompassed by the genus structure to inhibit the proliferation of mammalian cells by contacting these cells with a cryptophycin compound in an amount sufficient to inhibit the proliferation of the mammalian cell. A preferred embodiment is a method to inhibit the proliferation of hyperproliferative mammalian cells. For purposes of this invention, "hyperproliferative mammalian cells" are mammalian cells which are not subject to the characteristic limitations of growth, e.g., programmed cell death (apoptosis). A further preferred embodiment is when the mammalian cell is human. The invention further provides contacting the mammalian cell with at least one cryptophycin compound and at least one additional anti-neoplastic agent. The types of anti-neoplastic agents contemplated are the same as those disclosed hereinabove.

The invention further provides methods for using cryptophycin compounds encompassed by the genus structure to inhibit the proliferation of hyperproliferative cells with drug-resistant phenotypes, including those with multiple drug-resistant phenotypes, by contacting said cell with a cryptophycin compound in an amount sufficient to inhibit the proliferation of a hyperproliferative mammalian cell. A preferred embodiment is when the mammalian cell is human. The invention further provides contacting the mammalian cell with a cryptophycin compound and at least one additional anti-neoplastic agent. The types of anti-neoplastic agents contemplated are the same as those disclosed hereinabove.

The invention further provides a method for alleviating pathological conditions caused by hyperproliferating mammalian cells, for example, neoplasia, by administering to a subject an effective amount of a pharmaceutical composition provided hereinabove to inhibit the proliferation of the hyperproliferating cells. As used herein "pathological condition" refers to any pathology arising from the proliferation of mammalian cells that are not subject to the normal limitations of cell growth. Such proliferation of cells may be due to neoplasms, including, but not limited to the following neoplasms: mammary, small-cell lung, non-small-cell lung, colorectal, leukemia, melanoma, central nervous system (CNS), ovarian, prostate, sarcoma of soft tissue or bone, head and neck, gastric which includes pancreatic and esophageal, stomach, myeloma, bladder, renal, neuroendocrine which includes thyroid and lymphoma, non-Hodgkin's and Hodgkin's. In a further embodiment of the invention, the neoplastic cells are human. The present invention further provides methods of alleviating such pathological conditions utilizing cryptophycin in combination with other therapies, as well as other anti-neoplastic agents. Such therapies and their appropriateness for different neoplasia may be found in *Cancer Principles and Practice of Oncology*, 4th ed., editors DeVita, V., Hellman, S., and Rosenberg., S., Lippincott Co. (1993), the contents of which are herein incorporated by reference.

In the present disclosure, cryptophycin compounds are shown to potently disrupt the microtubule structure in cultured cells. In addition, and in contrast with the Vinca alkaloids, cryptophycin compounds appear to be a poor substrate for the drug-efflux pump P-glycoprotein. Cryptophycin 1 is the major cytotoxin in the blue-green alga (cyanobacteria) Nostoc sp. strain designated GSV 224 and shows excellent activity against tumors implanted in mice. This cyclic didepsipeptide had previously been isolated from Nostoc sp. ATCC accession no. 53787 as an antifungal agent and its gross structure was previously determined. The relative and absolute stereochemistry of this potentially important drug has now been established using a combination of chemical and spectral techniques. Twenty-four additional cryptophycin compounds, Cryptophycins 2–7, 16–19, 21, 23, 24, 26, 28–31, 40, 43, 45, 49, 50 and 54 have also been isolated from GSV 224 and their total structures and cytotoxicities determined. Several derivatives and degradation products are described, both chemically and pharmacologically.

The following examples serve to illustrate certain preferred embodiments and aspects of the present invention and are not to be construed as limiting the scope thereof.

Experimental Section

In the experimental disclosure which follows, all weights are given in grams (g), milligrams (mg), micrograms (mg), nanograms (ng), picograms (pg) or moles (mol), all concentrations are given as percent by volume (%), molar (M), millimolar (mM), micromolar ($\mu$M), nanomolar (nM), or picomolar (pM), normal (N) and all volumes are given in liters (L), milliliters (mL) or microliters ($\mu$L), and measures in millimeters (mm), unless otherwise indicated.

The following examples demonstrate the isolation and synthesis of cryptophycin compounds as well as their use as therapeutic agents in accordance with the invention.

In screening extracts of over 1000 blue-green algae (cyanobacteria) for antitumor activity, the lipophilic extract of Nostoc sp. GSV 224 was found to be strongly cytotoxic,[3] exhibiting minimum inhibitory concentrations (MICs) of 0.24 ng/mL against KB, a human nasopharyngeal carcinoma cell line, and 6 ng/mL against LoVo, a human colorectal adenocarcinoma cell line. More importantly, this extract showed significant tumor selective cytotoxicity in the Corbett assay.[4,5] Bioassay monitored reversed-phase chromatography of the algal extract led to a fraction which was predominantly Cryptophycin 1, a potent fungicide that had been isolated earlier from Nostoc sp. ATCC 53789 by researchers at Merck[6,7] and found to be very active against strains of Cryptococcus.

Cryptophycin 1 accounted for most of the cytotoxic activity of the crude algal extract of Nostoc sp. GSV 224 and the pure compound showed $IC_{50}$ values of 3 and 5 pg/mL against KB and LoVo, respectively. In the Corbett assay Cryptophycin 1 was found to be strongly tumor selective and equally cytotoxic against drug-sensitive and drug-resistant tumor cells. Immunofluorescence assays showed that Cryptophycin 1 interact with a cellular target similar to that of vinblastine, but differed from the latter drug in having a longer time course of action and in not forming paracrystalline bodies. In preliminary in vivo experiments, Cryptophycin 1 exhibited very promising activity against tumors implanted in mice.

Minor amounts of several other cryptophycin compounds were present in Nostoc sp. GSV 224. Twenty-one of these could be isolated in sufficient quantities for structure determinations and antitumor evaluation in vitro by extraction of the alga with 1:5 dichloromethane/acetonitrile and reversed-phase HPLC of the extract. Cryptophycins 2, 3, 4, 16, 17, 18, 19, 21, 23, 24, 26, 28, 29, 30, 31, 40, 43, 45, 49, 50 and 54 accompanied Cryptophycin 1 in the fraction eluted from a reversed-phase flash column with 65:35 acetonitrile/water. Cryptophycins 2, 3, 4, 5, 6, and 7 were the only compounds found when the alga was extracted with methanol and the reversed-phase chromatography was carried out with methanol/water. Cryptophycins 2, 3, 4, 5 and 6 were eluted with 3:1 methanol/water and Cryptophycin 7 was found in an earlier, less cytotoxic fraction eluted with 1:3 methanol/water. Acyclic Cryptophycins 5, 6 and 7 appear to be artifacts generated by decomposition of Cryptophycin 1 during the isolation procedure.

Cryptophycins 3 and 5 appeared to be identical with fungicidal semi-synthetic compounds prepared from Cryptophycin 1 by researchers at Merck.[8,9] Cryptophycin 3 was prepared by treating Cryptophycin 1 with a zinc-copper couple or with diphosphorus tetraiodide.[8] Cryptophycin 5 was prepared by methanolysis of Cryptophycin 1.[9]

EXAMPLE 1

Structure Determination

The determination of the structures of the new compounds, viz. Cryptophycins 2, 4, 6, 7, 8, 9, 10, 12, 14, 16, 17, 18, 19, 21, 23, 24, 26, 28, 29, 30, 31, 40, 43, 45, 49, 50 and 54, as well as those previously disclosed, were carried out in a straightforward manner using methodology that is well-known to those trained in the art. Mass spectral data were consistent with the molecular compositions. Proton and carbon NMR data obtained from COSY, HMQC, HMBC and NOESY spectra allowed one to assemble all of the gross structures of these depsipeptide-type compounds. The presence of the various hydroxy and amino acid units in each compound were confirmed by gas chromatographic mass spectral analysis. Total structures, including absolute stereochemistries, were determined using a combination of chemical degradative and special analytical techniques on appropriate derivatives of the cryptophycin compounds.

EXAMPLE 2

Structure-Activity Relationships (SAR)

To probe the structural features in Cryptophycin 1 needed for optimal activity, all of the compounds described herein were evaluated for cytotoxicity against KB (human nasopharyngeal carcinoma), LoVo (human colon carcinoma), and SKOV3 (human ovarian carcinoma) cell lines. $IC_{50}$ values are listed in Tables 1 and 2. Comparison of the cytotoxicities show that the intact macrolide ring, the epoxy and methyl groups and the double bond in the 7,8-epoxy-5-hydroxy-6-methyl-8-phenyl-2-octenoic acid unit (see Unit A in FIG. 1), the chloro and O-methyl groups in the 3-(3-chloro-4-methoxyphenyl)alanine unit (Unit B), the methyl group in the 3-amino-2-methylpropionic acid unit (Unit C), and the isobutyl group in the leucic acid unit (Unit D) of Cryptophycin 1 are needed for optimal cytotoxicity. The potent cytotoxicity of Cryptophycin 8 is most likely due to the chlorohydrin functionality which acts as a masked epoxide.

The most active compounds were also evaluated for selective cytotoxicity against four different cell types, viz. a murine leukemia (L1210 or P388), a murine solid tumor (colon adenocarcinoma 38, pancreatic ductal adenocarcinoma 03, mammary adenocarcinoma M16/M17), a human solid tumor (colon CX-1, HCT8, H116; lung H125; mammary MX-1, MCF-7), and a low malignancy fibroblast (LML), using the Corbett assay,2 a disk diffusion assay modeled after the one commonly used in antifungal and antibacterial testing. The results, shown in Table 1, indicated that Cryptophycins 1–5 and 8 were neither solid tumor nor leukemia selective, but rather equally active against tumor cell lines, including drug-resistant ones such as M17. None of the compounds showed a zone of inhibition for any of the solid tumor cell lines that was $^3$250 zone units, i.e. $^3$7.5 mm, larger than the zone of inhibition for the leukemia cell line. Cryptophycins 1–5 and 8, however, displayed markedly larger zones of inhibition ($^3$400 zone units) for all of the tumor cell lines compared with the zone of inhibition for the fibroblast LML. Diagnostically LML has been found to behave more like a normal cell than a tumor cell with respect to clinically-useful cytotoxic agents (see Corbett assay data for 5-fluorouracil, etoposide and taxol in Table 1). Since the differential cytotoxicities were >250 zone units, Cryptophycins 1–5 and 8 were tumor selective. These compounds therefore became candidates for in vivo testing.

Cryptophycin 1 is active against a broad spectrum of murine and human tumors implanted in mice, including drug-resistant ones (Table 3). It exhibits excellent activity against five early stage murine tumors, viz. colon adenocarcinomas #38 and #51, taxol-sensitive and taxol-resistant mammary #16/C/RP, and pancreatic ductal adenocarcinoma #03, and two early stage human tumors tested in SCID mice, viz. MX-1 breast and H125 adenosquamous lung, showing tumor burden T/C (mean tumor burden in treated animals/ mean tumor burden untreated animals) values that are less than 10%.

T/C values that are less than 42% are considered to be active by NCI standards; T/C values that are less than 10% are considered to have excellent activity and potential clinical activity by NCI standards.[9] Two of the trials showed gross (tumor cell) log kill values of 2.0. Gross log kill is defined as T-C/3.2 Td where T is the median time in days for the tumors of the treated group to reach 750 mg, C is the median time in days for the tumors of the control group to reach 750 mg, and Td is the tumor volume doubling time. Gross log kill values of >2.8, 2.0–2.8, 1.3–1.9, 0.5–0.8, and <0.5 with duration of drug treatment of 5–20 days are scored ++++, +++, ++, + and–(inactive), respectively. An activity rating of +++ to ++++, which is indicative of clinical activity, is needed to effect partial or complete regression of 100–300 mg size masses of most transplanted solid tumors of mice.

Cryptophycin 8 is also active against a broad spectrum of tumors implanted in mice (Table 4). It has shown excellent activity against all of the tumors tested to date, showing tumor burden T/C values <10%, but more importantly gross log kill activity ratings of +++ to ++++ and some cures.

Good in vivo activity was also seen with Cryptophycin 35 in the one trial that has been run to date.

Lethal toxicity observed during testing of Cryptophycins 1 and 8 was attributed to leucopenia which is common to all clinically used antitumor drugs.

TABLE 1

Cytotoxicity data for cryptophycins and semi-synthetic analogs Corbett/Valeriote assay data for 5-fluorouracil, etoposide (VP-16) and taxol are included for comparison Type of Cytotoxicity (Differential in Zone Units)

| Compound | µg/disk | Corbett Assay[a] | µg/disk | Valeriote Assay[b] | KB $IC_{50}$ ng/mL | LoVo $IC_{50}$ ng/mL |
|---|---|---|---|---|---|---|
| 1 | 12.5 | E/T (>400)[c] | | N | 0.005 | 0.003 |
| 2 | 25 | E/T (>400)[c] | | N | 0.007 | 0.0002 |
| 3 | 25 | E/T (>400)[c] | | N | 0.3 | 0.5 |

TABLE 1-continued

Cytotoxicity data for cryptophycins and semi-synthetic analogs
Corbett/Valeriote assay data for 5-fluorouracil,
etoposide (VP-16) and taxol are included for comparison Type of Cytotoxicity (Differential in Zone Units)

| Compound | µg/disk | Corbett Assay[a] | µg/disk | Valeriote Assay[b] | KB $IC_{50}$ ng/mL | LoVo $IC_{50}$ ng/mL |
|---|---|---|---|---|---|---|
| 4 | 20 | E/T (>400)[c] | | N | 1.3 | 0.5 |
| 5 | 2.9 | E/T (>600)[c] | | N | 0.02 | 0.02 |
| 6 | 250 | I | | | ≧100 | ≧100 |
| 7 | | | | | ≧750 | ≧480 |
| 8 | 30 | E/T (>500)[c] | 30 | N | 0.0002 | 0.01 |
| 9 | | | | | 15 | Not Determined |
| 10 | | | | | ≧100 | ≧100 |
| 12 | | | | | ≧100 | ≧100 |
| 14 | | | | | 1.8 | 3 |
| 5-FU | 2.5 | M/T (>400)[d] | 2.5 | LL (>400) | | |
| VP-16 | 5 | L (350), T (530)[d] | 5 | LL (260) | | |
| taxol | 0.2 | M/H/T (≧400)[d] | | | | |

[a]L = leukemia selective (e.g. $Z_{L1210} - Z_{C38}$ and $Z_{L1210} - Z_{H8} \geq 250$ zu)
M = murine solid tumor selective (e.g. $Z_{C38} - Z_{L1210} \geq 250$ zu)
H = human solid selective (e.g. $Z_{H8} - Z_{L1210} \geq 250$ zu)
E = equally cytotoxic towards leukemia and solid tumor cell lines (inhibition zones ≧ 250 zu)
T = tumor selective (e.g. $Z_{L1210} - Z_{LML}$, $Z_{C38} - Z_{LML}$, and $Z_{H8} - Z_{LML} \geq 250$ zu
I = inactive (inhibition zones <250)
[b]N = non-selective towards tumor (leukemia) and normal cell (CFU-GM) lines
LL = lymphocytic leukemia selective ($Z_{L1210} - Z_{CFU-GM} \geq 250$ zu)
ML = acute myelogenous leukemia (AML) selective ($Z_{AML} - Z_{CFU-GM} \geq 250$ zu).
[c]Selective against drug-sensitive and drug-resistant cell lines ($Z_{C38} - Z_{LML}$, $Z_{M17} - Z_{LML}$ and $Z_{H8} - Z_{LML}$).
[d]Selective against drug-sensitive cell lines only.

TABLE 2

In Vitro Cytotoxicity Data of Cryptophycins

| Cryptophycin | $KBIC_{50}$ ng/mL | $LoVOIC_{50}$ ng/mL | $SKOV3IC_{50}$ ng/mL |
|---|---|---|---|
| 1 | 0.0025 | 0.001 | 0.026 |
| 2 | 0.023 | 0.021 | 0.18 |
| 3 | 1.8 | 0.6 | 2.8 |
| 4 | 6 | 2.5 | 21 |
| 5 | 12 | 2 | 7.4 |
| 8 | 0.01 | 0.0022 | 0.15 |
| 12 | 18 | 3 | |
| 15 | | | 12 |
| 16 | 0.08 | 0.02 | 0.64 |
| 17 | 4.7 | 5.9 | 11 |
| 18 | 15 | 4.5 | 23 |
| 19 | 9.8 | 5.9 | 41 |
| 21 | 0.01 | 0.0003 | 0.029 |
| 23 | 0.89 | 0.4 | 1.7 |
| 24 | 0.12 | 0.095 | 0.3 |
| 26 | 19 | 9.8 | 95 |
| 28 | 1.5 | 0.75 | 6.1 |
| 29 | 1 | 0.49 | 3.4 |
| 30 | 11 | 8 | 21 |
| 31 | 0.53 | 0.062 | 1.9 |
| 35 | 0.055 | 0.01 | 0.092 |
| 40 | 9.0 | 1.0 | 1.7 |
| 43 | 0.72 | 0.8 | 1.1 |
| 45 | 2.3 | 2.4 | 1.6 |
| 49 | 1.4 | 1.9 | 1.1 |
| 50 | 0.17 | 0.17 | 0.2 |
| 54 | 0.80 | 2.2 | 2.2 |

TABLE 3

In Vivo Activity of Cryptophycin-A

| Exp # | SC Tumor | # of Inj. IV | mg/kg Total Dose | % Body Wt. Loss at Nadir | T/C | Log Kill | Cures |
|---|---|---|---|---|---|---|---|
| 1560 | Colon 38 | 8 | 10.3 | Gain | 6% | 1.5 | 0/5 |
| 1694 | Panc 03 | 8 | 16.0 | Gain | 0% | 2.0 | 0/5 |
| 1636 | Colon 51 | 7 | 28.1 | −11% | 7% | 1.3 | 0/5 |
| 1720 | Mam 16/C | 5 | 13.2 | −1% | 5% | 1.4 | 0/5 |
| 1733 | Mam 16/Taxol | 5 | 16.5 | 0% | 2% | 1.8 | 0/4 |
| 1833 | M17/0 (Adr. Sens.) | 5 | 5.4 | −10% | 23% | <1 | 0/5 |
| 1749 | Panc 02 | 5 | 11.0 | −5% | 20% | 1.1 | 0/5 |

TABLE 3-continued

In Vivo Activity of Cryptophycin-A

| Exp # | SC Tumor | # of Inj. IV | mg/kg Total Dose | % Body Wt. Loss at Nadir | T/C | Log Kill | Cures |
|---|---|---|---|---|---|---|---|
| 1596 | Human Sm Cell L. DMS273 SCID | 6 | 7.3 | 0% | 27% | <1 | 0/5 |
| 1806 | MX-1 Human Breast | 8 | 12 | −3% | 3% | 2.0 | 0/5 |
| 1823 | H125 Human Adenosq-lung | 8 | 14.4 | −15% 1/5 dead | 9% | 1.1 | 0/5 |
| 1841 | LNCaP Human Prostate | 6 | 6.5 | −6% | 26% | <1 | 0/5 |

TABLE 4

In Vivo Activity of Cryptophycin Analogs

| Exp # | Agent | SC Tumor | # of Inj. IV | mg/kg TD | % Body Wt. Loss at Nadir | T/C | Log Kill | Cures |
|---|---|---|---|---|---|---|---|---|
| 1813 | Cryptophycin-2 | P03 | 10 | 37 | −2% | 44% | <1 | 0/5 |
| 1843 | Cryptophycin-3 | P03 | 4 | 28/5 | −9% | 54% | <1 | 0/5 |
| 1769 | Cryptophycin-8 | C38 | 15 | 45 | −2% | >100% | None | 0/5 |
| 1825 | Cryptophycin-8 | P03 | 11 | 106 | −6% | 4% | 4.6 | 0/5 |
| 1885 | Cryptophycin-8 | Mam 16/C | 7 | 21.3 | −4.5% | 6% | 2.5 | 0/5 |
| 1887B | Cryptophycin-8 | C38 | 6 | 30 | −2% | 0% | 2.8 | 1/5 |
| 1900 | Cryptophycin-8 | Colon 51 | 9 | 67.5 | −1% | 7% | 1.8 | 0/5 |
| 1843 | Cryptophycin-15 | P03 | 5 | 18 | −7% | 83% | None | 0/5 |
| 1878 | Cryptophycin-16 | P03 | 9 | 82 | −1% | 89% | None | 0/5 |
| 1813 | Cryptophycin-21 | P03 | 9 | 27 | −11% (1/5 dead) | 61% | None | 0/5 |
| 1843 | Cryptophycin-35 | P03 | 7 | 23 | −2% | 11% | 1.3 | 0/5 |

EXAMPLE 3

Culture Conditions

Nostoc sp. GSV 224 was obtained from Professor C. P. Wolk, MSU-DOE Plant Research Laboratory, Michigan State University. Nostoc sp. ATCC 53789 was purchased from the American Type Culture Collection. A 1L flask culture of alga was used to inoculate an autoclaved 20L glass carboy containing an inorganic medium, designated modified BG-11[3], the pH of which had been adjusted to 7.0 with NaOH. Cultures were continuously illuminated at an incident intensity of 200 $\mu$mol photons $m^{-2}sec^{-1}$ (photosynthetically active radiation) from banks of cool-white fluorescent tubes and aerated at a rate of 5L/min with a mixture of 0.5% $CO_2$ in air at a temperature of 24+1° C. Typically, the culture was harvested by filtration after 21 days. The yields of lyophilized Nostoc sp. GSV 224 and ATCC 53789 averaged 0.61 and 0.3 g/L of culture, respectively.

EXAMPLE 4

Isolation

Method A

The lyophilized Nostoc sp. GSV224 (50 g) was extracted with 2 L of 1:5 $CH_2Cl_2/CH_3CN$ for 48 h and the extract concentrated in vacuo to give a dark green solid. The residue (1 g; KB MIC 0.24 ng/mL) was applied to an ODS-coated silica column (55 g, 7×5 cm) and subjected to flash chromatography with 1:3 $CH_3CN/H_2O$ (0.8 L), 1:1 $CH_3CN/H_2O$ (0.8 L), 65:35 $CH_3CN/H_2O$ (1.0 L), MeOH (0.8 L), and $CH_2Cl_2$ (0.5 L). The fraction that was eluted with 65:35 $CH_3CN/H_2O$ (420 mg; KB MIC 14 pg/mL) was subjected to reversed-phase HPLC (Econosil C18, 10 $\mu$m, 25 cm×21.5 mm, UV detection at 250 nm, 65:35 $CH_3CN/H_2O$, flow rate 6 mL/min) to obtain Cryptophycin 1 (tphd R 49.3 min, 220 mg) and a number of impure fractions. The fraction eluted from the Econosil C18 column at $t_R$ 28.8 min was further purified by normal phase HPLC (Econosil silica 5 m cartridge, 250×4.6 mm, 6:4 ethyl acetate/hexane, 3 mL/min) to give Cryptophycin 16 (3.0 mg). The fraction eluted from the Econosil C18 column at $t_R$ 32.5 min was subjected to HPLC on the Econosil silica column using 55:45 ethyl acetate/hexane at 3 mL/min to give Cryptophycin 24 (0.8 mg). The fraction eluted from the Econosil C18 column at $t_R$ 35.5 min was subjected to HPLC twice on the Econosil silica column, first using 1:1 ethyl acetate/hexane at 3 mL/min and second using 4:6 ethyl acetate/methylene chloride at 2.5 mL/min to give Cryptophycin 23 (1.2 mg) and Cryptophycin 43 (0.1 mg). The fraction eluted from the Econosil C18 column at $t_R$ 39.5 min was subjected to HPLC on the Econosil silica column with 1:1 ethyl acetate/hexane at 3 mL/min to give Cryptophycin 2 (6 mg) and Cryptophycin 21 (14 mg) and a complex mixture of Cryptophycins eluted at $t_R$ 32.5 min. This latter fraction, accumulated from 400 gm dry alga, was chromatographed successively on a semi preparative column (partisil C18, 250×9.4 mm, 10 m) with 35:65 water/acetonitrile and a reversed phase analytical column (Econosil, 150×4.6 mm, 5 m) with 5:4:1 water/ acetonitrile/methanol at 1.3 mL/min to give Cryptophycin 50 ($t_R$ 34.8, 0.4 mg) and Cryptophycin 40 ($t_R$ 38.8 min, 0.3 mg). The fraction eluted from the Econosil C18 column at $t_R$ 44.5 min was subjected to HPLC on the Econosil silica column with 1:1 ethyl acetate/hexane at 3 mL/min to give Cryptophycin 17 (0.3 mg). Normal phase HPLC purification of the fraction eluted from the Econosil C18 column at $t_R$ 54.5 as a shoulder to Cryptophycin 1 yielded Cryptophycin 45 ($t_R$ 6.7 min, 0.1 mg), Cryptophycin 26 ($t_R$ 8.9 min, 0.5 mg), and Cryptophycin 54 ($t_R$ 19.8 min, <0.1 mg) on elution with 1:1 ethyl acetate/hexane. The fraction eluted from the Econosil C18 column as a broad peak ($t_R$ 58 to 70 min) was subjected to HPLC on the Econosil silica column with 43.57 ethyl acetate/hexane at 2.5 mL/min to give Cryptophycin 4 ($t_R$ 19.6 min, 1.5 mg), Cryptophycin 31 ($t_R$ 9.4 min, 0.8 mg), Cryptophycin 19 ($t_R$ 25.8 min, 0.3 mg), Cryptophycin 49 ($t_R$ 28 min, 0.1 mg), Cryptophycin 28 ($t_R$ 29.0 min, 0.5 mg) and impure Cryptophycin 29 ($t_R$ 52.5 min, 2.0 mg) and Cryptophycin 30 ($t_R$ 49 min, 3.0 mg). Cryptophycins 29 and 30 obtained pure after reversed phase HPLC (Econosil C18, 10 m, 250×10 mm, 3:1 methanol/water). The fraction eluted from the Econosil C18 column at $t_R$ 78.9 min was subjected to HPLC on the Econosil silica column with to give Cryptophycin 3 ($t_R$ 16.4 min, 3.0 mg). The fraction eluted from the Econosil C18 column at $t_R$ 82.8 min was subjected to HPLC on the Econosil silica column with 45:55 ethyl acetate/hexane at 3 mL/min to give Cryptophycin 18 ($t_R$ 19.2, 0.8 mg).

Method B

The lyophilized Nostoc sp. GSV 224 (12.23 g) was extracted twice with 700 mL and 400 mL portions of MeOH for 12 and 5 hours (h), respectively. The extracts were combined and concentrated in vacuo to give 1.84 g of a dark green solid which ws partitioned between water and $CH_2Cl_2$. The lipophilic portion (0.65 g; KB MIC 0.24 ng/mL) was applied to an ODS-coated silica column (55 g, 7×5 cm) and subjected to flash chromatography with 1:3 MeOH/$H_2O$ (0.8 L), 1:1 MeOH/$H_2O$ (0.8 L), 3:1 MeOH/$H_2O$ (0.8 L), MeOH (0.8 L), and $CH_2Cl_2$ (0.5 L). The fraction that was eluted with 3:1 MeOH/$H_2O$ (22 mg; KB MIC 14 pg/mL), which accounted for essentially all of the cytotoxic activity, was subjected to reversed-phase HPLC (Econosil C18, 10 $\mu$u, 250 cm×10 mm, UV detection at 250 nm, flow rate 3 mL/min) using 1:5 MeOH/$H_2O$ as the eluant to give Cryptophycins 7 ($t_R$ 7.6 min, 0.2 mg), 5 ($t_R$ 15.4 min, 2.3 mg), 2 ($t_R$ 16.0 min, 1.0 mg), 1 ($t_R$ 19.0 min, 12.0 mg), 4 ($t_R$ 26.5 min, 1.2 mg), and 3 ($t_R$ 30.2 min, 1.4 mg). From one of the cultures the fraction (8.1 mg) that eluted from the flash column with 1:3 MeOH/$H_2O$ showed milder cytotoxicity (KB MIC 2 $\mu$g/mL). Purification on HPLC using 2:3 MeOH/$H_2O$ as the eluant yielded cryptophycin G (7, $t_R$ 6.0 min, 2.4 mg).

EXAMPLE 5

Spectral Data for Cryptophycins 1–7

The bold italicized letters in the spectral data refer to the units A–D in FIG. 1.

Cryptophycin 1

$[\alpha]_D$+33.8°(MeOH, c 1.83); UV $\lambda_{max}(\epsilon)$ 208 (42,400), 218 (33,700), 228 (23,800), 280 (2,210); CD $[\theta]_{202}$+15,900, $[\theta]_{206}$+64,900, $[\theta]_{214}$+26,900, $[\theta]_{224}$+46,300, $[\theta]_{237}$+10,500. IR (CHCl$_3$) $\upsilon_{max}$ 3425, 2963, 1751, 1719, 1677, 1502, 1259 cm$^{-1}$. EIMS m/$\geq$ (rel intensity) 654/656 (20/9), 412/414 (33/12), 280/282 (31/12), 227 (80), 195/197 (92/44), 91 (100); high resolution EIMS n/z 654.2665 (calcd for $C_{35}H_{43}ClN_2O_8$, 4.3 mmu error). $^1$H NMR (CDCl$_3$): amino or hydroxy acid unit δ (carbon position, multiplicity; J in Hz) 7,8-epoxy-5-hydroxy-6-methyl-8-phenyl-2-octenoic acid (A) 5.74 (2, dt; 15.5 and 0.9), 6.68 (3, ddd; 15.5, 9.6 and 5.2), 2.45 (4, ddd; 14.2, 11.1 and 9.6), 2.55 (4, brdd; 14.2 and 5.2), 5.16 (5, ddd; 11.1, 4.9 and 1.9), 1.80 (6, m), 1.14 (6-Me, d; 7.1), 2.92 (7, dd; 7.5 and 2.0), 3.69 (8, d; 2.0), 7.25 (10/14, m), 7.34–7.39 (11/12/13, m); leucic acid (D) 4.83 (2, dd; 6.8 and 3.3), 1.70 (3, m), 1.36 (3, m), 1.70(4, m), 0.86 (5, d; 6.6), 0.85 (5', d;6.6); 3-amino-2-methylpropionic acid (C) 2.71 (2, m), 1.22 (2-Me, d; 7.1), 3.30 (3, ddd; 13.4, 5.8 and 3.8), 3.48 (3, ddd; 13.4, 6.3 and 5.8), 6.93 (3-NH, brt; 5.8); 3-chloro-4-methoxyphenylalanine (B) 4.80 (2, ddd; 8.7, 7.3 and 5.4), 5.61 (2-NH, d; 8.7), 3.03 (3, dd; 14.4 and 7.3), 3.13 (3, dd; 14.4 and 5.4), 7.21 (5, d; 2.1), 3.87 (7-OCH$_3$, s), 6.83 (8, d; 8.5), 7.07 (9, dd; 8.5 and 2.1). $^{13}$C NMR (CDCl$_3$): unit δ (carbon position) A 165.3 (1), 125.3 (2), 141.0 (3), 36.7 (4), 76.2 (5), 40.6 (6), 13.5 (6-Me), 63.0 (7), 59.0 (8), 136.7 (9), 125.6 (10/14), 128.7 (11/13), 128.5 (12); D 170.7 (1), 71.3 (2), 39.4 (3), 24.5 (4), 22.9 (5), 21.3 (5'); C 175.6(1), 38.2 (2), 14.1 (2-Me), 41.1 (3); B 170.9 (1), 53.6 (2), 35.0 (3), 129.7 (4), 131.0 (5), 122.4 (6), 154.0 (7), 56.1 (7-OCH$_3$), 112.2 (8), 128.4 (9).

Cryptophycin 2

$[\alpha]_D$+20.4°(MeOH, c 0.54); UV $\lambda_{max}(\epsilon)$ 206 (43,800), 218 (37,500), 232 (22,900), 278 (2,410); CD $[\theta]_{203}$+54,100, $[\theta]_{212}$+16,500, $[\theta]_{225}$+53,600, $[\theta]_{236}$–14,000. IR (CHCl$_3$) $\nu_{max}$ 3423, 3029, 2961, 1742, 1724, 1678, 1512, 1258 cm$^{-1}$. EIMS m/$\geq$ (rel intensity, assignment) 620 (11, M$^+$), 431 (3), 378(8), 377 (6), 311 (11), 246 (10), 244 (8), 227 (14), 195 (17), 161 (84, CH$_3$O—C$_6$H$_4$—CH=CH=CO$^+$), 121 (79, CH$_3$O—C$_6$H$_4$—CH$_2^+$), 91 (100); high resolution EIMS m/$\geq$ 620.3094 (calcd for $C_{35}H_{44}N_2O_8$, 0.3 mmu error); 161.0605 (calcd for $C_{10}H_9O_2$, –0.2 mmu error); 121.0658 (calcd for $C_8H_9O$, –0.4 mmu error). $^1$H NMR (CDCl$_3$): amino or hydroxy acid unit δ (carbon position, multiplicity; J in Hz) 7,8-epoxy-5-hydroxy-6-methyl-8-phenyl-2-octenoic acid (A) 5.71 (2, dd; 15.4 and 1.3), 6.70 (3, ddd; 15.4, 10.2 and 5.0), 2.45 (4, m), 2.55 (4, m), 5.18 (5, ddd; 11.3, 4.8 and 2.0), 1.79 (6, m), 1.14 (6-Me, d; 7.0), 2.92 (7, dd; 7.7 and 2.0), 3.68 (8, d; 2.0), 7.24 (10/14, m), 7.34–7.39 (11/12/13, m); leucic acid (D) 4.82 (2, dd; 10.1 and 3.7), 1.70 (3, m), 1.33 (3, m), 1.70 (4, m), 0.86 (5, d; 6.4), 0.84 (5', d; 6.4); 3-amino-2-methylpropionic acid (C) 2.68 (2, m), 1.23 (2-Me, d; 7.3), 3.39 (3-H$_2$, m), 7.02 (3-NH,brt; 6.0); O-methyltyrosine (B) 4.79 (2, ddd; 8.1, 7.0 and 5.7), 5.55 (2-NH, d; 8.1), 3.07 (3, dd; 14.5 and 7.0), 3.13 (3, dd; 14.5 and 5.7), 7.10 (5/9, d; 8.6), 6.81 (6/8, d; 8.6), 3.78 (7-OCH$_3$, s). $^{13}$C NMR (CDCl$_3$): unit δ (carbon position) A 165.1 (1), 125.1 (2), 141.1 (3), 36.7 (4), 76.0 (5), 40.7(6), 13.6 (6-Me), 63.0 (7), 59.0 (8), 136.7 (9), 125.6 (10/14), 128.7 (11/13), 128.5 (12), D 170.6(1), 71.3 (2), 39.4 (3), 24.5 (4), 21.3 (5), 22.9 (5'); C176.0 (1), 38.1 (2), 14.2 (2-Me), 40.7 (3); B 171.1 (1), 53.9 (2), 35.3 (3), 131.0 (4), 130.2 (5/9), 114.1 (6/8), 158.6 (7), 55.2 (7-OCH$_3$).

Cryptophycin 3

$[\alpha]_D$+20.3°(MeOH, c 1.13); UV $\lambda_{max}(\epsilon)$ 206 (51,700), 218 (31,200), 230 (22,900), 246 (18,800), 280 (3,230); CD $[\theta]_{205}$+50,000, $[\theta]_{212}$–390, $[\theta]_{218}$–47,200, $[\theta]_{233}$–100, $[\theta]_{251}$+33,400, $[\theta]_{271}$+4,310. IR (CHCl$_3$) $\nu_{max}$ 3417, 2926, 1742, 1721, 1676, 1499, 1336 cm$^{-1}$. EIMS m/$\geq$ (rel intensity) 638/640 (2/0.7, M$^{+,}$ 412/414 (63/19), 280/282 (15/5), 227 (100), 195 (63), 91 (98); high resolution EIMS m/$\geq$ 638.2764 (calcd for $C_{35}H_{43}ClN_2O_7$, –0.5 mmu error), 412.1516 (calcd for $C_{20}H_{27}ClNO_6$, 1.1 mmu error), 227.1293 (calcd for $C_{15}H_{17}NO$, 1.0 mmu error). $^1$H NMR (CDCl$_3$): amino or hydroxy acid unit δ (carbon position, multiplicity; J in Hz) 5-hydroxy-6-methyl-8-phenyl-2,7- octadienoic acid (A) 5.77 (2, d; 15.5), 6.68 (3, ddd; 15.5, 9.5 and 5.3), 2.37 (4, m), 2.54 (4, m), 5.01 (5, ddd; 11.4, 6 and 1.5), 2.56 (6, m), 1.14 (6-Me, d; 7.0), 6.01 (7, dd; 15.8 and 8.8), 6.41 (8, d; 15.8), 7.28–7.34 (10/11/13/14, m), 7.23 (12, m); leucic acid (D) 4.84 (2, dd; 10.1 and 3.6), 1.62 (3, m), 1.36 (3, m), 1.62 (4, m), 0.77 (5, d; 6.5), 0.73 (5', d; 6.3); 3-amino-2-methylpropionic acid (C) 2.71 (2, m), 1.22 (2-Me, d; 7.3), 3.28 (3, dt; 13.5 and 7.0), 3.50 (3, ddd; 13.5, 4.9 and 4), 6.93 (3-NH, brt; 6.3); 3-chloro-4-methoxyphenylalanine (B) 4.82 (2, m), 5.64 (2-NH, d; 8.8), 3.05 (3, dd; 14.5 and 7.0), 3.13 (3, dd; 14.5 and 5.5), 7.22 (5, d; 2.2), 3.87 (7-OCH$_3$, s), 6.84 (8, d; 8.5), 7.08 (9, dd; 8.5 and 2.2). $^{13}$C NMR (CDCl$_3$): unit δ (carbon position) A 165.4 (1), 125.2 (2), 141.4 (3), 36.5 (4), 77.1 (5), 42.3 (6), 17.3 (6-Me), 130.1(7), 130.0 (8), 136.7 (9), 126.1 (10/14), 128.6 (11/13), 128.4 (12); D 170.1 (1), 71.6 (2), 39.5 (3), 24.5 (4), 21.2 (5), 22.7 (5'); C 175.6 (1), 38.3 (2), 14.0 (2-Me), 41.2 (3); B 170.9 (1), 53.5 (2), 35.1 (3), 129.8 (4), 131.0 (5), 122.4 (6), 154.0 (7), 56.1 (7-OCH$_3$), 112.2 (8), 127.6 (9).

Cryptophycin 4

[α]$_D$+36.7° (MeOH, c 1.93); UV) λ$_{max}$ (ε) 206 (41,800), 228 (25,000), 240 (21,200), 248 (22,500), 280 (3,000), 290 (1,230); CD [θ]$_{205}$+63,900, [θ]$_{211}$+3,040, [θ]$_{218}$−71,900, [θ]$_{229}$−11,700, [θ]$_{234}$−130, [θ]$_{252}$+47,500, [θ]$_{270}$+5,400. IR (CHCl$_3$) ν$_{max}$ 3410, 2962, 2917, 1741, 1718, 1678, 1511, 1251 cm$^{-1}$. EIMS m/z (rel intensity) 604 (2, M+), 378 (74), 246 (11), 227 (46), 161 (100), 91 (96); high resolution EIMS m/z 604.3127 (calcd for C$_{35}$H$_{44}$H2O$_7$, 2.2 mmu error), 378.1910 (calcd for C$_{20}$H$_{28}$NO$_6$, 0.7 mmu error), 227.1293 (calcd for C$_{15}$H$_{17}$NO, 1.7 mmu error), 161.0605 (calcd for C$_{10}$H$_9$O$_2$, −0.2 mmu error). $^1$H NMR (CDCl$_3$): amino or hydroxy acid unit δ (carbon position, multiplicity; J in Hz) 5-hydroxy-6-methyl-8-phenyl-2,7-octadienoic acid (A) 5.74 (2, dd; 15.3 and 1.2), 6.71 (3, ddd; 15.3, 10.3 and 5.0) 2.37 (4, m), 2.53 (4, m), 5.03 (5, ddd; 11.2, 6.4 and 2.0), 2.55 (6, m), 1.13 (6-Me, d; 6.8), 6.01 (dd; 15.8 and 8.8), 6.40 (8, d; 15.8), 7.28–7.37 (10/11/13/14, m), 7.22 (12, m); leucic acid (D) 4.84 (2, dd; 10.1 and 3.6), 1.65 (3, m), 1.34 (3, m), 1.65 (4, m), 0.75 (5, d; 6.5), 0.72 (5', d; 6.3); 3-amino-2-methylpropionic acid (C) 2.69 (2, m), 1.22 (2-Me, d; 7.5), 3.39 (3-H$_2$, m), 7.03 (3-NH, brt; 6.0); O-methyltyrosine (B) 4.79 (2, m), 5.61 (2-NH, d; 7.8), 3.08 (3, dd; 14.5 and 7.0), 3.13 (3, dd; 14.5 and 5.3), 7.11 (5/9, d; 8.8), 6.81 (d; 8.8), 3.78 (7-OCH$_3$, s). $^{13}$C NMR (CDCl$_3$): unit δ (carbon position) A 165.3 (1), 125.1 (2), 141.5 (3), 36.5 (4), 77.1 (5), 42.3 (6), 17.3 (6-Me), 130.1 (7), 131.8 (8), 136.7 (9), 126.2 (10/14), 128.7 (11/13), 127.6 (12); D 170.8 (1), 71.7 (2), 39.5 (3), 24.5 (4), 21.2 (5), 22.7 (5'); C 175.9 (1), 38.2 (2), 14.2 (2-Me), 40.9 (3); B 171.2 (1), 53.8 (2), 35.3 (3), 131.0 (4), 130.2 (5/9), 114.1 (6/8), 158.6 (7), 55.2 (7-OCH$_3$).

Cryptophycin 5

[α]$_D$+36.0° (MeOH, c 0.55); UV λ$_{max}$ (ε) 206 (45,600), 218 (37,700), 280 (3,790), 286 (3,480), 325 (2,080), CD [θ]$_{203}$+7,710, [θ]$_{206}$+29,000, [θ]$_{210}$−21,400, [θ]$_{222}$+59,800, [θ]$_{234}$+12,800, [θ]$_{241}$+13,700. IR (CHCl$_3$) ν$_{max}$ 3426, 2958, 1728, 1672, 1502, 1259 cm$^{-1}$. EIMS m/z (rel intensity) 686/688 (0.1510.05), 655/657 (1/0.3), 654/656 (1.5/0.5), 311/313 (75/27), 195 (66), 155 (54); 121 (51), 91 (100); high resolution EIMS m/z 686.2983 (calcd for C$_{36}$H$_{47}$ClN$_2$O$_9$, −1.3 mmu error). $^1$H NMR (CDCl$_3$): amino or hydroxy acid unit δ (carbon position, multiplicity; J in Hz) 7,8-epoxy-5-hydroxy-6-methyl-8-phenyl-2-octenoic acid (A) 5.87 (2, d; 15.3), 6.72 (3, dt; 15.3 and 6.8), 2.60 (4, m), 2.52 (4, ddd; 15.2, 7.8, and 6.8), 5.11 (5, ddd; 12.3, 7.8, and 7.1), 1.87 (6, m), 1.12 (6-Me, d; 7.1), 2.91 (7, dd; 7.3 and 2.1), 3.70 (8, d; 2.1), 7.24 (10/14, brd; 7.4), 7.29–7.36 (11/12/13, m); leucic acid (D) 4.09 (2, m), 2.86 (2-OH), brd, 6.1), 1.83 (3, m), 1.42 (3, m), 1.86 (4, m), 0.90 (5, d; 6.6), 0.87 (5'; d; 6.8); 3-amino-2-methylpropionic acid (C) 3.64 (I-OCH$_3$, s), 2.60 (2, m), 1.07 (2-Me, d; 7.3), 3.27 (3, ddd; 13.5, 8.0 and 5.5), 3.39 (3, m), 6.32 (3-NH, t; 5.4); 3-chloro-4-methoxyphenylalanine (B) 4.59 (2; dt; 6 and 7.5), 6.30 (2-NH, d; 7.5), 2.95 (3, dd; 13.6 and 7.5), 3.0 (3, dd; 13.6 and 6.0), 7.2 (5, d; 2.1), 3.86 (7-OCH$_3$, s), 6.84 (8, d; 8.5), 7.05 (9, dd, 8.5; 2.1). $^{13}$C NMR (CDCl$_3$): unit δ (carbon position) A 164.8 (1), 126.5 (2), 139.2 (3), 34.4 (4), 75.7 (5), 39.2 (6), 12.9 (6-Me), 63.3 (7), 58.7 (8), 136.8 (9), 125.7 (10/14), 128.6 (11/13), 128.4 (12); D 175.1 (1), 69.2 (2), 43.2 (3), 24.3 (4), 21.2 (5), 23.2 (5'); C 175.4 (1), 51.9 (1-OMe), 39.1 (2), 14.7 (2-Me), 41.6 (3); D 170.6 (1), 54.6 (2), 37.4 (3), 129.5 (4), 131.0 (5), 122.4 (6), 154.1 (7), 56.1 (7-OMe), 112.2 (8), 128.4 (9).

Cryptophycin 6

[α]$_D$+17.1°)(MeOH, c 1.1); UV λ$_{max}$ (ε) 206 (40,000), 218 (30,100), 228 (21,400), 282 (2,430), CD [θ]$_{203}$+37,700, [θ]$_{210}$−5,430, [θ]$_{213}$−1,260, [θ]$_{221}$+24,100, [θ]$_{232}$+8,480, [θ]$_{240}$+13,400, [θ]$_{254}$+790. IR (CHCl$_3$) ν$_{max}$ 3425, 3006, 2956, 1726, 1672, 1641, 1502, 1462, 1259 cm$^{-1}$. FABMS (thioglycerol) m/z, (rel intensity) 573/575 (13/6) [M—H$_2$O]$^+$, 217 (26), 91 (100). $^1$H NMR (CDCl$_3$): amino or hydroxy acid unit δ (carbon position, multiplicity; J in Hz) 5,7,8-trihydroxy-6-methyl-8-phenyl-2-octenoic acid (A) 5.92 (2, dt; 15.0 and 1.5), 6.94 (3, dt; 15 and 7.5), 2.51 (4, m), 2.64 (4, m), 3.97 (5, ddd; 9.3, 6.5 and 4.5), 2.03 (6, m), 1.10 (6-Me, d; 6.5), 3.70 (7, dd; 9.0 and 7.5), 4.64 (8, d; 7.5), 7.33–7.39 (10/11/13/14, m), 7.28 (12, tt; 6.5 and 2.0); 3-chloro-4-methoxyphenylalanine (B) 4.60 (2, dt; 8.0 and 6.0), 6.09 (2-NH, brd; 8.0), 2.96 (3, dd; 13.8 and 8.0), 3.02 (3, dd; 13.8 and 6.0), 7.22 (5, d; 2.0), 3.86 (7-OCH$_3$, s), 6.84 (8, d; 8.5), 7.07 (9, dd; 8.5 and 2.0) 3-amino-2-methylpropionic acid (C) 3.63 (1-OCH$_3$, s), 2.58 (2, m), 1.07 (2-Me, d; 7.0), 3.24 (3, ddd; 13.8, 8 and 6.5), 3.41 (3, ddd; 13.8, 6.5 and 4.8), 6.21 (3-NH, brt; 6.5). $^{13}$C NMR (CDCl$_3$): unit δ (carbon position) A 165.2 (1), 125.6 (2), 141.3 (3), 36.9 (4), 82.5 (5), 46.3 (6), 14.3 (6-Me), 85.1 (7), 84.8 (8), 140.9 (9), 125.8 (10/14), 128.6 (11/13), 127.8 (12); B 170.6 (1), 54.5 (2), 37.3 (3), 129.6 (4), 131.0 (5), 122.5 (6), 154.1 (7), 56.1 (7-OCH$_3$), 112.2 (8), 128.5 (9) C 52.0 (1-OCH$_3$), 175.4 (1), 39.2 (2), 14.7 (2-Me), 41.6 (3).

Cryptophycin 7

[α]$_D$−51.9° (MeOH, c 0.89); UV λ$_{max}$ (ε) 206 (23,400), 220 (14,900), 282 (1,670); CD [θ]$_{202}$+35,400, [θ]$_{206}$−1,730, [θ]$_{211}$−19,200, [θ]$_{220}$−15,800, [θ]$_{232}$+29,000, [θ]$_{263}$+2,040. IR (CHCl$_3$) ν$_{max}$ 3426, 2946, 1732, 1675, 1501, 1258 cm$^{-1}$. EIMS m/z (rel intensity) 455/457 (1/0.3, [M—2H$_2$O]$^+$), 105 (100), 77 (98); FABMS m/z (magic bullet matrix) 496/498 [M— H$_2$O+Na]$^+$, (thioglycerol matrix) 474/476 [M—H$_2$O1+H]$^+$. $^1$H NMR (CD$_3$OHD): amino or hydroxy acid unit δ (carbon position, multiplicity; J in Hz) 5,7,8-trihydroxy-6-methyl-8-phenyl-2-octenoic acid (A) 6.06 (2, ddd; 15.5, 1.3 and 1.0), 6.80 (3, dt; 15.5 and 7.5), 2.49 (4, m), 2.59 (4, m), 3.92 (5, ddd; 9.5, 6.3 and 4.7), 1.95 (6, m), 1.08 (6-Me, d; 6.7), 3.59 (7, dd; 9.0 and 7.8), 4.56 (8, d; 7.8), 7.37 (10/14, brd; 7.3), 7.31 (11/13, brt; 7.3), 7.24 (12, tt; 7.3 and 1.5); 3-chloro-4-methoxyphenylalanine (B) 4.52 (2, dd; 6.9 and 5.0), 2.93 (3, dd; 13.8 and 6.9), 3.15 (3, dd; 13.8 and 5.0), 7.20 (5, d; 2.2), 3.78 (7-OCH$_3$, s), 6.88 (8, d; 8.4), 7.08 (9, dd; 8.4 and 2.2). $^{13}$C NMR (CD$_3$OD): unit δ (carbon position) A 167.4 (1), 127.6 (2), 140.9 (3), 37.9 (4), 84.0 (5), 47.6 (6), 14.4 (6-Me), 86.0 (7), 85.8 (8), 142.9 (9), 127.1 (10/14), 129.3 (11/13), 128.5 (12); B 177.6 (1), 57.3 (2), 38.2 (3), 132.8 (4), 132.1 (5), 122.9 (6), 155.0 (7), 56.6 (7-OCH$_3$), 113.2 (8), 130.1 (9).

Cryptophycin 16

[α]$_D$+41.3° (MeOH, c 5.2); UV λ$_{max}$ (ε) 242 (4963), 280 (2430), 286 (2212); IR (neat) ν$_{max}$ 3402, 3270, 2960, 1748, 1724, 1676, 1514, 1466, 1343, 1239, 1177 cm$^{-1}$; EIMS m/z (rel intensity) 640/642 (66/27), 398/400 (47/16), 265 (55), 227 (93), 181 (100); high resolution EIMS m/z 640.25676 (calcd for C$_{34}$H$_{41}$ClN$_2$O$_8$, −1.6 mmu error). $^1$H NMR (CDCl$_3$): amino or hydroxyacid unit δ (carbon position, multiplicity; J in Hz) 7,8-epoxy-5-hydroxy-6-methyl-8-phenyl-2-octenoic acid (A) 5.74 (2, d; 16), 6.67 (3, ddd; 15.3, 9.7 and 5.5), 2.45 (4, dt; 14.3 and 10.4), 2.55 (4, brdd; 14.3 and 5.3), 5.15 (5, ddd; 11.2, 4.8 and 1.8), 1.8 (6, m), 1.14 (6-Me, d; 7.0), 2.92 (7, dd; 7.5 and 2.0), 3.69 (8, d; 2.0), 7.24–7.26 (10/14, m), 7.33–7.39 (11/12/13, m); 3-chloro-4-hydroxyphenylalanine (B) 4.8 (2, m), 5.64 (2-NH, d; 8.8), 3.03 (3, dd; 14.5 and 7.0), 3.11 (3, dd; 14.4 and 5.6), 7.17 (5, d; 2.2), 5.61 (7-OH), s), 6.91 (8, d; 8.3), 7.0 (9, dd; 8.3 and 2.2); 3-amino-2-methylpropionic acid (C) 2.71 (2, m), 1.22 (2-Me, d; 7.3), 3.28 (3, dt; 13.6 and 6.8), 3.49 (3, ddd; 13.6, 5 and 4.1), 6.92 (3-NH, br t; 6.1) leucic acid (D) 4.83 (2, dd; 10.1 and 3.3), 1.36 (3, m), 1.67–1.75 (3, m), 1.67–1.75 (4, m), 0.85 (5, d; 7.5), 0.86 (5', d; 6.8). $^{13}$C NMR (CDCl$_3$) unit δ (carbon position) A 165.3 (1), 125.3 (2), 141.0 (3), 36.7 (4), 76.2 (5), 40.6 (13.5 6-Me), 63.0 (7), 59.0 (8), 136.8 (9), 125.6 (10/14), 128.7 (11/13), 128.6 (12); B 170.9 (1), 53.6 (2), 35.1 (3), 129.9 (4), 129.6 (5), 120.0 (6), 150.4 (7), 116.4 (8), 129.2 (9); C 175.6 (1), 38.3 (2), 14.1 (2-Me), 41.1 (3); D 170.8 (1), 71.3 (2), 39.4 (3), 24.6 (4), 21.3 (5), 22.9 (5').

Cryptophycin 17

[α]$_D$+27.8° (CHCl$_3$c. 0.37); UV λ$_{max}$ (ε) 248 (14740), 268 (8100), 278 (3400), 284 (2840); IR (neat) ν$_{max}$ 3412, 2958, 1750, 1723, 1668, 1504, 1463, 1290, 1177, 751 cm$^{-1}$; EIMS m/z (rel intensity) 624/626 (10/3), 398/400 (95/35), 284 (100), 149 (95); high resolution EIMS m/z 624.26161 (calcd for C$_{34}$H$_{41}$ClN$_2$O$_7$, −1.4 mmu error). $^1$H NMR (CDCl$_3$): amino or hydroxyacid unit δ (carbon position, multiplicity; J in Hz) 5-hydroxy-6-methyl-8-phenyl-2,7-octadienoic acid (A) 5.77 (2, d; 15.4), 6.67 (3, ddd; 15.4, 9.5, and 5.3), 2.37 (4, m), 4.99 (5, ddd; 11.2, 6.3, and 1.6), 2.54 (6, m), 1.14 (6-Me, d; 6.7), 6.01 (7, dd; 15.7, and 8.7), 6.41 (8, d; 15.9), 7.28–7.34 (10/11/12/13/14, m), 7.23 (12, m); 3-chloro-4-hydroxyphenylalanine (B) 4.82 (2, m), 5.63 (2-NH, d; 8.7), 3.12 (3, dd; 14.7, and 5.6), 3.03 (3', dd; 14.7, and 7.1), 7.18 (5, d; 2.0), 5.47 (7-OH, br s), 6.91 (8, d; 8.3), 7.02 (9, dd; 8.3, and 2.0); 3-amino-2-methylpropionic acid (C) 2.71 (2, m), 1.21 (2-Me, d' 6.9), 3.25 (3, m), 3.52 (3, m), 3.52 (3', m), 6.89 (3-NH, br t; 6.1); leucic acid (D) 4.84 (2, dd; 9.6, and 3.1), 1.62 (3, m), 1.36 (3', m), 1.62 (4, m), 0.77 (5, d' 6.5), 0.73 (5', d; 6.5); $^{13}$C NMR (CDCl$_3$) unit δ (carbon position) A 165.4 (1), 125.3 (2), 141.3 (3), 36.5 (4), 77.1 (5), 42.3 (6), 17.3 (6-Me), 130.0 (7), 129.9 (8), 136.7 (9), 126.2 (10/14), 128.6 (11/13), 127.6 (12); B 170.9 (1), 53.5 (2), 35.1 (3), 129.6 (4), 131.9 (5), 126.2 (6), 150.3 (7), 116.3 (8), 127.6 (9); C 175.9 (1), 38.4 (2), 13.9 (2-Me), 41.3 (3); D 170.9 (1), 71.6 (2), 39.5 (3), 24.5 (4), 21.2 (5), 22.7 (5').

Cryptophycin 18

[α]$_D$+54.9° (MeOH, c 0.93); UV λ$_{max}$ (ε) 250 (20518), 284 (3857); IR (neat) ν$_{max}$ 3411, 3271, 2966, 1746, 1728, 1668, 1505, 1463, 1258, 1178 cm$^{-1}$; EIMS m/z (rel intensity) 638/640 (4.5/1.1), 412/414 (59/19), 280 (17), 227 (100); high resolution EIMS m/z 638.272934 (calcd for C$_{35}$H$_{43}$ClN$_2$O$_7$, 2.9 mmu error). $^1$H NMR (CDCl$_3$): amino or hydroxy acid unit δ (carbon position, multiplicity; J in Hz) 5-hydroxy-6-methyl-8-phenyl-2,7-octadienoic acid (A) 5.76 (2, d; 15.5), 6.65 (3, ddd; 15.4, 9.2 and 6.2), 2.38–2.47 (4, m), 5.08 (5, ddd; 10.6, 4.9 and 2.2), 2.58 (6, m), 1.15 (6-Me, d; 6.8), 6.07 (7, dd; 15.9 and 8.5), 6.43 (8, d; 15.9), 7.21–7.35 (10/11/12/13/14, m); 3-chloro-4-methoxyphenylalanine (B) 4.83 (2, m), 3.05 (3, dd; 14.5 and 7.1), 5.65 (2-NH, d; 8.7), 3.14 (3, dd; 14.4 and 5.5), 7.21 (5, d; 2.4), 3.86 (7-OCH$_3$, s), 6.83 (8, d; 8.3), 7.08 (9, dd; 8.3 and 2.2); 3-amino-2-methylpropionic acid (C) 2.73 (2, m), 1.23 (2-Me, d; 7.2), 3.23 (3, dt; 13.5 and 6.8), 3.56 (3, ddd; 13.5, 5.7 and 4.0), 6.85 (3-NH, dd; 7.1 and 6.2); leucic acid (D) 4.8 (2, d; 4.6), 1.86–1.89 (3, m), 0.94 (3-Me, d; 7.0), 1.20–1.26 (4, m), 1.39–1.44 (4, m), 0.77 (5, d; 7.4). $^{13}$C NMR (CDCl$_3$) unit δ (carbon position) A 165.5 (1), 125.2 (2), 141.5 (3), 36.4 (4), 77.7 (5), 41.9 (6-Me), 129.8 (7), 131.9 (8), 136.8 (9), 128.6 (10/14), 126.2 (11/13), 127.6 (12); B 170.0 (1), 53.5 (2), 35.1 (3), 129.9 (4), 131.1 (5), 122.4 (6), 153.9 (7), 56.1 (7-OCH3), 112.2 (8), 128.5 (9); C 175.3 (1), 38.6 (2), 14.0 (2-Me), 41.4 (3); D 169.5 (1), 76.7 (2), 36.2 (3), 15.5 (3-Me), 24.2 (4), 14.0 (5).

Cryptophycin 19

[α]$_D$+62.6° (MeOH, c 0.67); UV (MeOH) λ$_{max}$ (ε) 204 (44900), 230 (17000), 248 (15600), 280 (2500); IR (neat) ν$_{max}$ 3413, 3272, 2966, 1745, 1672, 1504, 1258, 1199, 1178, 1066, 692 cm$^{-1}$; EIMS m/z (rel intensity) 624/626 (3.0/1.4), 398.400 (58/21), 280/282 (15/5), 227 (100), 195/197 (57/22); high resolution EIMS m/z 624.2585 (calcd for C$_{34}$H$_{41}$ClN$_2$O$_7$, 1.8 mmu error). $^1$H-NMR (CDCl$_3$): amino or hydroxy acid unit δ (carbon position, multiplicity; J in Hz) 5-hydroxy-6-methyl-8-phenyl-2,7-octadienoic acid (A) 5.76 (2, d; 15.2), 6.64 (3, ddd; 15.4, 9.1 and 6.2), 2.38 (4, m), 2.47 (4, m), 5.04 (5, ddd; 7.1, 5.1 and 1.8), 2.57 (6, m), 1.15 (6-Me, d; 6.9), 6.05 (7, dd; 15.8 and 8.5), 6.43 (8, d; 15.8), 7.29–7.35 (10/11/12/13/14, m), 7.23 (12, m); 3-chloro-4-methoxyphenylalanine (B) 4.84 (2, m), 5.67 (2-NH, d; 8.9), 3.04 (3, dd; 14.3 and 7.1), 3.14 (3, dd; 14.3 and 5.3), 7.22 (5, d; 2.0), 3.86 (7-OCH$_3$, s), 6.83 (8, d; 8.2), 7.08 (9, dd; 8.2 and 2.0); 3-amino-2-methylpropionic acid (C) 2.75 (2, m), 1.23 (2-Me, d; 7.1), 3.19 (3, m), 3.59 (3, m), 6.80 (3-NH, brt; 6.7); 2-hydroxyisovaleric acid (D) 4.73 (2, d; 4.2), 2.09 (3, m), 0.84 (4, d; 6.9), 0.95 (4', d; 6.9). $^{13}$C NMR (CDCl$_3$) unit δ (carbon position) A 165.5 (1), 125.3 (2), 141.3 (3), 36.3 (4), 77.5 (5), 42.0 (6), 17.1 (6-Me), 129.9 (7), 131.9 (8), 136.8 (9), 126.1 (10/14), 128.6 (11/13), 127.6 (12); B 171.0 (1), 53.4 (2), 35.1 (3), 130.0 (4), 131.1 (5), 122.4 (6), 153.9 (7), 56.1 (7-OMe), 112.2 (8), 128.5 (9); C 175.1 (1), 38.7 (2), 13.9 (2-Me), 41.5 (3); D 169.6 (1), 76.9 (2), 19.0 (4), 16.7 (3-Me).

Cryptophycin 21

[α]$_D$+40.2° (CHCl$_3$ c 0.72); UV λmax (ε) 240 (6700), 280 (2400), 288 (2100); IR (neat) ν$_{max}$ 3403, 3279, 2957, 1731, 1673, 1503, 1464, 1409, 1372, 1258, 1174, 1065, 1023, 889 cm$^{-1}$; EIMS m/z (relative intensity) 640/642 (10/4), 612 (5), 478 (15), 398 (40), 266 (33), 227 (76), 195 (95), 155 (100), 127 (90); high resolution EIMS m/z 640.2550 (calcd for C$_{34}$H$_{41}$ClN$_2$O$_8$, 0.2 mmu error; $^1$H NMR (CDCl$_3$) amino or hydroxy acid unit δ (carbon positions, multiplicities; J in Hz) 7,8-epoxy-5-hydroxy-6-methyl-8-phenyl octanoic acid (A) 5.73 (2, d; 15.4), 6.68 (3, ddd; 15.0, 9.9 and 4.9), 2.45 (4, m), 2.56 (4, m), 5.19 (5, ddd; 11.2, 5.1 and 1.5), 1.80 (6, m), 1.14 (6-Me, d; 7.1), 2.92 (7, dd; 7.5 and 2.0), 3.68 (8, d; 1.8), 7.25 (10/14, m), 7.33–7.38 (11/12/13, m); 3-chloro-4-methoxyphenylalanine (B) 4.74 (2, ddd; 8.2, 6.8 and 6.2), 5.68 (2-NH, d; 8.6), 2.98 (3, dd; 14.3 and 7.7), 3.14 (3, dd; 14.3 and 5.6), 7.21 (5, d; 2.0), 3.86 (7-OMe, s), 6.83 (8, d; 8.4), 7.07 (9, dd; 8.4 and 2.0); 3-aminopropionic acid (C) 2.56 (2, m), 3.51 (3, m), 3.45 (3, m), 6.90 (3-NH, br t; 5.8); leucic acid (D) 4.89 (2, dd; 10.0 and 3.3), 1.67 (3, m), 1.31 (3, m), 1.67 (4, m), 0.84 (5; d; 6.4), 0.83 (5', d; 6.4); $^{13}$C NMR (CDCl$_3$) unit δ (carbon position) A 165.5 (1), 125.3 (2), 141.0 (3), 36.7 (4), 75.9 (5), 40.6 (6), 13.5 (6-Me), 63.0

(7), 59.0 (8), 136.7 (9), 125.6 (10/14), 128.7 (11/13), 128.5 (12); B 170.7 (1), 53.9 (2), 35.0 (3), 129.8 (4), 130.9 (5), 122.4 (6), 153.9 (7), 56.1 (7-OMe), 112.2 (8), 128.3 (9); C 172.6 (1), 32.4 (2), 34.4 (3), D 170.5 (1), 61.2 (2), 39.5 (3), 24.4 (4), 22.8 (5), 21.2 (5').

Cryptophycin 23

$[\alpha]_D$+47° (MeOH, c 1.55); UV $\lambda_{max}$ ($\epsilon$) 240 (4571), 282 (2174), 290 (2177); IR (neat) $\nu_{max}$ 3284, 2960, 1747, 1724, 1653, 1540, 1490, 1339, 1272, 1174 cm$^{-1}$; EIMS m/z (rel intensity) 674/675/678 (47/35/8), 432/434/436 (11/5/2), 299/301/303 (39/30/7), 227 (64), 215/217/219 (31/20/8), 141 (100); high resolution EIMS m/z 674.21643 (calcd. for $C_{34}H_4Cl_2N_2O_8$, −0.3 mmu error); $^1$H NMR (CDCl$_3$) amino or hydroxyacid unit δ (carbon position, multiplicity; J in Hz) 7,8-epoxy-5-hydroxy-6-methyl-8-phenyl-2-octenoic acid (A) 5.77 (2, d; 15.4), 6.65 (3, ddd; 15.4, 9.3 and 6.0), 2.47 (4, dt; 14.2 and 10.2), 2.55 (4, br dd; 14.2 and 5.6), 5.13 (5, ddd; 11.0, 4.6 and 1.6), 1.81 (6, m), 1.15 (6-Me, d; 6.9), 2.93 (7, dd; 7.6 and 2.0), 3.7 (8, d; 2.0), 7.22–7.26 (10/14, m), 7.32–7.39 (11/12/13, m); 3,5-dichloro-4-hydroxyphenylalanine (B) 4.81 (2, m), 5.69 (2-NH, d; 8.6), 3.11 (3, dd; 14.5 and 5.6), 3.50 (3, dd; 14.3 and 7.0), 7.13 (5/9, s), 5.78 (7-OH, s); 3-amino-2-methylpropionic acid (C) 2.73 (2, m), 1.22 (2-Me, d; 7.1), 3.19 (3, dt; 13.4 and 6.9), 3.58 (3, ddd; 13.6, 5.8 and 4.1), 6.82 (3-NH, br t; 5.9); leucic acid (D) 4.84 (2, dd; 9.9 and 3.2), 1.38 (3, m), 1.68–1.75 (3, m), 1.68–1.75 (4, m), 0.86 (4-Me, d; 6.7), 0.87 (5, d; 6.7). $^{13}$C NMR (CDCl$_3$) unit δ (carbon position) A 165.4 (1), 125.4 (2), 140.9 (3), 36.7 (4), 76.3 (5), 40.6 (6), 13.5 (6-Me), 63.0 (7), 58.9 (8), 136.7 (0), 125.6 (10/14), 128.7 (11/13), 128.6 (12); B 170.7 (1), 53.5 (2), 35.0 (3), 130.3 (4), 129.0 (5/9), 121.0 (6/8), 146.7 (7); C 175.3 (1), 38.4 (2), 13.9 (2-Me), 41.5 (3); D 170.8 (1), 71.3 (2), 39.4 (3), 24.6 (4), 21.3 (4-Me), 22.9 (5).

Cryptophycin 24

$[\alpha]_D$+48.8° (CHCl$_3$, c 0.63); UV $\lambda_{max}$ ($\epsilon$) 228 (19006), 242 (8249), 274 (2351); IR (neat) $\nu_{max}$ 3400, 3284, 2959, 1732, 1678, 1652, 1514, 1248, 1178 cm$^{-1}$; EIMS m/z (rel intensity, assignment) 606 (2, M$^+$), 364 (7), 161 (55, $CH_3O-C_6H_4-CH=CH=CO^+$), 121 (100, $CH_3O-C_6H_4-CH_2^+$), 91 (68); high resolution EIMS m/z 606.2954 (calcd. for $C_{34}N_{42}N_2O_8$, −1.3 mmu error); $^1$H NMR (CDCl$_3$) amino or hydroxy acid unit δ (carbon position, multiplicity; J in Hz) 7,8-epoxy-5-hydroxy-6-methyl-8-phenyl-2-octenoic acid (A) 5.70 (2, dd; 15.2 and 1.3), 6.70 (3, ddd; 15.2, 10.3 and 4.7), 2.43 (4, dt; 14.3 and 10.9), 2.56 (4, m), 5.20 (5, ddd; 11.3, 5.1 and 2.0), 1.79 (6, m), 1.14 (6-Me, d; 7.0), 2.92 (7, dd; 7.5 and 2.0), 3.68 (8, d; 2.0), 7.23–7.38 (10/11/12/13/14, m); O-methyltyrosine (B) 4.73 (2, m), 5.58 (2-NH, d; 8.3), 3.03 (3, dd; 14.5 and 7.5), 3.14 (3, dd; 14.5 and 5.7), 7.11 (5/9, d; 8.6), 6.81 (6/8, d; 8.6), 3.78 (7-OMe, s); 3-aminopropionic acid (C) 2.55 (2-H$_2$, m), 3.42 (3, m), 3.53 (3, m), 6.97 (3-NH, br t; 5.7); leucic acid (D) 4.89 (2, dd; 9.9 and 3.5), 1.29 (3, m), 1.62–1.70 (3/4, m), 0.83 (5, d; 5.9), 0.84 (5', d; 6.1); $^{13}$C NMR (CDCl$_3$): unit δ (carbon position) A 165.4 (1), 125.3 (2), 141.0 (3), 36.7 (4), 75.9 (5), 40.6 (6), 13.4 (6-Me), 63.0 (7), 59.0 (8), 136.7 (9), 125.6 (10/14), 128.7 (11/13), 128.5 (12); B 170.7 or 170.6 (1), 54.1 (2), 35.2 (3), 128.5 (4), 130.2 (5/9), 114.1 (6/8), 158.6 (7), 55.2 (7-OMe); C 172.8 (1), 32.5 (2), 34.2 (3); D 170.6 or 170.7 (1), 71.2 (2), 39.5 (3), 24.4 (4), 21.3 (5), 22.8 (5').

Cryptophycin 26

$[\alpha]_D$+28.2° (CHCl$_3$, c 1.31); UV $\lambda_{max}$ ($\epsilon$) 254 (14615), 284 (2949); IR (neat) $\nu_{max}$ 3299, 2960, 1732, 1644, 1504, 1258, 1209 cm$^{-1}$; EIMS m/z (rel intensity) 656/658 (0.5/0.1, M$^+$), 638/640 (1.7/1.0), 525/527 (3.7/1.8), 412/414 (10/4), 280/282 (12/11), 227 (20), 195 (48), 131 (68); high resolution EIMS m/z 656.2836 (calcd for $C_{35}H_{45}ClN_2O_8$, 2.8 mmu error), 638.2712 (calcd for $C_{35}H_{43}ClN_2O_7$, 4.7 mmu error); $^1$H NMR (CDCl$_3$) amino or hydroxy acid unit δ (carbon position, multiplicity; J in Hz) 3,5-dihydroxy-6-methyl-8-phenyl-7-octenoic acid (A) 2.46 (2, dd; 14.8 and 7.8), 2.58 (2, dd; 14.8 and 3.0), 5.46 (3, m), 1.86–1.90 (4-H$_2$, m), 3.61 (5, m), 2.37 (6, m), 1.14 (6-Me, d; 6.8), 6.06 (7, dd; 16 and 8.7), 6.47 (8, d; 16), 7.37 (10/14, br d; 7.9), 7.32 (11/13, br t; 7.6), 7.22–7.28 (12, m); 3-chloro-4-methoxyphenylalanine (B) 4.73 (2, br dt; 6.4 and 8.1), 6.14 (2-NH, d; 8.6), 2.84 (3, dd; 14.4 and 8), 3.18 (3, dd; 14.4 and 6.3), 7.21 (5, d; 2.2), 3.85 (7-OMe, s), 6.82 (8, d; 8.6), 7.08 (9, dd; 8.6 and 2.2); 3-amino-2-methylpropionic acid (C) 2.87 (2, m), 1.19 (2-Me, d; 7.0), 3.01 (3, ddd; 13.4, 10.6 and 4.9), 3.73 (3, ddd; 13.4, 8.2 and 4.7), 6.72 (3-NH, br dd; 7.3 and 5.2); leucic acid (D) 4.95 (2, dd; 9.7 and 4.2), 1.62–1.72 (3, m), 1.79–1.84 (3, m), 1.62–1.72 (4, m), 0.90 (4-Me, d; 6.4), 0.95 (5, d; 6.4). $^{13}$C NMR (CDCl$_3$): unit δ (carbon position) A 170.0 (1), 41.5 (2), 71.4 (3), 37.3 (4), 71.9 or 71.8 (5), 43.6 (6), 16.6 (6-Me), 130.8 (7), 132.5 (8), 136.8 (9), 126.2 (10/14), 128.6 (11/13), 127.6 (12); B 170.9 (1), 53.2 (2), 34.7 (3), 130.3 (4), 131.1 (5), 122.2 (6), 153.8 (7), 56.1 (7-OMe), 112.2 (8), 128.5 (9); C 174.3 (1), 40.1 (2), 14.4 (2-Me), 42.5 (3); D 170.7 (1), 71.8 or 71.9 (2), 38.9 (3), 24.6 (4), 21.6 (4-Me), 22.9 (5).

Cryptophycin 28

$[\alpha]_D$+65.6° (MeOH, c 0.93); UV (MeOH) $\lambda_{max}$ ($\epsilon$) 204 (48000), 230 (19300), 248 (18700), 280 (3400); IR (neat) $\nu_{max}$ 3413, 3270, 2958, 1745, 1726, 1665, 1504, 1258, 1197, 1175, 1066, 694 cm$^{-1}$; EIMS m/z (rel intensity) 624/626 (3.0/1.3), 412/414 (70/24), 280/282 (13/6), 213 (100), 195/197 (86/40); high resolution EIMS m/z 624.2626 (calcd for $C_{34}H_{41}ClN_2O_7$, −2.4 mmu error); $^1$H NMR (CDCl$_3$) amino or hydroxy acid unit δ (carbon position, multiplicity; J in Hz) 5-hydroxy-8-phenyl-2,7-octadienoic acid (A) 5.78 (2, d; 15.6), 6.71 (3, ddd; 15.6, 9.9 and 5.4), 2.40 (4, m), 2.53 (4, m), 5.17 (5, m), 2.53 (6-H$_2$, br t; 6.7), 6.07 (7, dt; 15.8 and 7.4), 6.44 (8, d; 15.8), 7.27–7.38 (10/11/13/14, m), 7.22 (12, m); 3-chloro-4-methoxyphenylalanine (B) 4.82 (2, m), 5.72 (2-NH, d; 8.5), 3.04 (3, dd; 14.5 and 7.2), 3.14 (3, dd; 14.5 and 5.4), 7.22 (5, d; 2.0), 3.87 (7-OMe, s), 6.84 (8, d; 8.5), 7.08 (9, dd; 8.5 and 2.0); 3-amino-2-methylpropionic acid (C) 2.72 (2, m), 1.21 (2-Me, d; 7.2), 3.29 (3, dt; 13.5 and 7.0), 3.49 (3, ddd; 13.5, 4.9 and 3.8), 6.97 (3-NH, br t; 5.6); leucic acid (D) 4.82 (2, m), 1.40 (3, m), 1.62 (3, m), 1.62 (4, m), 0.76 (4-Me, d; 6.3), 0.74 (5, d; 6.3); $^{13}$C NMR (CDCl$_3$) unit δ (carbon position) A 165.4 (1), 125.2 (2), 141.2 (3), 38.5 (4), 73.5 (5), 38.6 (6), 124.1 (7), 133.8 (8), 136.7 (9), 126.1 (10/14), 128.6 (11/13), 127.6 (12); B 170.9 (1), 53.6 (2), 35.1 (3), 129.8 (4), 131.0 (5), 122.4 (6), 154.0 (7), 56.1 (7-OMe), 112.3 (8), 128.4 (9); C 175.6 (1), 38.3 (2), 14.0 (2-Me), 41.2 (3), D 170.9 (1), 71.6 (2), 39.6 (3), 24.5 (4), 21.5 (4-Me), 22.6 (5).

Cryptophycin 29

$[\alpha]_D$+22.2° (CHCl$_3$, c 1.13); UV $\lambda_{max}$ ($\epsilon$) 250 (17000), 284 (3300); IR (neat) $\nu_{max}$ 3415, 3272, 2960, 1744, 1734, 1674, 1504, 1259, 1197, 1174, 1067, 694 cm$^{-1}$; EIMS m/z (rel intensity) 624/626 (2.6/1.1), 398/400 (44/15), 227 (100), 195/197 (50/16), 155/157 (59/20), 131 (63), 91 (95); high resolution EIMS m/z 624.2607 (calcd. for $C_{34}H_{41}ClN_2O_7$, −0.5 mm error); $^1$H NMR (CDCl$_3$) amino or hydroxy acid unit δ (carbon position, multiplicity; J in Hz); 5-hydroxy-6-methyl-8-phenyl-2,7-octadienoic acid (A) 5.75 (2, dd; 15.3 and 1.1), 6.69 (3, ddd; 15.3, 10.1 and 5.3), 2.36 (4, m), 2.54 (4, m), 5.03 (5, ddd; 11.0, 6.4 and 1.8), 2.56 (6, m), 1.14 (6-Me, d; 6.8), 6.01 (7; dd; 15.8 and 8.8), 6.41 (8, d; 15.8), 7.28–7.33 (10/11/13/14, m), 7.22 (12, m); 3-chloro-4-methoxyphenylalanine (B) 4.76 (2, m), 5.67 (2-NH, d; 8.6), 3.0 (3, dd; 14.4 and 10.2), 3.14 (3, dd; 14.4 and 5.9), 7.22 (5, d; 2.2), 3.87 (7-OMe, s), 6.83 (8, d; 8.4), 7.08 (9, dd; 8.4 and 2.2); 3-aminopropionic acid (C) 2.55 (2-H$_2$, m), 3.44 (3, m), 3.55 (3, m), 6.89 (3-NH, br t; 5.7); leucic acid (D) 4.90 (2, dd; 9.9 and 3.5), 1.34 (3, ddd; 15.4, 10.3 and 3.5), 1.63 (3, m), 1.63 (4, m). 0.76 (4-Me, d; 6.4), 0.72 (5, d; 6.4); $^{13}$C NMR (CDCl$_3$) unit δ (carbon position) A 165.6 (1), 125.2 (2), 141.5 (3), 36.4 (4), 77.1 (5), 42.3 (6), 17.3 (6-Me), 130.1 (7), 131.8 (8), 136.7 (9), 126.2 (10/14), 128.6 (11/13), 127.6 (12); B 170.9 (1), 53.8 (2), 34.9 (3), 129.9 (4), 131.0 (5), 122.4 (6), 153.9 (7), 56.1 (7-OMe), 112.2 (8), 128.4 (9); C 172.6 (1), 32.4 (2), 34.5 (3); D 170.4 (1), 71.5 (2), 39.7 (3), 24.4 (4), 21.2 (4-Me), 22.6 (5).

Cryptophycin 30

[α]$_D$ −12.3° (CHCl$_3$, c 1.53); UV λ$_{max}$ (ε) 254 (17200), 284 (3600); IR (neat) ν$_{max}$ 3414, 3306, 2961, 1738, 1729, 1660, 1504, 1258, 1205, 1183, 1066, 695 cm$^{-1}$; EIMS m/z (rel intensity) 656/658 (1.0/0.3), 638/640 (3.0/1.0), 525/527 (3.81/1.3), 412/414 (10.5/3.6), 280/282 (10.3/3.8), 227 (29), 195/197 (48/17), 155/157 (74/21), 131 (100); high resolution EIMS m/z 656.2852 (calcd for C$_{35}$H$_{45}$ClN$_2$O$_8$, 1.3 mmu error); $^1$H-NMR (CDCl$_3$): amino or hydroxy acid unit δ (carbon position, multiplicity; J in Hz) 3.5-dihydroxy-6-methyl-8-phenyl-7-octenoic acid (A) 2.25 (2, dd; 16.0 and 9.6), 2.64 (2, brd; 16.0), 3.89 (3, m), 2.51 (3-OH, d; 6.4), 1.77 (4, ddd; 14.3, 9.8 and 2.1), 1.88 (4, ddd; 11.3 and 3.8), 4.88 (5, ddd; 11.3, 6.2 and 2.1), 2.53 (6, m), 1.10 (6-Me, d; 6.8), 5.99 (7, dd; 15.9 and 9.0), 6.40 (8, d; 15.9), 7.28–7.33 (10/11/13/14, m), 7.23 (12, m); 3-chloro-4-methoxyphenylalanine (B) 4.60 (2, m), 6.61 (2-NH, d; 8.1), 3.09 (3, dd; 14.2 and 5.6), 3.15 (3, dd; 14.2 and 7.3), 7.22 (5, d; 2.1), 3.86 (7-OMe, s), 6.83 (8, d; 8.3), 7.07 (9, dd; 8.3 and 2.1); 3-amino-2-methylpropionic acid (C) 2.67 (2, m), 1.21 (2-Me, d; 7.3), 3.26 (3, ddd; 13.6, 7.3 and 6.4), 3.63 (3, ddd; 13.6, 6.2 and 3.9), 6.75 (3-NH, br t; 6.3); leucic acid (D) 4.83 (2, dd; 9.6, 4.1), 1.42 (3, m), 1.64 (3, m), 1.64 (4, m). 0.79 (4-Me, d; 6.4), 0.76 (5, d; 6.4); $^{13}$C NMR (CDCl$_3$) unit δ (carbon position) A 171.6 (1), 42.4 (2), 66.0 (3), 41.3 (4), 76.0 (5), 42.0 (6), 17.3 (6-Me), 130.0 (7), 131.9 (8), 136.7 (9), 126.1 (10/14), 128.6 (11/13), 127.6 (12); B 170.8 (1), 54.3 (3), 35.1 (3), 130.1 (4), 131.1 (5), 122.2 (6), 153.8 (7), 56.1 (7-OMe), 112.1 (8), 128.7 (9); C 175.6 (1), 39.7 (2), 13.8 (2-Me), 41.5 (3), D 171.9 (1), 72.1 (2), 39.1 (3), 24.6 (4), 21.4 (4-Me), 22.7 (5).

Cryptophycin 31

[α]$_D$ +50.6° (MeOH, c 1.13); UV λ$_{max}$ (ε) 242 (3800), 284 (700); IR (neat) ν$_{max}$ 3412, 3272, 2961, 1745, 1725, 1678, 1537, 1481, 1270, 1196, 1176, 1000, 698 cm$^-$; EIMS m/z (rel intensity) 688/690/692 (1.2/1.0/0.4), 446/448/450 (7.9/6.7/3.1), 314/316/318 (17/11/3), 91 (100) high resolution EIMS m/z 688.2336 (calcd for C$_{35}$H$_{42}$Cl$_2$N$_2$O$_8$, −1.8 mmu error); $^1$H-NMR (CDCl$_3$) amino or hydroxy acid unit δ (carbon position, multiplicity; J in Hz) 7.8-epoxy-5-hydroxy-6-methyl-8-phenyl-2-octenoic acid (A) 5.78 (2, d; 15.5), 6.66 (3, ddd; 15.5, 9.4 and 6.0), 2.47 (4, ddd; 14.1, 10.8 and 9.40, 2.56 (4, m), 5.14 (5, ddd; 10.8, 4.7 and 1.7), 1.82 (6, m), 1.15 (6-Me, d; 7.1), 2.93 (7, dd; 7.5 and 1.9), 3.70 (8, d; 1.9), 7.24–7.26 (10/14, m), 7.34–7.39 (11/12/13, m); 3,5-dichloro-4-methoxyphenylalanine (B) 4.83 (2, m), 5.68 (2-NH, d; 9.0), 3.0 (3, dd; 14.4 and 7.3), 3.14 (3, dd; 14.4 and 5.6), 7.16 (5/9, s), 3.87 (7-OMe, s); 3-amino-2-methylpropionic acid (C) 2.74 (2,m), 1.22 (2-Me, d; 7.1), 3.20 (3, m), 3.58 (3, ddd; 13.5, 5.6 and 4.1), 6.82 (3-NH, br t; 5.6); leucic acid (D) 4.83 (2, m), 1.38 (3, m), 1.72 (3, m), 1.72 (4, m), 0.87 (4-Me, d; 6.8), 0.86 (5, d; 6.8); $^{13}$C NMR (CDCl$_3$) unit δ (carbon position) A 165.4 (1), 125.4 (2), 141.0 (3), 36.7 (4), 76.3 (5), 40.6 (6), 13.5 (6-Me), 63.0 (7), 58.9 (8), 136.7 (9), 125.6 (10/14), 128.7 (11/13), 128.6 (12); B 170.8 (1), 53.5 (2), 35.2 (3), 129.3 (4), 129.6 (5/9), 134.5 (6/8), 151.2 (7), 60.6 (7-OMe); C 175.3 (1), 38.3 (2), 13.9 (2-CH3), 41.5 (3), D 170.6 (1), 71.3 (2), 39.4 (3), 24.6 (4), 22.9 (4-Me), 21.3 (5).

Cryptophycin 40

[α]$_D$ +41.6° (CHCl$_3$, c 0.31); UV λ$_{max}$ (ε) 242 (4974), 266 (3911), 274 (3666), 286 (2359), 328 (511); IR (neat) ν$_{max}$ 3415, 2959, 1748, 1723, 1667, 1505, 1463, 1289, 1176 cm$^{-1}$; EIMS m/z (rel intensity) 640/642 (5/2), 280/282 (7/3), 213 (13), 195/197 (51/17), 155 (29), 141 (32), 121 (28), 91 (100), 69 (47); high resolution EIMS m/z 640.2570 (calcd. for C$_{34}$H$_{41}$ClN$_2$O$_8$, −1.8 mmu error); $^1$H NMR (CDCl$_3$) amino or hydroxy acid unit δ (carbon positions, multiplicities; J in Hz) 7,8-epoxy-5-hydroxy-8-phenyl-2-octenoic acid (A) 5.77 (2, d; 15.1), 6.72 (3, ddd; 15.1, 9.7 and 4.9), 2.42 (4, m), 2.58 (4, m), 5.33 (5, m), 1.89 (6, ddd; 12.9, 8.1 and 5.0), 2.13 (6, ddd; 12.9, 9.3 and 5.0), 2.98 (7, ddd; 6.7, 4.5 and 1.9), 3.64 (8, d; 1.9), 7.31–7.39 (10/11/13/14, m), 7.22 (12, m); 3-chloro-4-methoxyphenylalanine (B) 4.83 (2, m), 5.64 (2-NH, d; 8.6), 3.03 (3, dd; 14.3 and 7.5), 3.14 (3, dd; 14.3 and 5.4), 7.21 (5, d; 2.0), 3.87 (7-OMe, s), 6.84 (8, d; 8.3), 7.08 (9, dd; 8.3 and 2.0); 3-amino-2-methylpropionic acid (C) 2.72 (2, m), 1.23 (2-Me, d; 7.3), 3.31 (3, dt; 13.8 and 6.9), 3.50 (3, ddd; 13.6, 5.7 and 3.9), 6.96 (3-NH, br t; 6.0); leucic acid (D) 4.85 (2, dd; 6.7, 3.4), 1.42 (3, m), 1.72 (3, m), 1.72 (4, m), 0.86 (4-Me, d, 3.7), 0.87 (5, d, 3.7); $^{13}$C NMR (CDCl$_3$) unit δ (carbon position) A 165.3 (1), 125.2 (2), 140.9 (3), 39.0 (4), 72.0 (5), 37.3 (6), 59.0 (7), 58.7 (8), 140.9 (9), 125.6 (10/14), 128.7 (11/13), 128.5 (12); B 170.9 (1), 53.6 (2), 35.1 (3), 129.8 (4), 131.0 (5), 122.5 (6), 157.0 (7), 56.1 (7-OMe), 112.3 (8), 128.4 (9); C 175.6 (1), 38.3 (2), 14.1 (2-Me), 41.1 (3); D 170.9 (1), 71.4 (2), 39.4 (3), 24.5 (4), 21.5 (4-Me), 22.8 (5).

Cryptophycin 43

[α]$_D$ +20° (CHCl$_3$, c 0.2); UV λ$_{max}$ (ε) 250 (20512), 282 (4083), 294 (1734); IR (neat) ν$_{max}$ 3400, 3272, 2927, 1727, 1660, 1516, 1455, 1242, 1175 cm$^-$; EIMS m/z (rel intensity) 533 (24), 484 (3), 445 (14), 398 (9), 364 (29), 227 (59), 149 (67), 91 (100); high resolution EIMS m/z 590.3044 (calcd for C$_{34}$H$_{41}$N$_2$O$_7$, −5.2 mmu error); $^1$H NMR (CDCl$_3$) amino or hydroxy acid unit δ (carbon position, multiplicity, J in Hz) 5-hydroxy-6-methyl-8-phenyl-2,7-octadienoic acid (A) 5.75 (2, d; 15.3), 6.69 (3, ddd; 15.3, 9.9 and 5.3), 2.37 (4, dt; 14.2 and 10.4), 2.52 (4, m), 5.01 (5, ddd; 11.2, 6.4 and 1.8), 2.55 (6, m), 1.13 (6-Me, d; 6.9), 6.01 (7, dd; 15.8 and 8.9), 6.41 (8, d; 15.8), 7.21–7.34 (10/11/12/13/14, m); 4-methoxyphenylalanine (B) 4.80 (2, m), 5.64 (2-NH, d; 8.4), 3.06 (3, dd; 14.5 and 7.2), 3.13 (3, dd; 14.4 and 5.3), 7.06 (5/9, d; 8.4), 6.74 (6/8, d; 8.4); 3-amino-2-methylpropionic acid (C) 2.69 (2, m), 1.22 (2-Me, d; 7.3), 3.33 (3, m), 3.44 (3, dt; 14.0 and 4.7), 7.0 (3-NH, m); leucic acid (D) 4.84 (2, dd; 10.0 and 3.6), 1.60–1.67 (3, m), 1.35 (3, m), 1.60–1.67 (4, m), 0.76 (5, d; 6.4), 0.73 (5', d; 6.7); $^{13}$C NMR (CDCl$_3$) unit δ (carbon position) A 125.2 (2), 141.5 (3), 36.5 (4), 77.5 (5), 42.3 (6), 17.3 (6-Me), 130.1 (7), 131.8 (8), 136.8 (9), 126.2 (10/14), 128.6 (11/13), 127.6 (12); B 53.8 (2), 35.3 (3), 129.8 (4), 130.5 (5/9), 115.6 (6/8), 154.6 (7); C 38.3 (2), 14.1 (2-Me), 41.0 (3); D 71.6 (2), 39.6 (3), 24.5 (4), 21.2 (5), 22.9 (5'). Due to the small sample size, carbonyl carbon signals could not be seen.

Cryptophycin 45

[α]$_D$ +72.0° (MeOH, c 0.122); UV λ$_{max}$ (ε) 250 (25500), 284 (5300); IR (neat) ν$_{max}$ 3407, 3239, 2958, 1743, 1727, 1667, 1538, 1469, 1242, 1196, 1177, 694 cm$^{-1}$; EIMS m/z (rel intensity) 658/660/662 (2.1/1.4/0.3), 483 (7.6) 432/434/436 (9.5/6.4/1.8), 300/302/304 (8.0/5.5/1.2), 227 (100) 91 (87); high resolution EIMS m/z 658.2207 (calcd for $C_{34}H_{40}Cl_2N_2O_7$, 0.6 mmu error); $^1$H-NMR (CDCl$_3$): amino or hydroxy acid unit δ (carbon position, multiplicity; J in Hz) 5-hydroxy-6-methyl-8-phenyl-2,7-octadienoic acid (A) 5.80 (2, d; 14.7), 6.66 (3, ddd; 14.7, 8.5 and 5.5), 2.38 (4, m), 2.53 (4, m), 4.97 (5, br dd; 10.4 and 6.2), 2.57 (6, m), 1.14 (6-Me, d; 6.7), 6.01 (7, dd; 15.9 and 8.7), 6.42 (8, d; 15.9), 7.28–7.34 (10/11/1314, m), 7.22 (12, m); 3,5-dichloro-4-hydroxyphenylalanine (B) 4.82 (2, m), 5.73 (2-NH, br d; 8.7), 3.02 (3, dd; 14.3 and 6.2), 3.10 (3, dd; 14.3 and 5.2), 7.14 (5/9, s), 5.79 (7-OH, s); 3-amino-2-methylpropionic acid (C) 2.73 (2, m), 1.21 (2-Me, d; 7.0), 3.17 (3, m), 3.60 (3, m), 6.81 (3-NH, br t; 6.7); leucic acid (D) 4.84 (2, dd; 10.0 and 3.2), 1.38 (3, ddd; 14.9, 10.2 and 3.2), 1.65 (3, m), 1.65 (4, m). 0.78 (4-Me, d; 6.5), 0.73 (5, d; 6.5); $^{13}$C NMR (CDCl$_3$) unit δ (carbon position) A 165.5 (1), 125.4 (2), 141.2 (3), 36.4 (4), 77.6 (5), 42.3 (6), 17.3 (6-Me), 130.0 (7), 131.9 (8), 136.7 (9), 126.2 (10/14), 128.6 (11/13), 127.6 (12); B 171.0 (1), 53.2 (2), 35.0 (3), 130.4 (4), 129.1 (5/9), 121.0 (6/8), 146.7 (7); C 175.2 (1), 38.5 (2), 13.9 (2-Me), 41.6 (3), D 170.7 (1), 71.5 (2), 39.5 (3), 24.6 (4), 22.7 (4-Me), 21.2 (5).

Cryptophycin 49

[α]$_D$+68.1° (MeOH, c 0.075); UV λ$_{max}$ (ε) 246 (25500), 284 (5200); IR (neat) ν$_{max}$ 3401, 3282, 2962, 1744, 1728, 1668, 1540, 1505, 1464, 1258, 1198, 1177, 1066, 694 cm$^{-1}$; EIMS m/z (rel intensity) 624/626 (0.8/0.3), 398/400 (43/14), 227 (78), 195/197 (58/26) 91 (100); high resolution EIMS m/z 624.2650 (calcd for $C_{34}H_{41}ClN_2O_7$, -4.8 mmu error); $^1$H-NMR (CDCl$_3$): amino or hydroxy acid unit δ (carbon position, multiplicity; J in Hz) 5-hydroxy-6-methyl-8-phenyl-2,7-octadienoic acid (A) 5.77 (2, d; 14.1), 6.67 (3, m), 2.38 (4, m), 2.50 (4, m), 5.01 (5, m), 2.56 (6, m), 1.13 (6-Me, d; 6.5), 6.03 (7, dd; 15.8 and 8.6), 6.42 (8, d; 15.8), 7.29–7.35 (10/11/13/14, m), 7.23 (12; m); 3-chloro-4-methoxyphenylalanine (B) 4.82 (2, m), 5.64 (2-NH, m), 3.06 (3, m), 3.13 (3, m), 7.22 (5, m), 3.87 (7-OMe, s), 6.83 (8, m), 7.08 (9, m); 3-amino-2-methylpropionic acid (C) 2.72 (2, m), 1.22 (2-Me, d; 6.7), 3.26 (3, m), 3.53 (3, m), 6.90 (3-NH, m); 2-hydroxyvaleric acid (D) 4.81 (2, dd; 8.8 and 3.9), 1.63 (3, m), 1.68 (3, m), 1.33 (4-H$_2$, m). 0.74 (5, t; 7.3).

Cryptophycin 50

[α]$_D$+32.0° (CHCl$_3$, c. 0.44); UV λ$_{max}$(ε) 242 (4933), 262 (3996), 274 (3719), 286 (2430), 332 (359); IR (neat) ν$_{max}$ 3412, 3274, 2958, 1752, 1724, 1676, 1648, 1503, 1465, 1258, 1177, 1066, 753; EIMS m/z (rel intensity) 640/642 (4/2), 398/400 (11/4), 280/282 (10/3), 227 (17), 195/197 (57/18), 157 (20), 141 (31), 91 (100); high resolution EIMS m/z 640.2531 (calcd. for $C_{34}H_{41}ClN_2O_8$, 2.1 mmu error); $^1$H NMR (CDCl$_3$) amino or hydroxy acid unit_δ (carbon positions, multiplicities; J in Hz) 7.8-epoxy-5-hydroxy-6-methyl-8-phenyl octanoic acid (A) 5.73 (2, d; 15.7), 6.67 (3, ddd; 15.7, 9.7 and 5.4), 2.45 (4, m), 2.55 (4, m), 5.13 (5, ddd; 11.2, 5.0 and 1.7), 1.78 (6, m), 1.15 (6-Me, d, 6.9), 2.91 (7, dd; 7.5 and 1.9), 3.68 (8, d; 1.7), 7.25 (10/14, m), 7.33–7.38 (11/12/13; m); 3-chloro-4-methoxyphenylalanine (B) 4.80 (2, ddd; 8.3, 7.1 and 5.4), 5.61 (2-NH, d; 8.3), 3.03 (3, dd; 14.4 and 7.3), 3.13 (3, dd; 14.4 and 5.6), 7.21 (5, d; 1.9), 3.87 (7-OMe, s), 6.83 (8, d; 8.4), 7.07 (9, dd; 8.4 and 2.2); 3-amino-2-methylpropionic acid (C) 2.71 (2, m), 1.22 (2-Me, d; 7.3), 3.29 (3, dt; 13.6 and 6.9), 3.49 (3, ddd; 13.6, 6.7 and 5.0), 6.92 (3-NH, br t; 6.7); 2-hydroxypenanoic acid (D) 4.75 (2, dd; 9.2 and 3.7), 1.55 (3, m), 1.65 (3, m), 1.33 (4-H$_2$, m), 0.84 (5, t; 7.3); $^{13}$C NMR (CDCl$_3$) unit δ values (carbon positions) A 165.3 (1), 125.3 (2), 141.0 (3), 36.9 (4), 76.3 (5), 40.8 (6), 13.6 (6-Me), 63.2 (7), 59.1 (8), 136.8 (9), 125.5 (10/14), 128.7 (11/13), 128.5 (12); B 170.9 (1), 53.6 (2), 35.1 (3), 129.8 (4), 131.0 (5), 122.5 (6), 154.0 (7), 56.1 (7-OMe), 112.3 (8), 128.5 (9); C 175.6 (1), 38.4 (2), 14.1 (2-Me), 41.2 (3); D 170.4 (1), 72.4 (2), 32.7 (3), 18.4 (4), 13.5 (5).

Cryptophycin 54

EIMS m/z (relative intensity) 654/656 (17/10), 493 (5), 411/413 (12/4), 280 (16), 227 (25), 195/197 (45/25), 141 (30), 91 (100); high resolution EIMS m/z 654.2686 (calcd for $C_{35}H_{43}ClN_2O_8$, 2.2 mmu error); $^1$H NMR (CDCl$_3$): amino or hydroxy acid unit δ (carbon position, multiplicity; J in Hz) 5-hydroxy-6-methyl-7-oxo-8-phenyl-2-octenoic acid (A) 5.73 (2, d; 15.4), 6.66 (3, ddd; 15.4, 9.7, 5.7), 2.46 (4, m), 2.53 (4, m), 5.16 (5, ddd; 11.0, 4.2, 1.7), 1.79 (6, m), 1.14 (6-Me, d; 6.8), 2.89 (7, dd; 7.4, 1.8), 3.69 (8, d; 1.9), 7.25 (10/14, m), 7.30–7.38 (11/12/13, m), (B) 4.81 (2, m), 5.63 (2-NH, d; 8.6), 3.03 (3, dd; 14.5, 7.3), 3.13 (3, dd; 14.5, 5.5), 7.21 (5, d; 2.2), 3.87 (7-OMe, s), 6.83 (8, d; 8.4), 7.07 (9, dd; 8.4, 2.2); (C) 2.73 (2, m), 1.22 (2-Me, d; 7.3), 3.26 (3, ddd; 13.4, 6.8, 6.8), 3.51 (3, ddd; 13.4, 6.8, 5.3), 6.88 (3-NH, br t; 6.8); (D) 4.73 (2, d; 4.2), 1.78–1.82 (3, m), 0.92 (3-Me, d; 6.8), 1.36–1.41 (4, m), 1.18–1.20 (4, m), 0.80 (5, t; 7.5); $^{13}$C NMR (CDCl$_3$) unit δ (carbon position) A 164.3 (1), 125.4 (2), 141.0 (3), 36.6 (4), 76.3 (5), 40.6 (6), 13.2 (6-Me), 63.1 (7), 58.7 (8), 136.7 (9), 125.4 (10/14), 128.6 (11/13), 128.5 (12); B 170.9 (1), 53.5 (2), 35.0 (3), 129.8 (4), 131.0 (5), 125.2 (6), 153.9 (7), 56.1 (7-OMe), 112.2 (8), 128.4 (9); C 175.4 (1), 38.5 (2), 14.0 (2-Me), 41.3 (3); D 169.4 (1), 76.5 (2), 36.1 (3), 15.6 (3-Me), 24.0 (4), 11.2 (5).

EXAMPLE 6

Synthesis of Cryptophycin Derivatives

Cryptophycin 8

To a solution of 3.8 mg of Cryptophycin 1 in 1.5 mL of 2:1 1,2-dimethoxyethane/water was added 9 μL 1N HCl. The solution was allowed to stir at room temperature for 4 h, neutralized with potassium carbonate, and evaporated. The residue was partitioned between water and CH$_2$Cl$_2$. The CH$_2$Cl$_2$-soluble material was purified by reversed-phase HPLC to obtain 3.3 mg of pure Cryptophycin 8.

EIMS m/z (relative intensity) 690/692/694 (0.8/0.5/0.2). High resolution EIMS m/z 690.2533 (calcd for $C_{35}H_{44}Cl_2N_2O_8$, -5.8 mmu error). $^1$H NMR (CDCL$_3$): amino or hydroxy acid unit δ (carbon position, multiplicity; J in Hz) 8-chloro-5,7-dihydroxy-6-methyl-8-phenyl-2-octenoic acid (A) 5.79 (2, d; 15.4), 6.69 (3, ddd; 15.4, 9.7 and 5.6), 2.68 (4, ddt; 14.0, 5.5 and 1.8), 2.38 (4, m), 5.11 (5, ddd; 10.8, 8.6 and 1.8), 2.51 (6, m), 1.05 (6-Me, d; 7.0), 4.01 (7, dd; 9.6 and 1.9), 4.65 (8, d; 9.6), 7.36–7.41 (10/11/12/13/14, m); leucic acid (D) 4.92 (2, dd; 10.1 and 3.5), 1.76 (3/4, m), 1.45 (4, m), 0.94 (5, d; 6.6), 0.94 (5', d; 6.4); 3-amino-2-methylpropionic acid (C) 2.73 (2, m), 1.22 (2-Me, d; 7.2), 32.5 (3, ddd; 13.6, 6.8 and 6.1), 3.54 (3, ddd; 13.5, 6.1 and 3.4), 6.91 (3-NH, brt; 6.1); 3-chloro-4-methoxyphenylalanine (B) 4.82 (2, ddd; 8.8, 7.2 and 5.6), 5.64 (2-NH, d; 8.8), 3.03 (3, dd; 15.4 and 7.2), 3.16 (3, dd; 15.4 and 5.6), 7.23 (5, d; 2.2), 3.88 (7-OCH$_3$, s), 6.85 (8, d; 8.5), 7.09 (9, dd; 8.5 and 2.2).

Cryptophycin 9

To a solution of 10 mg of Cryptophycin 1 in 1 mL dry methanol was added 10 μL methanolic HCl (obtained by treating 1.25 g thionyl chloride with 25 mL MeOH). After stirring for 4 h the solvent was removed in vacuo and the sample was left under vacuum for 12 h. Reversed-phase HPLC gave 8 mg of pure Cryptophycin 9.

$^1$H NMR (CDCl$_3$): amino or hydroxy acid unit δ (carbon position, multiplicity; J in Hz); 5,7-dihydroxy-8-methoxy- 6-methyl-8-phenyl-2-octenoic acid (A) 5.76 (2, d; 15.5), 6.67 (3, ddd; 15.5, 9.5 and 5.6), 2.34 (4, ddd; 14.1, 11.1 and 9.5), 2.62 (4, dddd; 14.1, 5.6, 1.8 and 1.5), 5.09 (5, ddd; 11.1, 7.8 and 1.8), 2.24 (6, dqd; 7.8, 7.0 and 2.2), 1.03 (6-Me, d; 7.0), 3.71 (7, dd; 8.3 and 2.2), 4.03 (8, d; 8.3), 3.20 (8-OCH$_3$, s), 7.31–7.40 (10/11/12/13/14, m); leucic acid (D) 4.86 (2, dd; 9.8 and 3.5), 1.71 (3/4, m), 1.41 (3, m), 0.89 (5/5', d; 6.4); 3-amino-2-methylpropionic acid (C) 2.71 (2, ddq; 6.8, 3.9 and 7.2), 1.21 (2-Me, d; 7.2), 3.23 (3, ddd; 13.5, 6.8 and 6.0), 3.52 (3, ddd; 13.5, 6.0 and 3.9), 6.90 (3-NH, brt; 6.0); 3-chloro-4-methoxyphenylalanine (B) 4.82 (2, ddd; 8.8, 7.4 and 5.7), 5.66 (2-NH, d; 8.8), 3.02 (3, dd; 14.4, 7.4), 3.15 (3, dd; 14.4 and 5.5), 7.23 (5, d; 2.2), 3.87 (7-OCH$_3$, s), 6.84 (8, d; 8.5), 7.08 (9, dd; 8.5 and 2.2).

Cryptophycin 10

To a stirred solution of 7 mg of Cryptophycin 9 in 1 mL of acetone and 0.3 mL water was added 8 μL of 2N NaOH. After stirring for 4 h the solution was neutralized to pH 7 with 1N HCl and the solvent was removed under reduced pressure. The residue was subjected to reversed-phase HPLC using 7:3 MeOH/H$_2$O to yield pure Cryptophycin 10 (5 mg).

$^1$H NMR (CD$_3$OD): amino or hydroxy acid unit δ (carbon position, multiplicity; J in Hz); 5,7-dihydroxy-8-methoxy-6-methyl-8-phenyl-2-octenoic acid (A) 5.92 (2, dt; 15.4 and 1.3), 6.82 (3, dt; 15.4 and 7.3), 2.30 (4, m), 2.50 (4, m), 3.66 (5, td; 7.8 and 3.5), 2.05 (6, d pentent; 1.8 and 7.0), 0.96 (6-Me, d; 7.0), 4.04 (7, dd; 8.8 and 2.0), 4.01 (8, d; 8.8), 3.12 (8-OCH$_3$, s), 7.26–7.36 (10/11/12/13/14, m); 3-amino-2-methylpropionic acid (C) 2.50 (2, m), 1.02 (2-Me, d; 7.3), 3.16 (3, dd; 13.4 and 6.9), 3.82 (3, dd; 13.4 and 6.6); 3-chloro-4-methoxyphenylalanine (B) 4.57 (2, dd; 8.5 and 6.5), 2.82 (3, dd; 13.9 and 8.6), 3.03 (3, dd; 13.9 and 6.5), 7.25 (5, d; 2.2), 3.82 (7-OCH$_3$, s), 6.96 (8, d; 8.6), 7.13 (9, dd; 8.6 and 2.2). $^{13}$C NMR (CD$_3$OD): δ 179.5, 173.4, 168.2, 155.4, 143.7, 141.7, 131.9, 129.8, 129.3 (2C), 129.2 (2C), 128.8, 126.2, 123.2, 113.4, 85.9, 74.5, 74.1, 56.8, 56.6, 56.3, 43.3, 41.2, 40.2, 38.8, 38.0, 15.5, 9.9.

Cryptophycin 12

To a solution of 5 mg of Cryptophycins 1, 5 or 8 in 1 mL of 4:1 acetone/water was added 15 μL of 2N NaOH. After stirring at room temperature for 5 hr, the reaction mixture was neutralized to pH 7 with 1N HCl and evaporated. The CH$_2$Cl$_2$-soluble material was passed through a small silica-cartridge sigh CH$_2$Cl$_2$, 1:1 EtO Ac/CH$_2$Cl$_2$, and EtO/Ac. The fraction eluted with EtOAc contained pure Cryptophycin 12.

$^1$H NMR (CD$_3$OD): amino or hydroxy acid unit δ (carbon position, multiplicity; J in Hz); 5,7,8-trihydroxy-6-methyl-8-phenyl-2-octenoic acid (A) 6.07 (A) (2, ddd; 15.5, 1.3 and 1.2), 6.40 (3, dt; 15.5 and 7.3); 2.49 (4, m), 2.60 (4, m), 3.92 (5, ddd; 9.3, 6.7 and 4.5), 1.94 (6, m), 1.07 (6-Me, d; 6.6), 3.61 (7, dd; 8.9 and 7.6), 4.56 (8, d; 7.6), 7.36 (10/14, dd; 7.4 and 1.5), 7.32 (11/13, brt; 7.5), 7.25 (12, m); 3-amino-2-methylpropionic acid (C) 2.54 (2, ddq; 7.0, 6.6 and 7.0), 1.02 (2-Me, d; 7.0), 3.14 (3, dd; 13.5 and 7.0), 3.42 (3, dd; 13.4 and 6.6); 3-chloro-4-methoxyphenylalanine (B) 4.57 (2, dd; 8.4 and 6.7), 2.83 (3, dd; 13.8 and 8.4), 3.02 (3, dd; 13.8 and 6.6), 7.25 (5, d; 2.1), 3.82 (7-OCH$_3$, s), 6.95 (8, d; 8.5), 7.12 (9, dd; 8.5 and 2.1). Methylation of Cryptophycin 12 with diazomethane gave Cryptophycin 6.

Cryptophycin 14

To a solution of 3 mg of Cryptophycin 6 in 1 mL of 3:1 acetone/H$_2$O was added 5 μL of 2N NaOH. After stirring for 5 h, the reaction mixture was neutralized to pH 7 with 1N HCl and then evaporated to dryness. The residue was subjected to reversed-phase HPLC to give 2.4 mg of Cryptophycin 14.

$^1$H NMR (CD$_3$OH): amino or hydroxy acid unit δ (carbon position, multiplicity; J in Hz); 5-hydroxy-6-methyl-8-phenyl-2,7-octadienoic acid (A) 5.98 (2, d; 15.3), 6.78 (3, dt; 15.3 and 7.5), 2.35 (4, m), 3.64 (5, dt; 7.2 and 4.8), 2.47 (6, m), 1.14 (6-Me, d; 6.9), 6.22 (7, dd; 15.9 and 8.1), 6.39 (8, d, 15.9), 7.24–7.36 (10/11/12/13/14, m); 3-amino-2-methylpropionic acid (c) 2.235 (2, m), 1.02 (2-Me, d; 6.9), 3.18 (3, dd; 13.2 and 6.6), 3.36 (3, dd; 13.2 and 4.5); 3-chloro-4-methoxyphenylalanine (B) 4.58 (2, dd; 8.7 and 6.3), 2.80 (3, dd; 13.8 and 9.0), 3.05 (3, dd; 13.8 and 6.3), 7.25 (5, d; 2.1), 3.82 (7-OCH$_3$, s), 6.95 (8, d; 8.4), 7.13 (9, dd; 8.4 and 2.1).

Cryptophycin 35

A catalytic amount of PtO$_2$ was added to a flask containing 0.5 ml of CH$_2$Cl$_2$. The air in the flask was evacuated, H$_2$ was introduced, and the mixture was stirred at room temperature for 20 min. A solution of 10 mg of Cryptophycin 1 in minimum CH$_2$Cl$_2$ was added and the mixture was stirred at room temperature for 45 min. The catalyst was removed by filtration through celite/cotton and the solvent was evaporated. Reversed phase HPLC of the residue on a C18 column yielded 6.5 mg of Cryptophycin 35.

EIMS m/z (relative intensity) 656/658 (25/10), 412/414 (25/12), 280/282 (20/10), 195/197 (78/25), 141 (58), 91 (100); high resolution EIMS m/z 656.2864 (calcd for C$_{35}$H$_{45}$ClN$_2$O$_8$ 0.0 mmu error); $^1$H NMR (CDCl$_3$) amino or hydroxy acid unit__δ__values (carbon positions, multiplicities; J in Hz) 2,3-dihydro-7,8-epoxy-5-hydroxy-6-methyl-8-phenyl octanoic acid (A) 2.32 (2, ddd; 14.5, 9.2, 5.8), 2.10 (2, ddd; 14.5, 9.2, 6.2), 1.5–1.8 (3/4 overlapping m), 5.07 (5, ddd; 12.5, 5.6, 2.0), 1.80 (6, m), 1.12 (6-Me, d; 7.0), 2.90 (7, dd; 7.4, 1.8), 3.67 (8, d; 1.8), 7.24 (10/14, m), 7.32–7.38 (11/12/13, m); 3-chloro-4-methoxyphenylalanine (B) 4.71 (2, ddd; 8.7, 6.4, 6.3), 5.62 (2-NH), d; 8.7), 3.08 (2H-3, br d; 6.4), 7.19 (5, d; 2.0), 3.87 (7-OMe, s), 6.83 (8, d; 8.5), 7.07 (9, dd; 8.4, 2.0); 3-amino-2-methylpropionic acid (C) 2.72 (2, m), 1.18 (2-Me, d; 6.9), 3.12 (3, ddd; 11.4, 10.6, 5.6), 3.70 (3, ddd), 6.76 (3-NH, br t, 6.0); leucic acid (D) 4.83 (2, dd; 9.9, 3.8), 1.39 (3, m), 1.70 (3, m), 1.72 (4, m), 0.87 (4-Me, d; 5.3), 0.86 (5, d; 5.3); $^{13}$C NMR (CDCl$_3$) unit δ__values (carbon positions) A 172.4 (1), 36.2 (2), 32.0 (3), 21.1 (4), 76.7 (5), 40.2 (6), 13.6 (6-Me), 63.3 (7), 59.2 (8), 136.8 (9), 125.6 (10/14), 128.7 (11/13), 128.6 (12); B 170.7 (1), 53.7 (2), 35.5 (3), 130.0 (4), 131.1 (5), 122.2 (6), 153.8 (7), 56.1 (7-OMe), 112.1 (8), 128.5 (9); C 175.2 (1), 38.2 (2), 13.6 (2-Me), 42.1 (3); D 171.9 (1), 71.7 (2), 39.6 (3), 24.5 (4), 22.9 (4-Me), 21.4 (5).

EXAMPLE 10

Analysis of Microtubule Depolymerizing Activity of Cryptophycin

Materials

Vinblastine, cytochalasin B, tetramethylrhodamine isothiocyanate (TRITC)-phalloidin, sulforhodamine B (SRB) and antibodies against β-tubulin and vimentin were obtained from the Sigma Chemical Company. Basal Medium Eagle containing Earle's salts (BME) was from Gibco and Fetal Bovine Serum (FBS) was purchased from Hyclone Laboratories.

Cell Lines

The Jurkat T cell leukemia line and A-10 rat aortic smooth muscle cells were obtained from the American type Culture Collection and were cultured in BME containing 10% FBS and 50 μg/ml gentamycin sulfate. Human ovarian carcinoma cells (SKOV3) and a sub-line which has been selected for resistance to vinblastine (SKVLB1) were a generous gift from Dr. Victor Ling of the Ontario Cancer Institute. Both cell lines were maintained in BME containing 10% FBS and 50 μg/ml gentamycin sulfate. Vinblastine was added to a final concentration of 1 μg/ml to SKVLB1 cells 24 hours after passage to maintain selection pressure for P-glycoprotein-overexpressing cells.

Cell Proliferation and Cycle Arrest Assays

Cell proliferation assays were performed as described by Skehan et al.[11] For Jurkat cells, cultures were treated with the indicated drugs as described in Skehan[11] and total cell numbers were determined by counting the cells in a hemacytometer. The percentage of cells in mitosis was determined by staining with 0.4% Giemsa in PBS followed by three rapid washes with PBS. At least 1000 cells per treatment were scored for the presence of mitotic figures and the mitotic index was calculated as the ratio of cells with mitotic figures to the total number of cells counted.

Immunofluorescence Assays

A-10 cells were grown to near-confluency on glass coverslips in BME/10% FBS. Compounds in PBS were added to the indicated final concentrations and cells were incubated for an additional 24 hours. For the staining of microtubules and intermediate filaments, the cells were fixed with cold methanol and incubated with PBS containing 10% calf serum to block nonspecific binding sites. Cells were then incubated at 37° C. for 60 min with either monoclonal anti-β-tubulin or with monoclonal anti-vimentin at dilutions recommended by the manufacturer. Bound primary antibodies were subsequently visualized by a 45-minute incubation with fluorescein-conjugated rabbit antimouse IgG. The coverslips were mounted on microscope slides and the fluorescence patterns were examined and photographed using a Zeiss Photomicroscope I11 equipped with epifluoroescence optics for fluorescein. For staining of microfilaments, cells were fixed with 3% paraformaldehyde, permeabilized with 0.2% Triton X-100 and chemically reduced with sodium borohydride (1 mg/ml). PBS containing 100 nM TRITC-phalloidin was then added and the mixture was allowed to incubate for 45 min at 37° C. The cells were washed rapidly three times with PBS before the coverslips were mounted and immediately photographed as described above.

Figure 2:
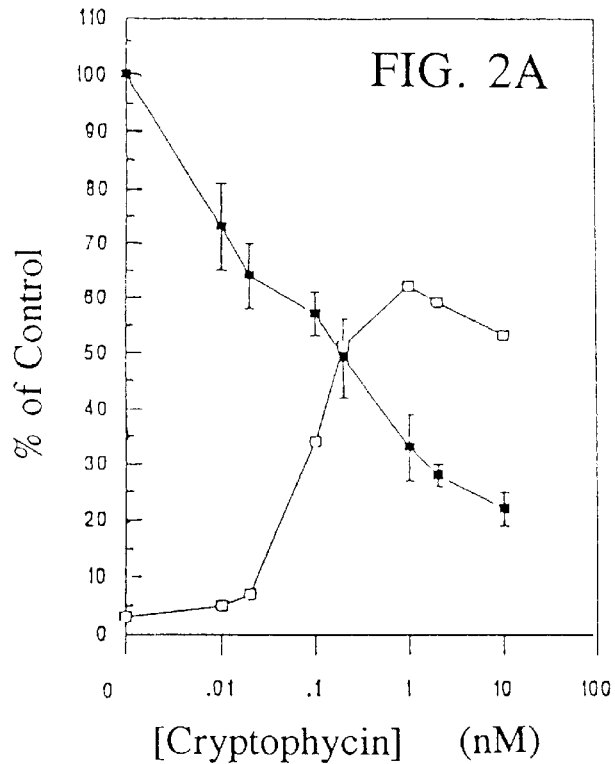
FIGS. 2a and 2b graphically presents the effects of cryptophycin compounds and vinblastine on Jurkat cell proliferation and cell cycle progression. Jurkat cells were incubated with the indicated concentrations of cryptophycin compounds (A) or vinblastine (B) for 24 hours. For each sample, the number of viable cells (■) and the mitotic index (□) were determined as described in the Experimental section. Values represent the means ± standard deviation (sd) for triplicate samples in one of three similar experiments.
Figure 2:
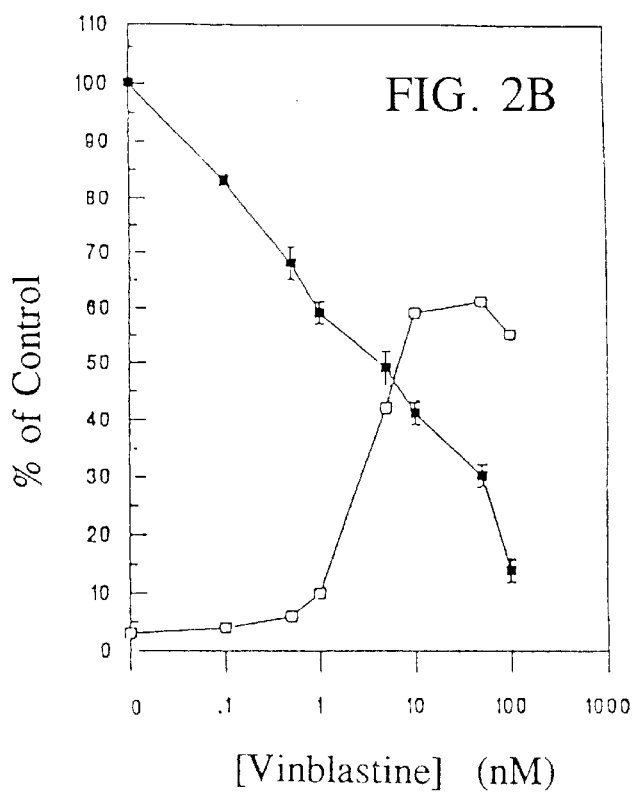

Effects of cryptophycins and vinblastine on Jurkat cell proliferation and cell cycle Dose-response curves for the effects of cryptophycin compounds and vinblastine on cell proliferation and the percentage of cells in mitosis are indicated in FIGS. 2A and 2B, respectively. Less than 3% of untreated cells displayed mitotic figures. Both the cryptophycin compounds and vinblastine caused dose-dependent increases in the percentage of cells observed in mitosis. The increase in the mitotic index was closely correlated with decreases in cell proliferation, i.e. the concentrations of both cryptophycin compounds and vinblastine that caused 50% of the cells to accumulate in mitosis was virtually the same as the concentration which inhibited cell proliferation by 50%. The $IC_{50}$s for the cryptophycin compounds and vinblastine for these effects were 0.2 and 8 nM, respectively.

Effects of cytochalasin B, vinblastine and cryptophycins on the cytoskeleton

Aortic smooth muscle (A-10) cells were grown on glass coverslips and treated with PBS, 2 μM cytochalasin B, 100 nM vinblastine or 10 nM cryptophycin compounds. After 24 hours, microtubules and vimentin intermediate filaments were visualized by indirect immunofluorescence and microfilaments were stained using TRITC-phalloidin. The morphological effects of each drug were examined. Untreated cells displayed extensive microtubule networks complete with perinuclear microtubule organizing centers. Vimentin intermediate filaments were also evenly distributed throughout the cytoplasm, while bundles of microfilaments were concentrated along the major axis of the cell. Cytochalasin B caused complete depolymerization of microfilaments along with the accumulation of paracrystalline remnants. This compound did not affect the distribution of either microtubules or intermediate filaments. Both vinblastine and the cryptophycin compound caused marked depletion of microtubules. Neither compound affected microfilament organization; however, vimentin intermediate filaments collapsed, forming concentric rings around the nuclei of cells treated with either vinblastine or a cryptophycin compound.

Effects of cryptophycins and vinblastine on taxol-stabilized microtubules

A-10 cells were treated for 3 hours with 0 or 10 μM taxol before the addition of PBS, 100 nM vinblastine or 10 nM cryptophycin compound. After 24 hours, microtubule organization was examined by immunofluorescence as described above. Compared with those in control cells, microtubules in taxol-treated cells were extensively bundled, especially in the cell polar regions. As before, vinblastine caused complete depolymerization of microtubules in non-pretreated cells. However, pretreatment with taxol prevented microtubule depolymerization in response to vinblastine. Similarly, taxol pretreatment completely stabilized microtubules against cryptophycin-induced depolymerization.

Reversibility of microtubule depolymerization by vinblastine and cryptophycin

A-10 cells were treated with either 100 nM vinblastine or 10 nM cryptophycins for 24 hr, resulting in complete microtubule depolymerization. The cells were then washed and incubated in drug-free medium for periods of 1 hour or 24 hours. Microtubules repolymerized radpidly after the removal of vinblastine, showing significant levels of microtubules after 1 hour and complete morphological recovery by 24 hour. In contrast, microtubules did not reappear in cells treated with cryptophycin compounds at either 1 hour or 24 hours after removal of the compound.

Figure 3:
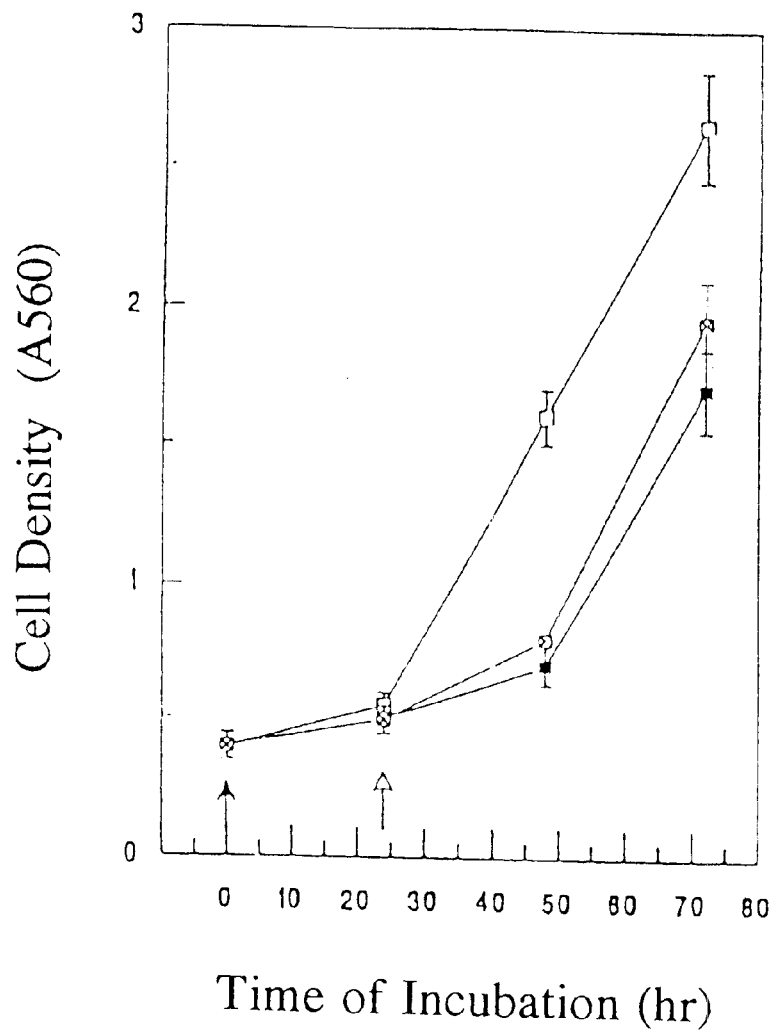
FIG. 3 graphically presents the reversibility of the effects of vinblastine, cryptophycins and taxol on cell growth. SKOV3 cells were treated with 0.1 nM vinblastine (□), 0.1 nM cryptophycins (■) or 1 nM taxol (⊠) at time=0. These concentrations inhibited cell growth by 50% for each compound. After 24 hours the cells were washed and incubated in drug-free medium for the time indicated. The cell density was determined by sulforhodamine B (SRB) staining as described in the Experimental Section, and is expressed as the mean ± sd adsorbance at 560 nm for triplicate samples in one of three experiments.

Reversibility of cryptophycins-, vinblastine- and taxol-inhibition of cell proliferation SKOV3 cells were treated for 24 hours with previously determined $IC_{50}$ doses of vinblastine, cryptophycin compounds or taxol (i.e. values determined in experiments summarized in Table 5). During this time the cell density increased from 0.4 to 0.5±0.05 absorbance units (FIG. 3), indicating a 25% increase in cell number for all three treatments. Removal of the drugs resulted in rapid growth of the vinblastine-treated cells, such that their numbers were increased approximately 3-fold in 24 hours. In contrast, cells treated with cryptophycin compounds or taxol remained arrested, increasing only 0.2- to 0.4-fold in the 24 hours following removal of the drug. The proliferative capacity of cryptophycins or taxol-treated cells was subsequently restored since the cells then doubled in the next 24 hours.

Effects of combinations of vinblastine and cryptophycins on cell proliferation

Figure 4:
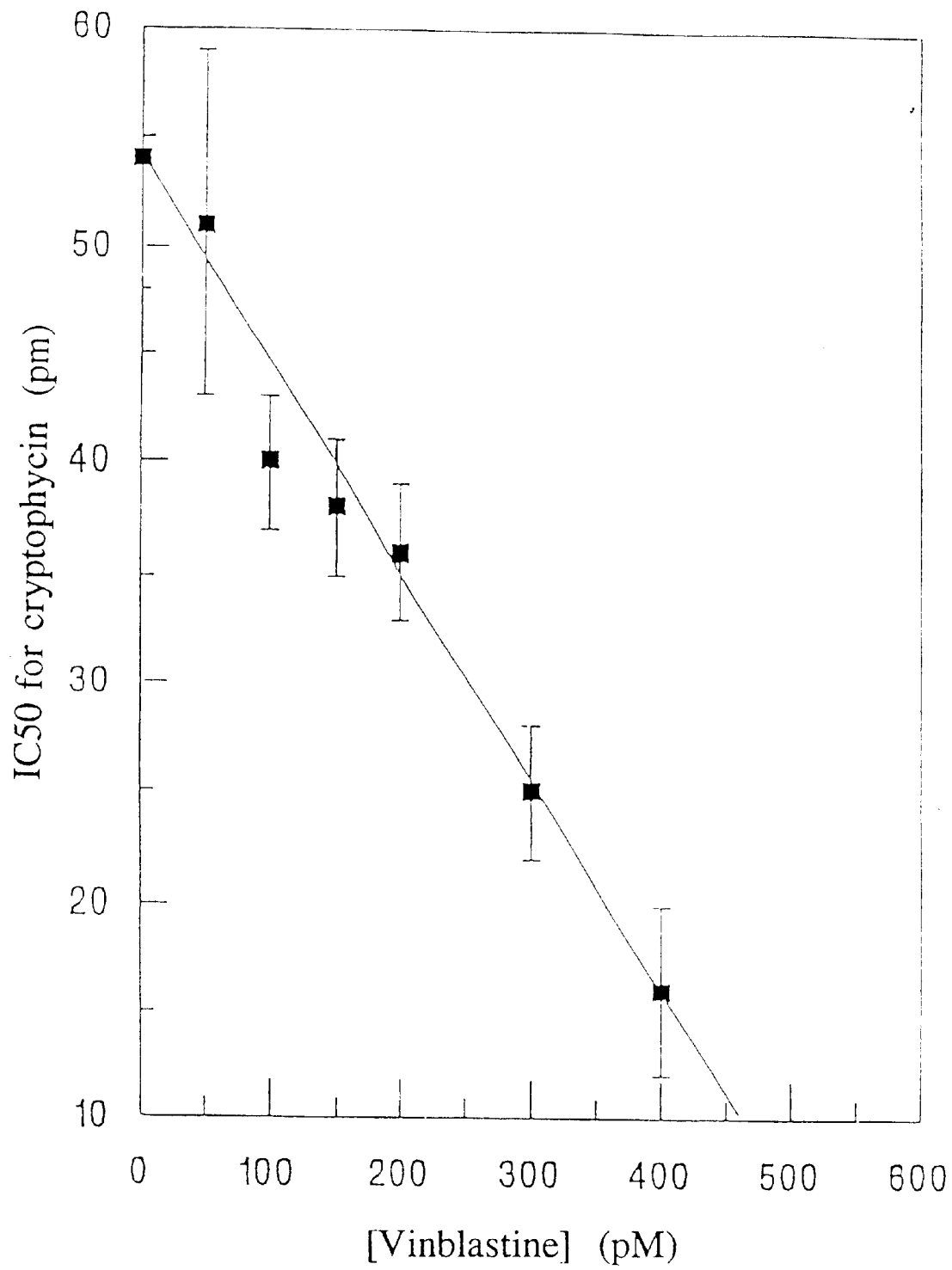
FIG. 4 provides Isobolograms for combinational effects of vinblastine and cryptophycins on cell proliferation. SKOV3 cells were treated with vinblastine (0–600 pM) and/or cryptophycins (1–100 pM) for 48 hours. Cell numbers were then determined by SRB staining as described in the Experimental Section, and the $IC_{50}$s (■) and the line of additivity (- - -) for combinations of vinblastine and cryptophycin compounds. Values represent the means for two experiments each containing triplicate samples.
Figure 5:
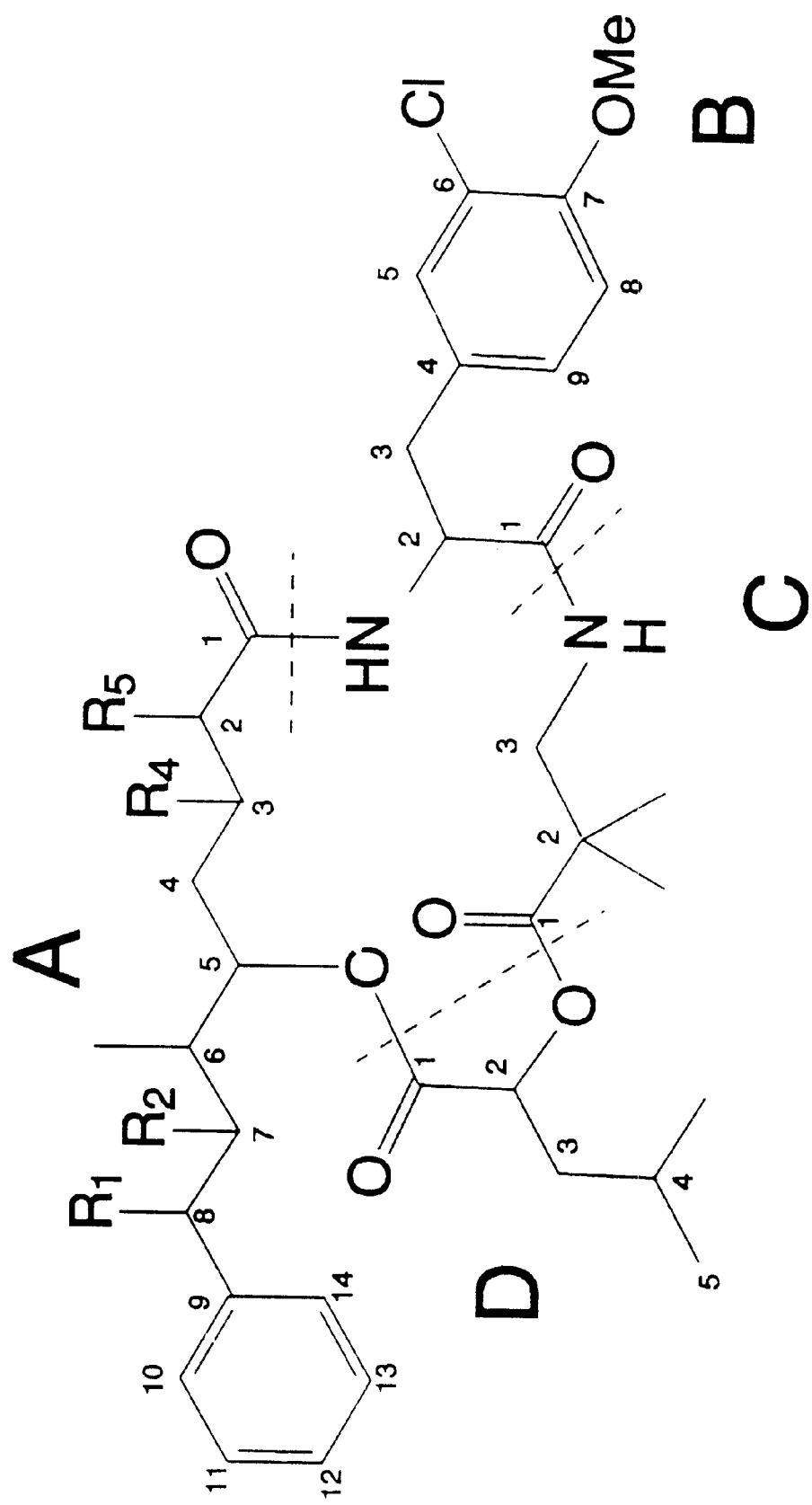
FIG. 5 provides a general structure of selected cryptophycin compounds of the present invention produced via total synthesis and a numbering system for the hydroxy acid units A and D and two amino acid units B and C some of the selected embodiments.
Figure 6:
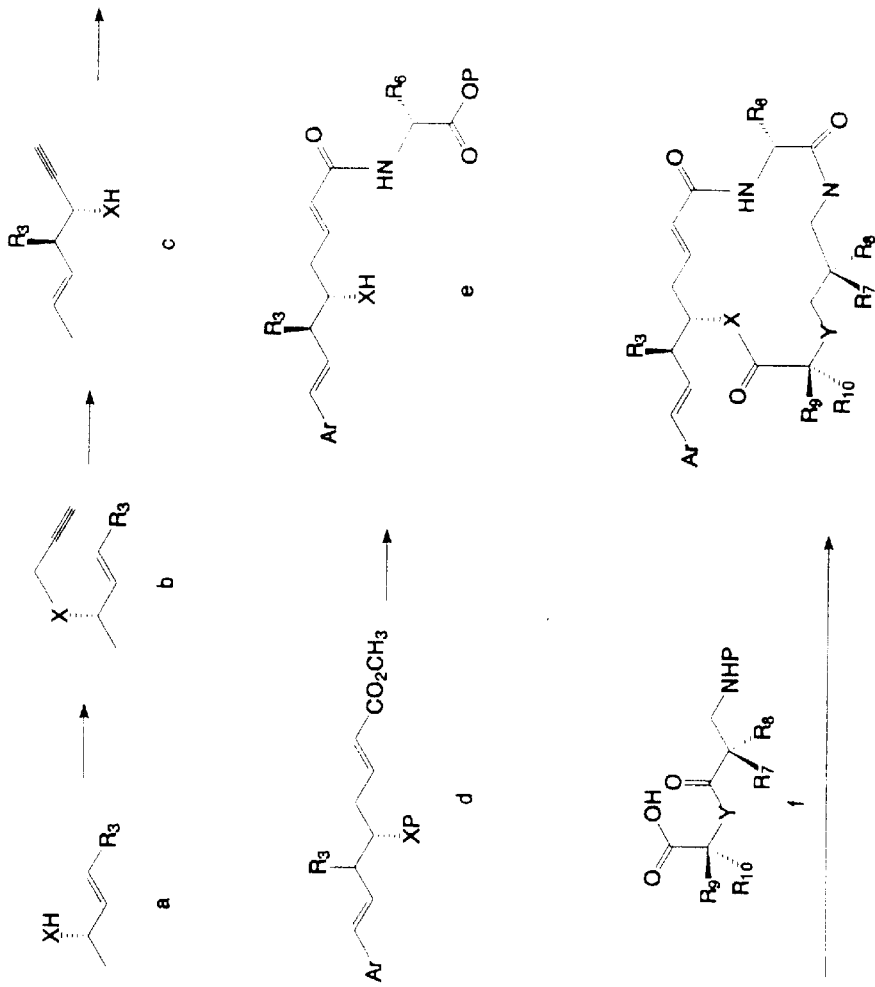
FIG. 6 provides a first scheme for synthesizing a cryptophycin.
Figure 7:
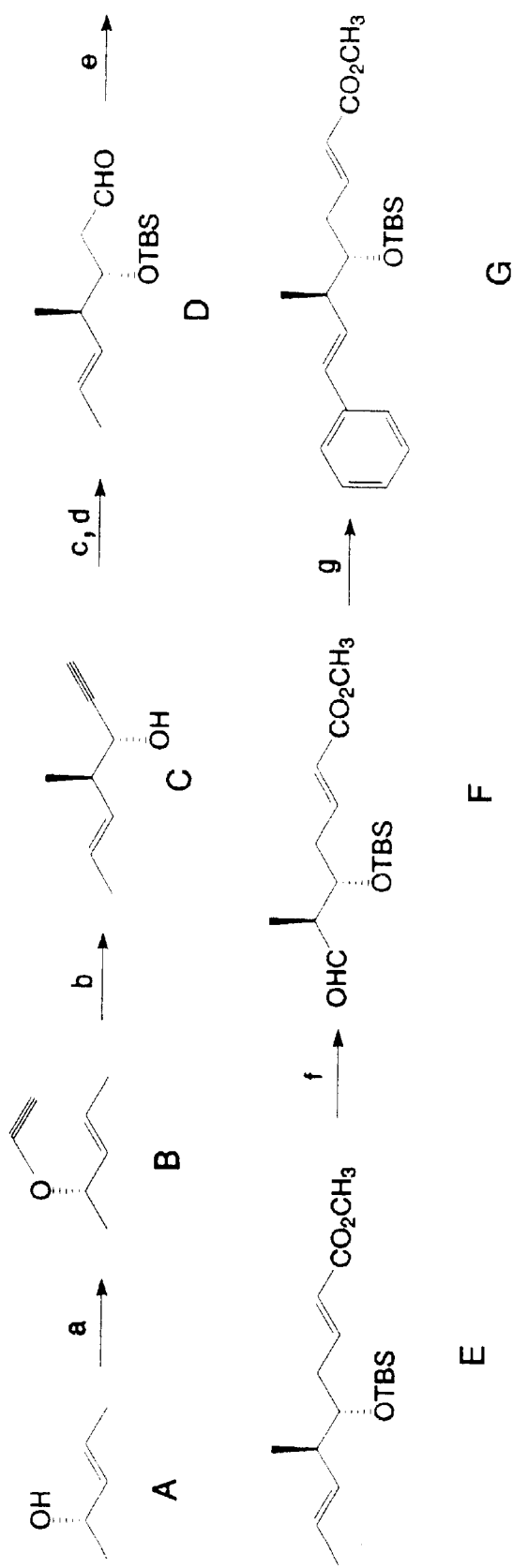
FIG. 7 provides a scheme for producing a hydroxy unit A.
Figure 8:
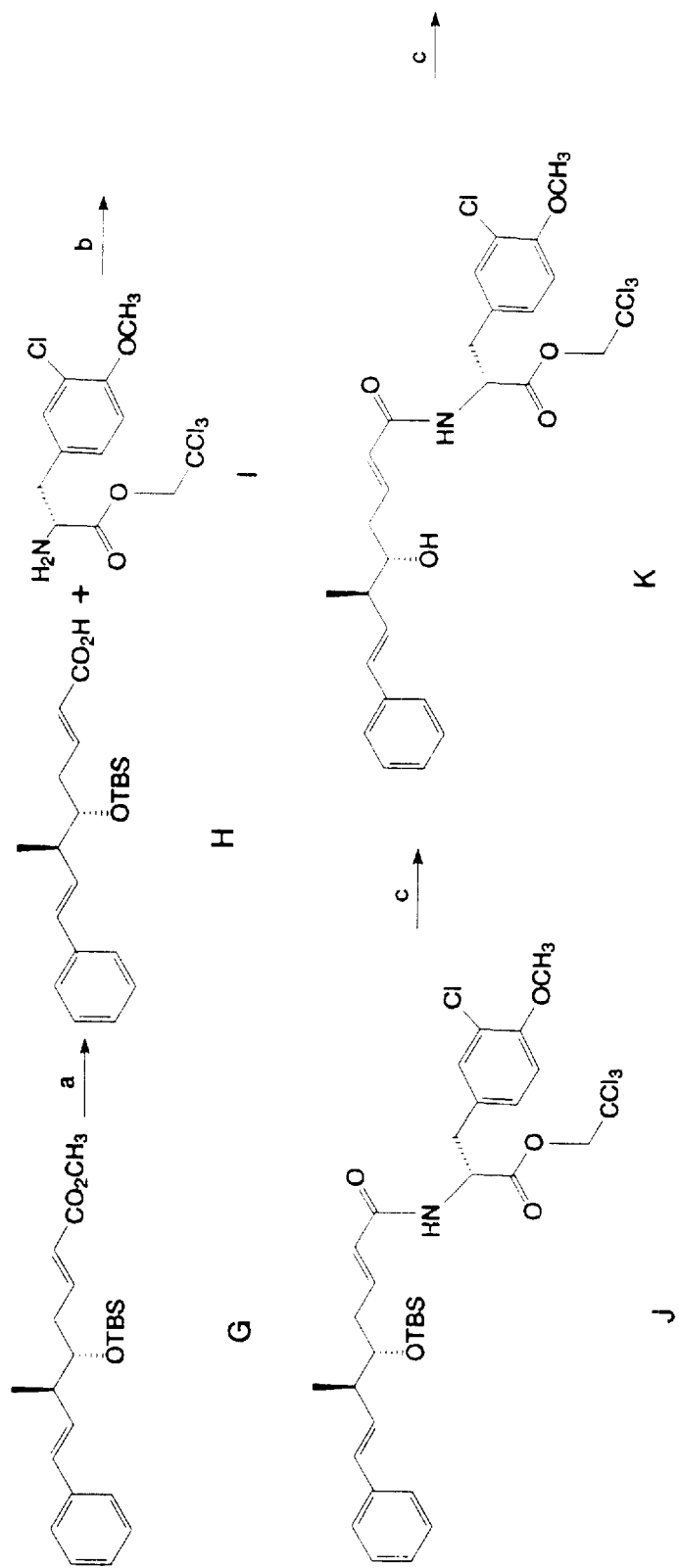
FIG. 8 provides a scheme for producing the subunit of a cryptophycin comprising s hydroxy acid unit A and amino acid B.
Figure 9:
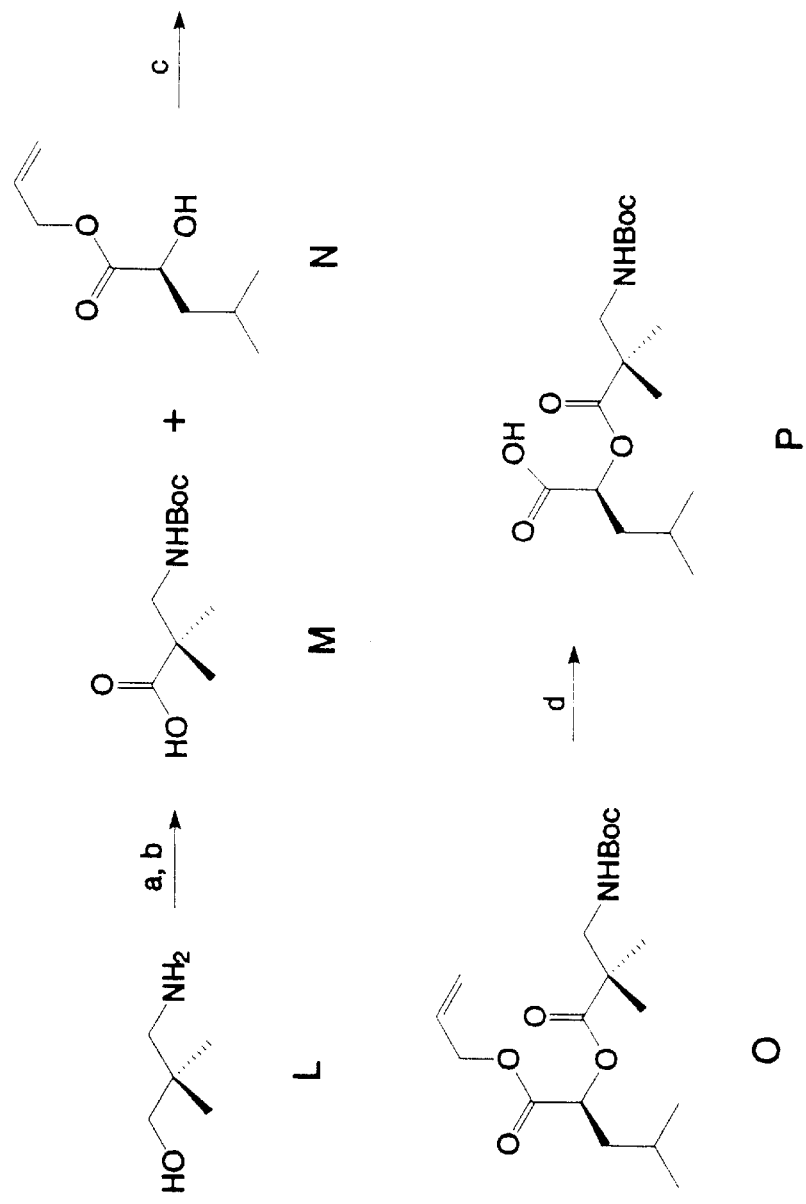
FIG. 9 provides a scheme for producing the subunit of a cryptophycin comprising an amino acid unit C and hydroxy acid D.
Figure 10:
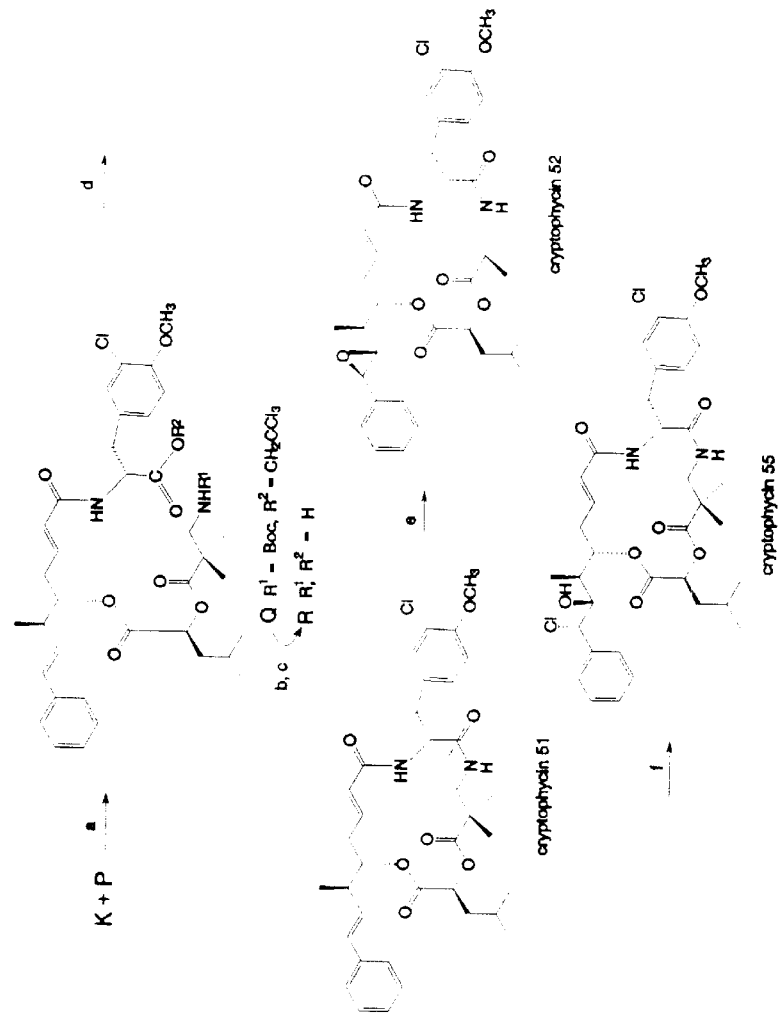
FIG. 10 provides a scheme for producing cryptophycins 51, 52 and 55.

SKOV3 cells were treated with combinations of cryptophycins and vinblastine for 48 hours. The percentages of surviving cells were then determined and the $IC_{50}$s for each combination was calculated. The effects of these combinational treatments, as well as single drug treatments, are depicted as an isobologram (FIG. 4). The $IC_{50}$s for combinations of cryptophycin compounds and vinblastine fell very close to the line of additivity, indicating that these two drugs induce only additive inhibitions of cell proliferation.

Toxicity of cryptophycins, vinblastine and taxol toward SKOV3 and SKVLB1 cells

SKVLB1 cells are resistant to natural product anticancer drugs because of their over expression of P-glycoprotein[12]. The abilities of taxol, vinblastine and cryptophycin compounds to inhibit the growth of SKOV3 and SKVLB1 cells are summarized in Table 5. Taxol caused dose-dependent inhibition of the proliferation of both cells lines with $IC_{50}$s for SKOV3 and SKVLB1 cells of 1 and 8000 nM, respectively. Vinblastine also inhibited the growth of both cell lines, with $IC_{50}$s of 0.35 and 4200 nM for SKOV3 and SKVLB1 cells, respectively. Cryptophycins demonstrated $IC_{50}$s of 7 and 600 pM for SKOV3 and SKVLB1 cells, respectively. The resulting resistance factors for SKVLB1 cells to the compounds are calculated as the $IC_{50}$s for SKVLB1. $IC_{50}$s for SKOV3 cells are also indicated in Table 5.

TABLE 5

Cytotoxicities of antimitotic agents for SKOV3 and SKVLB1 cells

Cells were treated with varying concentrations of the compounds indicated below for 48 hours. Cells numbers were then determined as indicated in the Methods section and the $IC_{50}$ for each compound was calculated. Values represent the main ±SEM for three experiments.

|  | Cell Line | | |
| --- | --- | --- | --- |
| Compound | SKOV3 | SKVLB $IC_{50}$ (nM) | Resistance Factor |
| Vinblastine | 0.35 ± 0.25 | 4200 ± 1700 | 12,000 |
| Taxol | 1 ± 0.4 | 8000 ± 2000 | 8,000 |
| Cryptophycins | 0.007 ± 0.002 | 0.60 ± 0.19 | 86 |

Thus it is demonstrated that the present invention provides novel cryptophycin compounds, as well as previously-disclosed cryptophycin compounds, which are potent inhibitors of cell proliferation, acting by disruption of the microtubule network and inhibition of mitosis. The cryptophycin compounds disrupt microtubule organization and thus normal cellular functions, including those of mitosis.

Classic anti-microtubule agents, such as colchicine and Vinca alkaloids, arrest cell division at mitosis. It seemed appropriate to compare the effect of one of these agents on cell proliferation with the cryptophycin compounds. For this purpose, the Vinca alkaloid vinblastine was selected as representative of the classic anti-microtubule agents. Accordingly, the effect of cryptophycin compounds and vinblastine on the proliferation and cell cycle progression of the Jurkat T-cell leukemia cell line was compared. Both compounds caused parallel dose-dependent inhibitions of cell proliferation and accumulation of cells in mitosis.

Since antimitotic effects are commonly mediated by disruption of microtubules in the mitotic spindles, the effects of cryptophycin compounds on cytoskeletal structures were characterized by fluorescence microscopy. Immunofluorescence staining of cells treated with either a cryptophycin compound or vinblastine clearly demonstrated that both compounds caused the complete loss of microtubules. Similar studies with SKOV3 cells demonstrate that the anti-microtubule effects of cryptophycin compounds are not unique to the smooth muscle cell line. Neither drug affected the levels or distribution of microfilament bundles, as was readily induced by cytochalasin B, indicating that the loss of microtubules may not be due to a non-specific mechanism, e.g. activation of proteases or loss of energy charge. Both vinblastine and cryptophycin compounds also promote marked collapse of vimentin intermediate filaments, such that brightly staining rings were formed around the cell nucleus.

Removal of vinblastine from the culture medium resulted in rapid repolymerization of microtubules. In contrast, cells treated with cryptophycin compounds remained depleted of microtubules for at least 24 hours after the compound was removed from the cultures.

The present invention demonstrates that cryptophycin compounds circumvent P-glycoprotein-mediated multiple drug resistance. Transport by P-glycoprotein limits the ability of natural product anticancer drugs to inhibit the growth of tumor cells with acquired or de novo drug resistance.[13–15] Vinca alkaloids, while very useful in the initial course of chemotherapy, are extremely good substrates for transport by P-glycoprotein, and so are of very limited usefulness against P-glycoprotein-mediated MDR tumors. Therefore, identification of agents which overcome multiple drug resistance may, should lead to the development of useful and novel anticancer agents. The cryptophycin compounds of the present invention appear to be such agents since they are poor substrates for P-glycoprotein-mediated transport. This fact is reflected in the low cell resistance factor for cryptophycin compounds compared with vinblastine, taxol and other natural product drugs.

Total Synthesis of Cryptophycins

The structures of the novel synthesized compounds, viz. Cryptophycins 51, 52, 53, 55, 56, 57, 58, and 61 were confirmed in a straightforward manner using methodology that is well-known to those trained in the art. Mass spectral data were consistent with the molecular compositions. Proton and carbon NMR data were very similar to those of cryptophycin 1 and related naturally-occurring and semi-synthetic analogs.

The following examples demonstrate the total syntehsis of cryptophycin compounds as well as their use as therapeutic agents in accordance with the invention.

EXAMPLE 11

Synthesis of Cryptophycin 51

S-trans-3-Penten-2-ol (A)

A mixture of racemic trans-3-penten-2-ol (933 mg, 11 mmol), trifluoroethyl laurate (4.14 g, 15 mmol), and porcine pancreatic lipase (PPL, 2.0 g) in 25 ml of anhydrous diethyl ether was stirred for 80 hours. The PPL was then filtered off and washed with ether three times. The ether filtrate was evaporated and the sticky oil was then subjected to short-path vacuum distillation. The S-trans-3-penten-2-ol (A) was condensed in a liquid nitrogen cooled trap (383 mg). $^1$H NMR (CDCl$_3$) d 5.57 (4-H; dq, −15.3/6.0), 5.47 (3-H; ddd, −15.3/6.4/1.2), 4.19 (2-H; 1:4:6:4:1 pentuplet, 6.4), 2.24 (OH; bs), 1.63 (5-H$_3$; d, 6.0), 1.19 (1-H$_3$; d, 6.4). $^{13}$C NMR (CDCl$_3$) d 135.5 (3), 125.5 (4), 68.7 (2), 23.3 (5), 17.5 (1).

S-trans-2-(2-Propynloxy)-3-pentene (B)

To a vigorously stirred mixture of S-enantiomer A (628 mg, 7.3 mmol), tetrabutylammonium hydrogen sulfate (138 mg, 0.41 mmol), and 40% NaOH in water (5 mL) at 0° C. was added dropwise propargyl chloride (767 mg, 10.3 mmol, 745 μL). Vigorous stirring was continued overnight after which time the mixture was neutralized by HCl at 0° C. and the propargyl ether extracted into pentane. The extract was evaporated and the propargyl ether was purified on a short silica gel column (2% diethyl ether/pentane) to give 778 mg of propargyl ether B, $[\alpha]_D$-118.9° (c 2.0, $CHCl_3$); $^1H$ NMR ($CDCl_3$) d 5.70 (4-H; dq, 18.5/6.5), 5.31 (3-H; ddd, 18.5/7.2/1.4), 4.15 (1'-H; dd, −15.6/2.1), 4.01 (1'-H; dd, −15.6/2.1), 4.01 (2-H; m), 2.38 (3'-H; t, 2.1), 1.73 (5-H; dd, 6.5/1.4), 1.25 (1H; d, 6.3).

(3R,4R)-4-Methylhept-5(E)-en-1-yn-3-ol (C)

An aliquot of butyl lithium hexane solution (2.5 M, 5.1 ml, 12.8 mmol) was evaporated in vacuo and the residue cooled to −90° C. A solution of propargyl ether B (454 mg, 3.66 mmol) in 10 ml of THF was slowly added. After allowing the temperature to increase to room temperature overnight, the reaction mixture was quenched with $NH_4Cl$ solution. Extraction with ether three times, evaporation of the dried extract, and purification of the residue on a silica gel column (5% EtOAc/hexane) gave 322 mg of alcohol C (71% yield), $[\alpha]_D$+32.9° (c 3.0, $CHCl_3$); IR (NaCl) $n_{max}$ 3306, 2968, 1455, 1379, 1029, 975 $cm^{-1}$. $^1H$ NMR ($CDCl_3$) d 5.61 (6-H; dq, 15.3/6.3), 5.38 (5-H; dd, 15.3/7.7), 4.13 (3-H; bs), 2.45 (1-H; d, 1.5), 2.38 (4-H; m), 2.20 (OH; bd, 3.3), 1.68 (7-H; d, 6.2), 1.09 (4-$CH_3$; d, 6.8). $^{13}C$ NMR ($CDCl_3$) d 131.5 (5), 127.9 (6), 83.5 (2), 73.6 (1), 66.2 (3), 43.4 (4), 18.1 (7), 15.7 (4-Me).

(3S,4R)-3-tert-Butyldiphenylsilyloxy-4-methylhept-5E-enal (D)

To a stirred solution of alcohol C (248 mg, 2 mmol) and imidazole (340 mg, 5 mmol) in 3 mL of dry DMF was added tert-butyldimethylsilyl chloride (452 mg, 3 mmol). After stirring the mixture overnight, 10 mL of 10% NaOH was added to destroy the excess tert-butyldimethylsilyl chloride. The product was extracted into ether and the extract washed successively with water, 0.5 N HCl, and water, dried and evaporated. Purification of the residue by chromatography on silica gel with hexane gave 457 mg of (3R,4R)-3-tert-butyldimethylsilyloxy-4-methylhept-5(E)-en-1-yne (96% yield), $^1H$ NMR ($CDCl_3$) d 5.50 (6-H; dq, 15.3/6.1), 5.38 (5-H; dd, 15.3/7.5), 4.16 (3-H; dd, 5.7/1.7), 2.37 (1-H; d, 1.7), 2.35 (4-H; m), 1.68 (7-H; d, 6.1), 1.07 (4-Me; d, 6.8), 0.90 ($CMe_3$; s), 0.12 (SiMe; s), 0.09 (SiMe; s).

Using the same procedure the corresponding TBDPS derivative, (3R,4R)-3-tert-butyldiphenylsilyloxy-4-methylhept-5(E)-en-1-yne, was formed in 92% yield, $[\alpha]_D$+32.9° (c 3.0, $CHCl_3$). $^1H$ NMR ($CDCl_3$) d 7.72/7.38 (2Ph-$H_5$), 5.32 (6-H; m), 5.25 (5-H; dd, 16.2/7.3), 4.29 (3-H; dd, 5.2/2.0), 2.38 (4-H; m), 2.33 (1-H; d, 2.0), 1.64 (7-H; d, 5.3), 1.11 (4-Me; d, 6.9), 1.06 ($CMe_3$). $^{13}C$ NMR ($CDCl_3$) d 136.1/135.9/133.6/129.7/129.6/127.5/127.3 (Ph), 132.4 (5), 126.1 (6), 83.3 (2), 73.5 (1), 68.0 (3), 43.6 (4), 26.9 ($C\underline{Me}_3$), 19.4 ($\underline{C}Me_3$), 18.0 (7), 14.7 (4-Me).

2-Methylbutene (1.15 mL 2M solution in THF, 2.3 mmol) was added to 1.1 mL of $BH_3$ THF solution (1M, 1.1 mmol) at −25° C. and the mixture was stirred in an ice bath for two hours. The temperature was then cooled to −50° C. and a solution of the TBS derivative (238 mg, 1 mmol) in 1 ml of THF was added all at once. The cooling bath was removed and the reaction mixture was allowed to warm to and remain at room temperature for one hour. Then 2.2 M $KH_2PO_4$/$K_2HPO_4$ solution (4.8 mL) and 30% $H_2O_2$ (0.8 mL) were added at 0° C. One hour later, the THF was evaporated and the residue was extracted into ether. The dried ether extract was evaporated and the residue chromatographed on silica gel (1% EtOAc/hexane) to give 194 mg of aldehyde D (76% yield). $^1H$ NMR ($CDCl_3$) d 9.78 (1-H; t, 2.3), 5.46 (6-H; dq, 15.3/6.1), 5.34 (5-H; dd, 15.3/7.5), 4.13 (3-H; m), 2.47 (2-H; m), 2.31 (4-H; m), 1.66 (7-H; br d, 6.1), 0.99 (4-Me; d, 6.8), 0.87 ($CMe_3$; s), 0.07 (SiMe; s), 0.04 (SiMe; s).

The tert-butyldimethylsilyl ether (TBDMS) derivative of the aldehyde was formed in 83% yield, $^1H$ NMR ($CDCl_3$) d 9.52 (1-H; t, 2.4), 7.69/7.40 (2Ph-$H_5$), 5.28 (6-H; m), 5.22 (5-H; dd, 16.2/6.2), 4.19 (3-H; m), 2.42 (2-H; m), 2.29 (4-H; m), 1.60 (7-H; d, 5.4), 1.07 ($CMe_3$), 1.02 (4-Me; d, 6.9). $^{13}C$ NMR ($CDCl_3$) d 202.0 (1), 136.1/133.6/133.3/130.2/129.7/127.7/127.6 (Ph), 132.3 (5), 126.2 (6), 72.8 (3), 47.6 (2), 42.2 (4), 27.1 ($C\underline{Me}_3$), 19.6 ($\underline{C}Me_3$), 18.3 (7), 14.9 (4-Me).

Methyl (5S,6R)-5-tert-Butyldimethylsilyloxy-6-methyl-7-oxonon a-2E,7E-dienoate (E)

To a stirred solution of aldehyde D (0.74 g, 2.9 mmol) and trimethyl phosphonoacetate (632 mg, 3.5 mmol) in 5 mL of THF cooled to −78° C. was added tetramethylguanidine (435 μL, 3.5 mmol). After 30 minute the cooling bath was removed and the mixture was stirred for another four hours. The mixture was neutralized with 1N HCl and the product was extracted into ether. Evaporation of the dried ether extract left a residue which was chromatographed on silica gel (5% EtOAc/hexane) to give 0.814 g of E (90% yield). $^1H$ NMR ($CDCl_3$) d 6.93 (3-H;dt, 15.6/7.8), 5.62 (2-H; dd, 15.6/1.2) 5.37 (8-H, m), 5.37 (7-H, m), 3.71 ($OCH_3$, s), 3.61 (5-H, m), 2.29 (4-$H_2$, m), 2.22 (6-H, m), 1.66 (9-$H_3$; br d, 6.1), 0.99 (6-Me; d, 6.8), 0.88 ($CMe_3$; s), 0.03 (SiMe; s), 0.01 (SiMe, s).

The tert-butyldimethylsilyl ether (TBDMS) derivative of the aldehyde was formed in 90% yield, $^1H$ NMR ($CDCl_3$) d 7.68/7.38 (2Ph-$H_5$), 6.75 (3-H;dt, 15.6/7.4), 5.62 (2-H; d, 15.6), 5.34 (8-H, m), 5.29 (7-H, m), 3.70 (5-H, m), 3.68 ($OCH_3$, s), 2.28 (4-$H_2$, m), 2.20 (6-H, m), 1.62 (9-$H_3$; d, 5.3), 1.08 ($CMe_3$), 0.99 (6-Me; d, 6.9). $^{13}C$ NMR ($CDCl_3$) d 166.7 (1), 146.4 (3), 136.0/134.2/133.8/129.62/129.56/127.5/127.4 (Ph), 132.5 (7), 125.8 (8), 122.6 (2), 76.2 (5), 51.3 ($OCH_3$), 41.7 (6), 36.8 (4), 27.0 ($C\underline{Me}_3$), 19.4 ($\underline{C}Me_3$), 18.1 (9), 14.7 (6-Me).

Methyl (5S,6R)-5-tert-Butyldimethylsilyloxy-6-methyl-7-oxohep t-2(E)-enoate (F)

Ozone was passed through a solution of methyl ester E (328 mg, 1.0 mmol) and 97 μL of pyridine in 15 mL of $CH_2Cl_2$ at −78° C. and the progress of the ozonolysis was monitored by TLC analysis. After the methyl ester had been consumed, about 500 mg if zinc dust and 1 mL of glacial acetic acid were added. The temperature was slowly increased to 25° C. The mixture was filtered and the filtrate was washed successively with saturated $CuSO_4$ and $NaHCO_3$ solutions. After evaporation of the solvent, the crude aldehyde F (249 mg, 83%) in the next step without further purification. $^1H$ NMR ($CDCl_3$) d 9.96 (7-H; t, 2.3), 6.96 (3-H; dt, 15.7/7.6), 5.90 (2-H; dd, 15.7/0.7), 4.05 (5-H; m), 3.74 (OMe; s), 2.51 (6-H; m), 2.45 (4-$H_2$; m), 1.09 (6-Me; d, 6.9), 0.88 ($CMe_3$; s), 0.04 (SiMe; s), 0.03 (SiMe; s).

Methyl (5S, 6R)-5-t-butyldimethylsilyloxy-6-methyl-8-phenyl-oc ta-2E,7E-dienoate (G)

To a stirred solution of aldehyde 5 (25.0 mg, 0.08 mmol) in 1.5 mL of THF at −78° C. was added 0.80 mL of a cold (−78° C.) mixture of benzyltriphenylphosphonium chloride (268 mg, 0.69 mmol, in 6.9 mL of THF) and n-butyl lithium (280 μL, 2.5 M in hexane). After 15 min, the cold bath was removed and stirring was continued for 2 h. The reaction was quenched with saturated ammonium chloride solution and the THF was evaporated. The concentrate was extracted with hexane twice and the combined extract was washed with brine, dried and evaporated. The residual oil, a 5:1 mixture of the E and Z isomers, was dissolved in 1.5 mL of benzene containing thiophenol (0.02M) and 1,1'azobis (cyclohexanecarbonitrile) (VAZO, 0.006M) and the mixture was refluxed for 5 h. After cooling to RT, hexane (15 mL)

was added and the organic solution was washed successively with 10% NaOH and brine, dried (MgSO$_4$), and evaporated. Chromatography of the residue on silica gel (2% EtOAc/hexane) led to 24 mg (80%) of G, [a]$_D$+68.2° (c 1.5, CHCl$_3$); EIMS m/z 374 (<1%; M$^+$), 359 (1; M$^+$-CH$_3$), 317 (10; M$^+$-Bu), 275 (10), 243, (73), 143 (20), 115 (10), 97 (64), 89 (31), 73 (100); HREIMS m/z 374.2232 (C$_{22}$H$_{34}$O$_3$Si, D+4.5 mmu), 359,2031 (C$_{21}$H$_{31}$O$_3$Si, D+1.1 mmu); 317.1579 (C$_{18}$H$_{25}$O$_3$Si, D-0.6 mmu); UV (MeOH) 1$_{max}$ (e) 206 (33500), 252 (20100)nm; IR n$_{max}$ 2952, 2855, 1725, 1657, 1435, 1257, 1168, 1097, 970, 836, 775 cm$^{-1}$; $^1$H NMR d 7.2–7.4 (Ph-H$_5$; m), 6.96 (3-H; ddd, 15.6/7.8/7.5), 6.37 (8-H; d, 15.9), 6.16 (7-H; dd, 15.9/8.1), 5.84 (2-H; d, 15.6), 3.75 (5-H; ddd, 10.2/6.0/4.2), 3.72 (OMe; s), 2.44 (6-H; m), 2.36 (4-H$_2$; m), 1.10 (6-Me; d, 6.9), 0.91 (Si-CMe$_3$; s), 0.06 (Si-Me; s); 0.05 (Si-Me; s); $^{13}$C NMR d 166.8 (1), 146.4 (3), 137.6 (Ph 1'), 131.9 (8), 130.4 (7), 128.5 (Ph 3'/5'), 127.0 (Ph 4'), 126.0 (Ph 2'/6'), 122.9 (2), 75.0 (5), 51.4 (OMe), 42.8 (6), 37.6 (4), 25.9 (Si-C$\underline{Me}$$_3$), 18.1 (Si-$\underline{C}$Me$_3$), 16.2 (6-Me), −4.4 (Si-Me), −4.5 (Si-Me). Calcd for C$_{22}$H$_{34}$O$_3$Si: C, 70.52; H, 9.17. Found:, C, 70.72; H, 9.42.

(5S,6R)-5-t-Butyldimethylsilyloxy-6-methyl-8-phenylocta-2E,7E-dienoic acid (H)

To a solution of ester G (159 mg, 0.43 mmol) in 7 mL acetone was added 5 mL of 1N aq LiOH. The mixture was stirred at 25° C. for 3 h, diluted with 20 mL of Et$_2$O, and acidified to ≈pH 4 with 1N HCl. The organic layer was separated and washed with 20 mL portions of brine and water, dried (MgSO$_4$) and evaporated. Chromatography of the residual oil on silica gel with 40% EtOAc in hexane containing 0.5% AcOH resulted in pure acid H as a pale yellow mobile oil (145 mg, ,95% yield): [a]$_D$+87.0° (c 1.4, CHCl$_3$); EIMS m/z; 343 (1; M$^+$-OH), 303 (5), 275 (9), 257 (4), 229 (62), 213 (16), 171 (22), 143 (37), 131 (16), 115 (23), 97 (100), 91 (44); HREIMS m/z 343.2107 (C$_{21}$H$_{31}$O$_2$Si, D-1.3 mmu), 229.1220 (C$_{15}$H$_{17}$O$_2$, D+0.9 mmu); UV 1$_{max}$ (e) 206 (24500), 252 (15600) nm; IR n$_{max}$ 3300-2800 (br), 2956, 2856, 1697, 1651, 1419, 1256, 1097, 836, 693 cm$^{-1}$; $^1$H NMR d 10.4 (CO$_2$H; bs, W$_{1/2}$≈100), 7.2–7.4 (Ph-H$_5$; m), 7.09 (3-H; ddd, 15.6/7.6/7.6), 6.39 (8-H; d, 15.9), 6.16 (7-H; dd, 15.9/8.1), 5.85 (2-H; d, 15.6), 3.78 (5-H; ddd, 6.0/6.0/4.2), 2.46 (6-H; m), 2.40 (4-H$_2$; m), 1.12 (6-Me; d, 6.9), 0.92 (Si-CMe$_3$; s), 0.07 (SiMe$_2$; s); $^{13}$C NMR d 171.6 (1), 149.1 (3), 137.5 (Ph 1'), 131.8 (8), 130.5 (7), 128.5 (Ph 3'/5'), 127.1 (Ph 4'), 126.1 (Ph 2'/6'), 122.7 (2), 74.9 (5), 42.9 (6), 37.6 (4), 25.8 (Si-C$\underline{Me}$$_3$), 18.1 (Si-$\underline{C}$Me$_3$), 16.1 (6-Me), −4.4 (Si-Me), −4.5 (Si-Me).

2,2,2-Trichloroethyl Ester of 3-(3-Chloro-4-methoxyphenyl)-D-alanine (I)

A sample of the D-chlorotyrosine BOC derivative (160 mg, 0.35 mmol) was dissolved in 3 mL neat trifluoroacetic acid and allowed to stand at room temperature for 1 h. Removal of the excess reagent under reduced pressure returned the desired amine I as the trifluoroacetate salt (165 mg, 100% yield), [a]$_D$+1.7° (c 5.2, CHCl$_3$); IR n$_{max}$ 3400-2500 (br), 1760, 1680, 1500, 1200, 1130, 1070, 805, 710 cm$^{-1}$; $^1$H NMR d 8.07 (NH$_2$; br m, W$_{1/2}$≈45), 7.27 (5-H; s), 7.12 (9-H; d, 8.1), 6.88 (8-H; d, 8.1), 4.86/4.67 (CH$_2$CCl$_3$; AB q, −12.0), 4.41 (2-H; bs, W$_{1/2}$≈20), 3.86 (OMe; s), 3.33 (3-H; dd, −14.4/3.6), 3.22 (3-H'; dd, −14.4/6.6); $^{13}$C NMR d 167.6 (1), 155.0 (7), 130.9 (5), 128.8 (9), 125.4 (4), 123.1 (6), 112.7 (8), 93.4 (CCl$_3$), 75.3 ($\underline{C}$H$_2$CCl$_3$), 56.1 (OMe), 54.2 (2), 34.9 (3).

Compound J

To a stirred solution of H (25 mg, 0.07 mmol) in 3 mL of anhdrous DMF under argon was added successively pentafluorodiphenylphosphinate (FDPP, 32 mg, 0.08 mmol), trifluoroacetate salt I (35 mg, 0.07 mmol) and diisopropylethylamine (DIEA, 27 mg, ≈36 mL, 0.21 mmol, ≈3 equiv). Stirring was continued at 25° C. for 1 h and then the reaction mixture was extracted with 20 mL of Et$_2$O. The ether extract was washed with 10 mL of 1N HCl, followed by 10 mL of sat'd NaHCO$_3$, 20 mL of brine and 20 mL of water, dried (MgSO$_4$), and evaporated. The residual pale yellow oil was subjected to chromatography on silica gel (15% EtOAc in hexane) to give J as a colorless oil (32 gm 65% yield): [a]$_D$+11.8° (c 1.2, CHCl$_3$); EIMS m/z; 644/646/648/650 (7/8/6/3; M$^+$-Bu), 570/572/574 (46/100/21), 536/538 (18/15), 394/396 (67/29), 275 (20), 155/157 (29/9); HREIMS m/z 644.0981 (C$_{29}$H$_{34}$Cl$_4$NO$_5$Si, D-2.1 mmu); UV 1$_{max}$ (e) 204 (54900), 230 (23200), 248 (19200), 284 (3500) nm; IR n$_{max}$ 3290, 2980, 2850, 1760, 1680, 1640, 1505, 1380, 1270, 1169, 990, 720 cm$^{-1}$; $^1$H NMR unit A d 7.2–7.4 (Ph-H$_5$; m), 6.87 (3-H; ddd, 15.0/7.8/7.5), 6.37 (8-H; d, 16.2), 6.18 (7-H; dd, 16.2/8.1), 5.82 (2-H; d, 15.0), 3.75 (5-H; ddd, 9.9/6.0/4.8), 2.46 (6-H; m), 2.36 (4-H$_2$; m), 1.11 (6-Me; d, 6.9), 0.91 (SiCMe$_3$; s), 0.07 (SiMe; s), 0.06 (SiMe; s); unit B d 7.19 (5-H; d, 2.1), 7.04 (9-H; dd, 8.4/2.1), 6.85 (8-H; d, 8.4), 5.85 (NH; d, 7.8), 5.08 (2-H; ddd, 7.8/6.0/5.7), 4.81/4.74 (CH$_2$CCl$_3$; AB q, −11.7), 3.87 (OMe; s), 3.22 (3-H; dd, −14.1/5.7), 3.12 (3-H'; dd, −14.1/6.0). $^{13}$C NMR unit A d 165.1 (1), 143.0 (3), 137.6 (9), 132.0 (8), 130.4 (7), 128.5 (11/13), 127.0 (12), 126.0 (10/14), 124.7 (20, 75.0 (5), 42.6 (6), 37.6 (4), 25.9 (Si-C$\underline{Me}$$_3$), 18.1 (Si-$\underline{C}$Me$_3$), 16.5 (6-Me), −4.3 (Si-Me), −4.6 (Si-Me); unit B d 170.1 (1), 154.3 (7), 131.1 (5), 128.5 (4/9), 122.6 (6), 112.2 (8), 94.2 (CCl$_3$), 74.8 ($\underline{C}$H$_2$CCl$_3$), 56.1 (OMe), 53.0 (2), 36.5 (3).

(1'R,5S,6R)-N-1'-(carbo-2",2",2"-trichloroethoxy)-2'-(3-chloro-4-methoxyphenyl)ethyl 5-t-butyldimethylsilyloxy-6-methyl-8-phenyl-octa-2E,7E-die namide (K)

To a solution of J (50 mg, 0.07 mmol) in 4 mL MeCN was added 400 mL of 49% aq HF and the mixture stirred for 1 h at 25° C. Extraction into 30 mL of Et$_2$O, followed by washing the ether extract with 30 mL portions of sat'd NaHCO$_3$, brine and water, drying (MgSO$_4$) and evaporation, gave alcohol K as a colorless foam (40 mg, 95% yield): [a]$_D$-6.1° (c 1.3, CHCl$_3$); EIMS m/z (rel intensity) 587/589/591/593 (M+, <1%), 552/554/556 (1/2/0.5), 456/458/460/462 (1/2/1/0.2), 342/344/346 (7/8/4), 212/214 (15/5), 195/197 (6/2), 155/157 (99/34), 131 (100), 91 (77); HREIMS m/z 587.0721 (C$_{27}$H$_{29}$$^{35}$Cl$_4$NO$_5$, D+7.9 mmu); UV 1$_{max}$ 204 (56500), 230 (22100), 248 (18100), 284 (3600) nm; IR n$_{max}$ 3400, 3300, 2980, 1780, 1680, 1640, 1505, 1270, 1180, 1090, 1000, 770 cm$^{-1}$. $^1$H NMR unit A d 7.2–7.4 (Ph-H$_5$; m), 6.92 (3-H; ddd, 15.3/7.8/7.5), 6.46 (8-H; d, 15.9), 6.14 (7-H; dd, 15.9/8.4), 5.90 (2-H; d, 15.3), 3.65 (5-H; ddd 7.8/5.6/4.0), 2.39 (6-H/4-H$_2$; bm), 1.78 (OH; bs, W$_{1/2}$≈40 Hz), 1.14 (6-Me; d, 6.9); unit B d 7.18 (5-H; d, 1.8), 7.03 (9-H; dd, 8.4/1.8), 6.84 (8-H; d, 8.4), 5.97 (NH; d, 7.8), 5.06 (2-H; ddd, 7.8/6.0/5.7), 4.79/4.72 (CH$_2$CCl$_3$; AB q, −12.0), 3.86 (OMe; s), 3.20 (3-H; dd, −14.1/5.7), 3.10 (3-H'; dd, −14.1/6.0). $^{13}$C NMR unit A d 165.3 (1), 142.6 (3), 137.0 (9), 131.7 (8), 131.0 (7), 128.5 (11/13), 127.3 (12), 126.1 (10/14), 125.0 (2), 73.8 (5), 43.2 (6), 37.2 (4), 16.8 (6-Me); unit B d 170.2 (1), 154.2 (7), 131.0 (5), 128.4 (9), 128.3 (4), 122.5 (6), 112.2 (8), 94.2 (CCl$_3$), 74.7 ($\underline{C}$H$_2$CCl$_3$), 56.1 (OMe), 53.0 (2), 36.5 (3).

3-(tert-Butoxycarbonyl)amino-2,2-dimethylpropanoic Acid (M)

To a solution of 3-amino-2,2-dimethylpropan-1-ol (L) (3.0 g, 29 mmol) in 51 mL of a 10% solution of triethylamine in MeOH was added di-tert-butyl dicarbonate (6.7 g, 31 mmol) and the mixture was stirred at 25° C. for 1 h. After removal of solvent, the residue was dissolved in CH$_2$Cl$_2$ (30 mL) and the solution was washed twice with 1 M KHSO$_4$ (pH 2) and once with saturated NaCl solution, and dried (MgSO$_4$). Removal of solvent in vacuo afforded 5.8 g (93% yield) of 3-(tert-butoxycarbonyl)amino-2-dimethylpropan-1-ol as a white solid which was directly used for the next step without further purification (>95% pure by NMR analysis), mp 70.5–71.5° C.; IR n$_{max}$ 3350, 1685, 1456 cm$^{-1}$; $^1$H NMR d 4.87 (NH; br s), 3.72 (OH; br s), 3.19 (1-H$_2$; d, 5.1), 2.95 (3-H$_2$; d, 6.0), 1.44 (CMe$_3$; s), 0.85 (2-Me$_2$; s); $^{13}$C NMR (CDCl$_3$) d 157.6 (BOC CO), 79.7 (CMe$_3$) 68.1 (1), 47.1 (3), 36.7 (2), 28.3 (CMe$_3$), 22.4 (2-Me$_2$).

To a solution of alcohol 3-(tert-butoxycarbonyl)amino-2,2-dimethylpropan-1-ol (5.3 g, 25.9 mmol) and sodium periodate (16.6 g, 77.7 mmol) in carbon tetrachloride (52 mL), acetonitrile (52 mL) and water (78 mL) was added ruthenium trichloride hydrate (122 mg), and the mixture was stirred at 25° C. for 1 h. The mixture was filtered through Celite and a saturated solution of potassium carbonate in water (50 mL) was added. The water layer was separated, washed with ether (20 mL), acidified with HCl to pH 2 at 0° C. and extracted with CH$_2$Cl$_2$ (30 mL×3). The combined extracts ware washed with saturated NaCl solution and dried (MgSO$_4$). Removal of solvent in vacuo yielded a residue that was first subjected to flash reversed-phase chromatography on a C18 silica (ODS 120A, 50 to 90% MeOH) and then crystallized from ether to give 3.7 g (66% yield) of M as a white solid, mp 106–108° C; EIMS m/z (rel intensity) 217 (0.1), 161 (11), 98 (25), 88 (71), 57 (100); HREIMS m/z 217.1292 (C$_{10}$H$_{19}$NO$_4$, D+2.2 mmu); IR n$_{max}$ 3450-2500, 1710, 1694, 1510 cm$^{-1}$; $^1$H NMR of major conformer d 5.03 (NH; br s), 3.26 (3-H$_2$; m), 1.45 (CMe$_3$; s), 1.24 (2-Me$_2$; s); $^{13}$C NMR (CDCl$_3$) d 183.2 (1), 156.3 (BOC CO), 79.6 (CMe$_3$), 49.5/47.9 (2/3), 28.4 (CMe$_3$), 22.9 (2-Me$_2$).

Allyl (2S)-2-Hydroxy-4-methylpentanoate (N)

To a solution of 2.66 gram of L-leucic acid (20 mmol) and 1.74 gram of sodium bicarbonate (20 mmol) in 30 mL water at 0° C. was added 30 mL of a CH$_2$Cl$_2$ solution of 6.44 g of tetrabutylammonium chloride (20 mmol) and 1.74 mL of allyl bromide (20 mmol). After vigorously stirring the mixture for 24 h, the CH$_2$Cl$_2$ was evaporated. About 50 mL water was added and the aqueous layer was extracted four times with Et$_2$O. The ether solution was dried over anhydrous sodium sulfate and then evaporated. The residue was passed through a short Si column to give 3.21 g of allyl ester N (93% yield) as a colorless oil, [a]$_D$-8.4° (c 1.1, CHCl$_3$); IR n$_{max}$ 3464, 2957, 1732, 1203, 1140, 1087 cm$^{-1}$; $^1$H NMR d 5.92 (allyl 2-H; m), 5.34 (allyl 3-H$_Z$; dd, 17.4/1.1), 5.28 (allyl 3-H$_E$; dd, 10.5/1.1) 4.67 (allyl 1-H$_2$; d, 5.7), 4.23 (2-H; br s), 2.64 (OH; br s), 1.89 (4-H; m), 1.57 (3-H$_2$; m), 0.96 (5-H$_3$; d, 6.5), 0.95 (4-Me; d, 6.7); $^{13}$C NMR d 175.3 (1), 131.4 (allyl C-2), 118.6 (3), 68.9 (2), 65.7 (allyl C-1), 43.2 (3), 24.1 (4), 23.0 (5), 21.3 (4-Me).

Allyl (2S)-2-[3'(tert-Butoxycarbonyl)amino-2',2'-dimethylpropa noyloxy]-4-methylpentanoate (O)

To a solution of 0.8 g of M (3.7 mmol), 0.76 g of N (4.4 mmol), and 92 mg DMAP in 10 mL of dry CH$_2$Cl$_2$ at 0° C. was added 0.84 g of DCC (4.1 mmol) in CH$_2$Cl$_2$. The mixture was stirred at 25° C. for 3 h and filtered. The filtrate was washed with saturated aqueous sodium bicarbonate, dried (Na$_2$SO$_4$), and evaporated in vacuo. Flash chromatography (silica gel, 5% EtOAc/hexane) afforded 1.0 g (92% yield) of pure O as a colorless oil, R$_f$ 0.68 (17:83 EtOAc/hexane), [a]$_D$-29.4° (c 18.1, CHCl$_3$); EIMS m/z (rel intensity) 371 (2, M$^+$), 242 (13), 184 (12), 126 (20), 84 (100); HREIMS m/z 371.2317 (C$_{19}$H$_{33}$NO$_6$, D-0.9 mmu); IR (neat) n$_{max}$ 3385, 2963, 1731, 1720, 1513 cm$^{-1}$; $^1$H NMR (300 MHz, CDCl$_3$) unit C d 5.39 (NH; obscured br s), 3.33 (3-H; dd, -13.5/7.4), 3.27 (3-H$^1$; dd, -13.5/5.9), 2.78 (2-H, m), 1.44 (CMe$_3$; s) 1.23 (2-Me; s), 1.22 (2-Me; s); unit D d 5.91 (allyl 2-H ddt, 16.6/10.3/6.0 Hz), 5.34 (allyl 3-H$_Z$; bd, 16.6), 5.27 (allyl 3-H$_E$; bd, 10.3), 5.08 (2-H; dd, 9.6/3.6), 4.65 (allyl 1-H$_2$; m), 1.6–1.9 (3-H$_2$/4-H; M), 0.94 (5-H$_3$; d, 6.3), 0.94 (4-Me; d, 7.3). $^{13}$C NMR unit C d 176.5 (1), 156.3 (BOC CO), 79.0 (CMe$_3$), 48.6 (3), 44.0 (2), 28.4 (CMe$_3$), 22.2/23.0 (2-Me$_2$); unit D d 170.6 (1), 131.4 (allyl C-2), 119.1 (allyl C-3), 70.9 (2), 66.0 (allyl C-1), 39.5 (3), 24.8 (4), 23.0 (5), 21.5 (4-Me).

(2S)-2-[3'(tert-Butoxycarbonyl)amino-2',2'-dimethylpropanoyl oxy]-4-methylpentanoic Acid (P)

To 10 mL of a solution of 180 mg (0.49 mmol) of O and 60 mg (0.05 mmol) of tetrakis(triphenylphosphine)palladium in dry THF (under argon atmosphere) was slowly added 470 mL (5.4 mmol) of dry morpholine over 10 min. After stirring for 50 min, 40 mL of ether was added and the solution was washed with 1N HCl (40 mL). and then extracted with saturated sodium bicarbonate (2×30 mL). The aqueous extract was acidified with 0.5 N HCl and extracted with ether (40 mL). The ether extract was washed with water (2×30 mL), dried (MgSO$_4$) and evaporated in vacuo to give P as a colorless mobile oil (152 mg, 95%); [a]$_D$-22.2° (c 2.2, CHCl$_3$); EIMS m/z (rel intensity) 331 (1, M$^+$), 275 (1), 258 (4), 231 (9), 202 (36), 174 (13), 144 (31), 126 (16), 114 (14), 98 (54), 88 (50), 84 9100); HREIMS m/z 331.2004 (C$_{16}$H$_{29}$NO$_6$, D-1.0 mmu). $^1$H NMR (CDCl$_3$) unit C d 5.41 (NH; dd, 5.7/5.4), 3.30 (3-H$_2$; m), 2.68 (2-H; m), 1.43 (CMe$_3$; br s), 1.22 (2-Me; s), 1.21 (2-Me; s); unit D d 6.47 (1-OH; br s, W$_{1/2}$≈35), 5.09 (2-H; dd, 9.3/2.7), 1.7–1.9 (3-H$_2$/4-H; m), 0.97 (5-H$_3$; d, 6.0), 0.94 (4-Me; d, 6.0). $^{13}$C NMR (CDCl$_3$) unit C d 176.5 (1), 156.5 (BOC CO), 79.3 (CMe$_3$), 48.6 (3), 44.0 (2), 28.3 (CMe$_3$), 23.0 (2-Me), 22.2 (2-Me); unit D d 175.4 (1), 70.6 (2), 39.5 (3), 24.8 (4), 23.0 (5), 21.4 (4-Me).

Compound Q

To a solution of alcohol K (80 mg, 0.14 mmol), acid P (68 mg, 0.21 mmol) and DMAP (4 mg) in dry CH$_2$Cl$_2$ (4 mL) stirred at 0° C. under an argon atmosphere was added DCC (44 mg, 0.21 mmol) in dry CH$_2$Cl$_2$ (1 mL). The mixture was stirred at 0° C. for 30 minutes, during which time a white precipitate developed, and then allowed to warm to room temperature and stirred for a further 4 hours. The precipitate was filtered off and the filtrate diluted with Et$_2$O (40 mL) and washed successively with dilute HCl (1M, 40 mL), saturated NaHCO$_3$ (40 mL) and brine (40 mL). The ethereal layer was dried (MgSO$_4$) and evaporated in vacuo to give a waxy solid. Chromatography (silica, EtOAc:hexane, 1:3) led to pure Q as a colorless, viscous oil (103 mg, 84%), [a]$_D$-3.1° (c 2.9, CHCl$_3$); EIMS m/z 800/802/804/806 (<1, M$^+$-C$_5$H$_8$O$_2$), 415/417/419/421 (5/3/3/2), 342/344/346 (7/9/4), 286/288/290 (2/6/2), 207 (34), 178 (22), 155/157 (66/24), 131 (36), 19 (70), 70 (100); HREIMS m/z 800.2179 (C$_{38}$H$_{48}$N$_2$O$_8$$^{35}$Cl$_4$, D-1.4 mmu); UV (MeOH) 1$_{max}$ (e) 204 (51200), 230 (18500), 248 (17200), 282 (2200) nm; IR (NaCl) n$_{max}$ 3376, 2965, 1755, 1728, 1712, 1678, 1504, 1258, 1150, 1067, 732 cm$^{-1}$. $^1$H NMR (CDCl$_3$) d unit A: 7.28–7.33 (10-H/14-H/11-H/13-H; m), 7.22 (12-H; m), 6.78 (3-H; ddd, 15.8/6.4/6.3), 6.40 (8-H; d, 15.8), 6.01 (7-H; dd, 15.8/8.7), 5.88 (2-H; d, 15.8), 5.06 (5-H; bm, W$_{1/2}$≈20 Hz), 262 (6-H; m), 2.53 (4-H$_2$; bm, W$_{1/2}$≈15 Hz), 1.12 (6-CH$_3$; d, 6.8); unit B 7.18 (5-H; d, 2.0), 7.05 (9H; dd, 8.5/2.0), 6.83 (8-H; d, 8.5), 6.49 (NH; d, 7.9), 5.06 (2-H; bm, W$_{1/2}$≈20 Hz), 4.79/4.70 (CH$_2$CCl$_3$; AB q, -11.7), 3.85 (OCH$_3$; s), 3.20 (3-H$_b$; dd, -14.1/5.8), 3.07 (3-H$_a$; dd, -14.1/6.7); unit C 5.38 (NH; bt, 6.5), 3.27 (3-H$_2$; d, 6.5), 1.20* (2-CH$_3$; s), 1.15*

(2-CH$_3$'; s); unit D 4.92 (2-H; dd, 10.0/3.8), 1.72 (4-H; bm, W$_{1/2}$≈20 Hz), 1.67 (3-H$_b$; ddd, −14.1/1.0/5.0/), 1.56 (3-H$_a$; ddd, −14.1/9.1/3.8), 1.43 (CO$_2$CMe$_3$; s), 0.86† (4-CH$_3$; d, 6.4), 0.82† (5-H$_3$; d, 6.4). $^{13}$C NMR (CDCl$_3$) d unit A 165.4 (1), 139.3 (3), 136.9 (9), 131.7 (8), 130.1 (7), 128.6 (11/13), 127.5 (12), 126.2 (10/14), 125.4 (2), 76.5 (5), 41.1 (6), 33.4 (4), 16.7 (6-Me); unit B 170.0 (1), 154.1 (7), 131.2 (5), 128.8 (4), 128.5 (9), 122.3 (6), 112.1 (8), 94.3 (CH$_2$CCl$_3$), 74.6 (CH$_2$CCl$_3$), 56.1 (7-OMe), 53.2 (2), 36.6 (3); unit C 176.9 (1), 156.4 (CO$_2$CMe$_3$), 79.1 (CO$_2$CMe$_3$), 48.7 (3), 44.0 (2), 22.8* (2-Me), 22.3* (2-Me'); unit D 170.7 (1), 71.4 (2), 39.5 (3), 28.4 (CO$_2$CMe$_3$), 24.8 (4), 23.0† (4-Me), 21.4† (5). (Resonances with identical superscripts are interchangeable)

Amino Acid R

To the amino acid Q (100 mg, 0.11 mmol) was added activated Zn dust (400 mg, excess) and AcOH (4 mL). The heterogeneous mixture was subject to sonication for 45 minutes, stirred for a further 90 minutes at room temperature, and then poured onto a pad of Celite. The organic material was washed from the Celite pad with CH$_2$Cl$_2$. The solvent was removed in vacuo, leaving the carboxylic acid as a colorless amorphous solid.

Without purification the crude acid was dissolved in trifluoroacetic acid (TFA, 5 mL) and allowed to sit at room temperature for 1 hour. After this time excess TFA was removed in vacuo and the resulting amorphous solid was then subjected to chromatographic purification (Sep-Pak™, silica, initially CH$_2$Cl$_2$ then 10% MeOH/CH$_2$Cl$_2$), yielding the trifluoroacetate ammonium salt of the desired compound. Repeated lyophilization of an aqueous solution of the salt resulted in the free amino acid R as a colorless amorphous solid (68 mg, 91% over two steps); IR (NaCl) n$_{max}$ 3300, 3200, 2965, 1693, 1606, 1504, 1441, 1259, 1201, 1146, 1066, 727 cm$^{-1}$. $^1$H NMR (CD$_3$OD) d unit A: 7.33 (10-H/14-H; d, 7.4), 7.28 (11-H/13-H; t, 7.4), 718–723 (12-H; m), 6.69 (3-H; ddd, 15.6/7.7/7.0), 6.43 (8-H; d, 15.8), 6.04 (7-H; dd, 15.8/8.9), 6.00 (2-H; d, 15.6), 5.01 (5-H; ddd, 9.1/6.9/3.1), 2.64 (4-H$_b$; bm, W$_{1/2}$≈30 Hz), 2.60 (6-H; bm, W$_{1/2}$≈20 Hz), 2.49 (4-H$_a$; ddd, 15.8/9.1/7.7), 1.13 (6-Me; d, 6.7); unit B 7.18–7.23 (5-H; m), 7.11 (9-H; dd, 8.3/1.6), 6.92 (8-H; d, 8.3), 4.59 (2-H; bm, W$_{1/2}$≈20 Hz), 3.81 (OCH$_3$; s), 3.14 (3-H$_b$; dd, −13.7/4.3), 2.96 (3-H$_a$; m, W$_{1/2}$≈20 Hz); unit C 2.96 (3-H$_2$; bm, W$_{1/2}$≈20 Hz), 1.31* (2-CH$_3$; s), 1.25* (2-CH$_3$'; s); unit D 4.90 (2-H; dd, 9.6/4.0), 1.66 (4-H; bm, W$_{1/2}$≈25 Hz), 1.59 (3-H$_b$; ddd, −14.4/9.6/4.8), 1.53 (3-H$_a$; ddd, −14.4/9.1/4.0), 0.81† (4-Me; d, 6.5), 0.74† (5-H$_3$; d, 6.5). $^{13}$C NMR (CD$_3$OD) d unit A 167.7 (1), 140.7 (3), 138.4 (9), 133.0 (8), 131.7 (7), 129.6 (11/13), 128.5 (12), 127.3 (10/14), 127.1 (2), 78.4 (5), 43.1 (6), 35.7 (4), 17.4 (6-Me); unit B 179.8 (1), 155.2 (7), 132.3 (4), 132.1 (5), 130.1 (9), 123.0 (6), 113.4 (8), 56.6 (7-OMe), 56.6 (2), 37.8 (3), unit C 176.8 (1), 48.2 (3), 42.2 (2), 23.3* (2-Me), 23.3* (2-Me'); unit D 172.0 (1), 73.4 (2), 40.7 (3), 26.0 (4), 23.1† (4-Me), 21.8† (5). (Resonances with identical superscripts are interchangeable)

Cryptophycin 51

To a stirred solution of amino acid T (75 mg, 0.11 mmol) in anhydrous DMF (20 mL) at room temperature under argon was added diisopropylethylamine (DIEA, 44 mg, 60 mL, 0.34 mmol, ≈3 equiv.) followed by pentafluorodiphenylphosphinate (FDPP, 55 mg, 0.14 mmol, ≈1.3 equiv.) in DMF (2 mL). The mixture was stirred for 12 hours, Et$_2$O (40 mL) was added; and the ether layer was washed successively with HCl (1M, 40 mL), brine (40 mL) and H$_2$O (40 mL), dried (MgSO$_4$) and evaporated under reduced pressure. The residual waxy solid was further purified by reversse phase chromatography (ODS, 10m, 30& H$_2$O/MeCN, 3 mL min$^{-1}$) to give Cryptophycin 51 as a colorless amorphous solid (45 mg, 61%), [a]$_D$+26.4° (c 0.25, CHCl$_3$); EIMS m/z 652/654 (M$^+$, 3/1), 632/634 (3/2), 426/428 (51/15), 227 (64), 195/197 (64/22), 155/157 (71/15), 131 (59), 91 (100); HREIMS m/z 652.2936 (C$_{36}$H$_{45}$N$_2$O$_7$$^{35}$Cl, D-2.1 mmu); UV (MeOH) 1$_{max}$ (e) 204 (52000), 228 (20400), 250 (13400), 284 (2800) nm; IR (NaCl) n$_{max}$ 3376, 3270, 2960, 1747, 1721, 1659, 1536, 1514, 1259, 1150, 1066, 1013, 980, 694 cm$^{-1}$. $^1$H NMR (CDCl$_3$) d unit A 7.32 (10-H/14-H; dd, 8.0/1.5), 7.29 (11-H/13-H; t, 8.0), 7.24 (12-H; bm, W$_{1/2}$≈15 Hz), 6.77 (3-H; ddd, 15.2/10.8/4.3), 6.40 (8-H; d, 15.8), 6.01 (7-H; dd, 15.8/8.8), 5.76 (2-H; dd, 15.2/1.1), 5.04 (5-H; ddd, 11.1/6.4/1.9), 2.54 (4-H$_b$/6-H; bm, W$_{1/2}$≈15 Hz), 2.37 (4-H$_a$; ddd, −14.3/11.1/10.8), 1.13 (6-Me; d, 6.8); unit B 7.20 (5-H; d, 2.0), 7.05 (9-H; dd, 8.4/2.0), 6.84 (8-H; d, 8.4), 5.61 (NH; d, 7.8), 4.74 (2-H; ddd, 7.8/7.6/5.4), 3.87 (OMe; s), 3.11 (3-H$_b$; dd, −14.2/5.4), 3.06 (3-H$_a$; dd, −14.2/7.6); unit C 7.24 (NH; bm, W$_{1/2}$≈15 Hz), 3.40 (3-H$_b$; dd, −13.5/8.5), 3.12 (3-H$_a$; dd, −13.5/3.6), 1.22* (2-Me; s), 1.15* (2-Me', s); unit D 4.85 (2-H; dd, 10.2/3.6), 1.66 (3-H$_b$; ddd, −14.0/10.2/4.6), 1.61 (4-H; bm W$_{1/2}$≈20.0 Hz), 1.33 (3-H$_a$; ddd, −14.0/9.0/3.6), 0.74† (4-Me; d, 6.6), 0.72† (5-H$_3$; d, 6.6). $^{13}$C NMR (CDCl$_3$) d unit A 165.1 (1), 142.2 (3), 136.7 (9), 131.7 (8), 130.1 (7), 128.6 (11/13), 127.5 (12), 126.1 (10/14), 124.6 (2), 77.0 (5), 42.2 (6), 36.5 (4), 17.3 (6-Me); unit B 170.3 (1), 154.1 (7), 130.9 (5), 129.5 (4), 128.3 (9), 122.5 (6), 112.3 (8), 56.1 (7-OMe), 54.2 (2), 35.3 (3); unit C 178.0 (1), 46.5 (3), 42.7 (2), 22.8* (2-Me), 22.6* (2-Me'); unit D 170.6 (1), 71.5 (2), 39.5 (3), 24.5 (4), 22.7† (4-Me), 21.2† (5). (Resonances with identical superscripts are interchangeable)

EXAMPLE 12

Synthesis of Cryptophycin 52 and Cryptophycin 53

To a stirred solution of Cryptophycin 51 (75 mg. 0.12 mmol) in anhydrous dichloromethane (7.5 mL) at 0° C. under argon was added a solution of m-chloroperbenzoic acid (mCPBA, 50 mg, 0.23 mmol, ≈2 equiv. based on 80% active oxygen) in dichloromethane (1 mL). After 30 minutes the reaction mixture was allowed to warm to room temperature and stirred for a further 12 hours. The solvent was then removed under reduced pressure to give a 1.8:1 mixture of cryptophycins 52 and 53 (by NMR analysis), respectively, as an amorphous solid. The mixture of regioisomeric epoxides was dissolved in minimal acetonitrile and subjected to reverse phase chromatography (YMC-ODS, 10 m, 250 mm×22.5 mm, 30% H$_2$O/MeCN, 6 mL min$^{-1}$) to separate Cryptophycin 52 (37 mg, 48%) and Cryptophycin 53 (19 mg, 25%).

Spectral data for Cryptophycin 52

[a]$_D$+19.9° (c 0.5, CHCl$_3$); EIMS m/z 668/670 (4/2, M$^+$), 445 (35), 244 (12), 227 (22), 195/197 (66/27), 184 (45), 155/157 (38/10), 91 (100); HREIMS m/z 668.2873 (C$_{36}$H$_{45}$N$_2$O$_8$$^{35}$Cl, D −0.9 mmu), 445.2497 (C$_{25}$H$_{35}$NO$_6$, D −3.3 mmu); UV (MeOH) 1$_{max}$ (e) 204 (35100), 218 (20900) nm; IR (NaCl) n$_{max}$ 3415, 3270, 2960, 1748, 1721, 1650, 1536, 1504, 1260, 1192, 1150, 1066, 1013, 800, 698 cm$^{-1}$. $^1$H NMR (CDCl$_3$) d unit A 7.33–7.38 (11-H/12-H/13-H; bm, W$_{1/2}$≈25 Hz), 7.24 (10-H/14-H; m, W$_{1/2}$≈15 Hz), 6.76 (3-H; ddd, 15.1/10.8/4.3), 5.71 (2-H; dd, 15.1/1.7), 5.20 (5-H; ddd, 11.0/5.0/1.8), 3.68 (8-H; d, 1.9), 2.92 (7-H; dd, 7.5/1.9), 2.57 (4-H$_b$; ddd, −14.6/1.8/1.7), 2.57 (4-H$_a$; ddd, −14.6/11.0/10.8), 1.78 (6-H; bm, W$_{1/2}$≈15 Hz), 1.14 (6-Me; d, 6.9); unit B 7.18 (5-H; d, 2.2), 7.04 (9-H; dd 8.4/2.2), 6.83 (8-H; d, 8.4), 5.56 (NH; d, 7.9), 4.73 (2-H; ddd, 7.9/7.4/5.3), 3.87 (OMe; s), 3.09 (3-H$_b$; dd, −14.6/5.3), 3.05 (3-H$_a$; dd, −14.67/7.4); unit C 7.20 (NH; dd, 8.6/3.2), 3.41 (3-H$_b$; dd, −13.4/8.6), 3.10 (3-H$_a$; dd, −13.4/3.2), 1.22* (2-Me; s), 1.15* (2-Me'; s); unit D 4.82 (2-H; dd, 10.2/3.5), 1.73 (3-H$_b$; bm, W$_{1/2}$≈20 Hz), 1.66 (4-H; bm, W$_{1/2}$≈20 Hz), 1.31 (3-H$_a$; ddd, −13.8/9.1/3.5), 0.84$^†$ (4-Me; d, 6.6), 0.82$^†$ (5-H$_3$; d, 6.6); $^{13}$C NMR (CDCl$_3$) d unit A 164.9 (1), 141.8 (3), 136.7 (9), 128.7 (11/13), 128.3 (12), 125.6 (10/14), 124.7 (2), 75.9 (5), 63.0 (7), 59.0 (8), 40.7 (6), 36.9 (4), 13.5 (6-Me), unit B 170.3 (1), 154.1 (7), 130.9 (5), 129.5 (4), 128.5 (9), 122.6 (6), 112.4 (8), 56.1 (7-OMe), 54.3 (2), 35.3 (3), unit C 178.0 (1), 46.5 (3), 42.8 (2), 22.8 (2-Me), 22.8 (2-Me'), unit D 170.5 (1), 71.2 (2), 39.3 (3), 24.6 (4), 22.7$^†$ (4-Me), 21.2$^†$ (5). (Resonances with identical superscripts are interchangeable)

Spectral data for Cryptophycin 53

[a]$_D$+20.8° (c 1.7, CHCl$_3$); EIMS m/z 668/670 (5/4, M$^+$), 445 (32), 244 (15), 227 (24), 195/197 (64/21), 184 (60), 155/157 (33/9), 91 (100); HREIMS m/z 668.2853 (C$_{36}$H$_{45}$N$_2$O$_8$$^{35}$Cl, D 1.1 mmu); UV (MeOH) 1$_{max}$ (e) 204 (38700), 218 (22900) nm; IR (NaCl) n$_{max}$ 3415, 3280, 2917, 2849, 1748, 1722, 1660, 1504, 1465, 1260, 1190, 1150, 1066, 755 cm$^{−1}$. $^1$H NMR (CDCl$_3$) d unit A 7.29–7.36 (11-H/12-H/13-H,), 7.23 (10-H/14-H; dd, 8.3/1.7), 6.77 (3-H; ddd, 15.1/10.9/4.3), 5.81 (2-H; dd, 15.1/1.3), 5.17 (5-H; ddd, 11.2/4.9/1.8), 3.58 (8-H; d, 1.7), 2.90 (7-H; dd, 7.8/1.7), 2.67 (4-H$_b$; ddd, 14.7/11.2/10.9), 2.56 (4-H$_a$; dddd, 14.7/4.3/1.8/1.3), 1.67–1.78 (6-H; bm, W$_{1/2}$≈45), 1.03 (6-CH$_3$; d, 7.1); unit B 7.21 (5-H; d, 2.1), 7.07 (9-H; dd, 8.5/2.1), 6.84 (8-H; d, 8.4), 5.90 (2-NH; d, 7.9), 4.75 (2-H; ddd, 7.9/7.9/4.9), 3.85 (7-OCH$_3$; s), 3.14 (3-H$_b$; dd, 14.5/4.9), 3.03 (3-H$_a$; dd, 14.5/7.9); unit C 7.29–7.36 (3-NH; bm, W$_{1/2}$≈25), 3.43 (3-H$_b$; dd, 13.7/8.8), 3.10 (3-H$_a$; dd, 13.7/3.4), 1.23* (2-CH$_3$; s), 1.17* (2-CH$_3$'; s); unit D 4.92 (2-H; dd, 10.3/3.2), 1.73 (3-H$_b$; bm, W$_{1/2}$≈45), 1.67–1.78 (4-H; bm, W$_{1/2}$≈45), 1.48 (3-H$_a$; ddd, 13.9/8.8/3.2), 0.89$^†$ (4-CH$_3$; d, 6.6), 0.86$^†$ ′(5-H$_3$; d, 6.6). $^{13}$C NMR (CDCl$_3$) d unit A 165.1 (1), 142.0 (3), 137.0 (9), 128.5 (11/13), 128.5 (12), 125.3 (10/14), 124.6 (2), 76.7 (5), 63.2 (7), 56.2 (8), 40.8 (6), 36.7 (4), 13.4 (6-Me); unit B: 170.4* (1), 154.0 (7), 130.8 (5), 129.7 (4), 128.2 (9), 122.5 (6), 112.3 (8), 56.1 (7-OMe), 54.4 (2), 35.3 (3); unit C 177.9 (1), 46.4 (3), 42.7 (2), 23.0° (2-Me), 22.7° (2-Me'); unit D 170.5° (1), 71.3 (2), 39.2 (3), 24.7 (4), 22.8$^†$ (4-Me), 21.3$^†$ (5). (Resonances with identical superscripts are interchangeable)

EXAMPLE 13

Synthesis of Cryptophycin 55

To a solution of Cryptophycin 52 (6 mg, 0.009 mmol) in 0.6 mL of 2:1 1,2-dimethoxyethane/water was added 2 μL of 12 N HCl. The solution was allowed to stir at room temperature for 20 h, neutralized with potassium carbonate, filtered through a 5 mm filter, and evaporated. The acetonitrile-soluble material was purified by reversed-phase HPLC on C18 (250×10 mm column) using 4:1 MeOH/H$_2$O to obtain 3.0 mg of Cryptophycin 55 (48%). $^1$H NMR (CDCl$_3$) d unit A 7.35–7.42 (10-H/11-H/12-H/13-H/14-H; m), 6.78 (3-H; ddd, 15.1/10.6/4.5), 5.78 (2-H; dd, 15.1/1.7), 5.16 (6-H; ddd, 11.1/8.3/2.1), 4.65 (8-H; d, 9.7), 4.01 (7-H; bd, 9.7), 2.69 (4-H; dddd, −14.5/4.5/2.1/1.7), 2.50 (6-H; bm, W$_{1/2}$≈15), 2.38 (4-H$_a$; ddd, −14.5/11.1/10.6), 1.53 (7-OH; s), 1.04 (6-Me, d, 7.1)l unit B 7.21 (5-H; d, 2.2), 7.07 (9-H; dd, 8.5/2.2), 6.85 (8-H; d, 8.5), 5.57 (2-NH; d, 7.8), 4.74 (2-H; ddd, 7.8/7.6/5.2), 3.88 (7-OCH$_3$; s), 3.13 (3-H$_b$; dd, 14.5/5.2), 3.05 (3-H$_a$; dd, 14.5/7.6); unit C 7.21 (3-NH; m), 3.38 (3-H$_b$; dd, 13.5/8.3), 3.17 (3-H$_a$; dd, 13.5/4.1), 1.23* (2-CH$_3$; s), 1.17* (2-CH$_3$'; s), unit D 4.93 (2-H; dd, 10.1/3.5), 1.78 (3-H$_b$; ddd, 13.5/10.1/5.0), 1.72 (4-H; bm, W$_{1/2}$≈20), 1.43 (3-H$_3$; ddd, 13.5/8.8/3.5), 0.92$^†$ (4-CH$_3$; d, 6.6), 0.92$^†$ (5-H$_3$, d, 6.4). $^{13}$C NMR (CDCl$_3$) d unit A 165.1 (C-1), 142.4 (C-3), 138.4 (C-9), 129.0 (C-11/13), 128.3 (C-12), 128.0 (C-10/14), 124.6 (C-2), 76.1 (C-5), 74.1 (C-7), 62.0 (C-8), 38.4 (C-6), 36.5 (C-4), 8.6 (6-Me); unit B 170.3 (C-1), 154.1 (C-7), 130.9 (C-5), 129.6 (C-4), 129.2 (C-9), 122.6 (C-6), 112.3 (C-8), 56.1 (7-OMe), 54.3 (C-2), 35.3 (C-3)l unit C 177.8 (C-1), 46.5 (C-3), 42.8 (C-2), 22.9 (2-Me), 23.0 (C-2-Me'); unit D 170.3 (C-1), 71.3 (C-2), 39.7 (C-3), 24.8 (C-4), 22.7$^†$ (4-Me), 21.6$^†$ (C-5). (Resonances with identical superscripts are interchangeable). The corresponding diol, Cryptophycin 56 (2.8 mg, 44% yield), was also obtained.

EXAMPLE 14

Synthesis of Cryptophycin 57

A catalytic amount of PtO$_2$ was added to a flask containing 0.5 ml of CH$_2$Cl$_2$. The air in the flask was evacuated, H$_2$ was introduced, and the mixture was stirred at room temperature for 20 min. A solution of 10 mg of Cryptophycin 52 in minimal CH$_2$Cl$_2$ was added and the mixture was stirred at room temperature for 45 min. The catalyst was removed by filtration through celite/cotton and the solvent was evaporated. Reversed phase HPLC of the residue on a C18 column yielded pure Cryptophycin 57. $^1$H NMR (CDCl$_3$) d unit A 2.32 (2, ddd; −14.5, 9.2, 5.8), 2.10 (2, ddd; −14.5, 9.2, 6.2), 1.5–1.8 (¾ overlapping m), 5.07 (5, ddd; 12.5, 5.6, 2.0), 1.80 (6, m), 1.12 (6-Me, d; 7.0), 2.90 (7, dd; 7.4, 1.8), 3.67 (8, d; 1.8), 7.24 (10/14, m), 7.32–7.38 (11/12/13, m); unit B 4.71 (2, ddd; 8.7, 6.4, 6.3), 5.62 (2-NH, d; 8.7), 3.08 (2H-3, br d; 6.4), 7.19 (5, d; 2.0), 3.87 (7-OMe, s), 6.83 (8, d; 8.5), 7.07 (9, dd; 8.4, 2.0); unit C 7.20 (NH; dd, 8.6/3.2), 3.41 (3-H$_b$; dd, −13.4/8.6), 3.10 (3-H$_a$; dd, −13.4/3.2), 1.22* (2-Me; s), 1.15* (2-Me'; s); unit D 4.83 (2, dd; 9.9, 3.8), 1.39 (3, m), 1.70 (3, m), 1.72 (4, m), 0.87 (4-Me, d; 5.3), 0.86 (5, d; 5.3).

EXAMPLE 15

Synthesis of Cryptophycin 58

To a solution of Cryptophycin 57 (6 mg, 0.009 mmol) in 0.6 mL of 2:1 1,2-dimethoxyethane/water was added 2 μL 12 N HCl. The solution was allowed to stir at room temperature for 4 h, neutralized with potassium carbonate, and evaporated. The residue was partitioned between water and CH$_2$Cl$_2$. The CH$_2$Cl$_2$-soluble material was purified by reverse-phase HPLC on C18 using 4:1 MeOH/H$_2$O to obtain pure Cryptophycin 58. $^1$H NMR (CDCl$_3$) d unit A 2.32 (2, ddd; −14.5, 9.2, 5.8), 2.10 (2, ddd; −14.5, 9.2, 6.2), 1.5–1.8 (¾ overlapping m), 5.07 (5, ddd; 12.5, 5.6, 2.0), 1.80 (6, m), 1.12 (6-Me, d; 7.0), 2.90 (7, dd; 7.4, 1.8), 3.67 (8, d; 1.8), 7.24 (10/14, m), 7.32–7.38 (11/12/13, m); unit B 4.82 (2-H; ddd, 8.8/7.2/5.6), 5.64 (2-NH; d, 8.8), 3.03 (3-H; dd, −15.4/7.2), 3.16 (3-H; dd; −15.4/5.6), 7.23 (5-H; d, 2.2), 3.88 (7-OCH$_3$; s), 6.85 (8-H; d, 8.5), 7.09 (9-H; dd, 8.5/2.2); unit C 7.20 (NH; dd, 8.6/3.2), 3.41 (3-H$_b$; dd, −13.4/8.6), 3.10 (3-H$_a$; dd, −13.4/3.2), 1.22* (2-Me; s), 1.15* (2-Me'; s); unit D 4.92 (2-H; dd, 10.1/3.5), 1.76 (3-H/4-H; m), 1.45 (3-H; m), 0.94 (5-H$_3$; d, 6.6), 0.94 (4-Me; d, 6.4).

EXAMPLE 16

Synthesis of Cryptophycin 61

To a solution of Cryptophycin 53 (5 mg, 0.007 mmol) in 0.5 mL of dry benzene was added triphenylphosphine sulfide (4 mg, 0.014 mmol) followed by 0.65 μL of trifluoroacetic acid as a solution in dry benzene (100 μl). The solution was allowed to stir at room temperature for 6 h, neutralized with sodium bicarbonate, filtered and evaporated. The residue was partitioned between water and $CH_2Cl_2$. The $CH_2Cl_2$-soluble material was purified by reversed-phase HPLC on C18 using 4:1 MeCN/$H_2O$ to obtain pure Cryptophycin 61 (1.9 mg, 37%). $^1H$ NMR (300 MHz, $CDCl_3$) unit A 7.24–7.35 (10/11/12/13/14-H; m), 6.73 (3-H; ddd, 15.0/10.2/4.8), 5.67 (2-H; d, 15.0), 5.23 (5-H; bm, $W_{1/2}$≈15 Hz), 3.68 (8-H; d, 5.1), 3.01 (7-H; dd, 8.3/5.1), 2.52 (4-$H_b$; bm, $W_{1/2}$≈15 Hz), 2.41 (4-$H_a$; ddd, −14.6/11.1/10.8), 1.6–1.8 (6-H; m), 1.15 (6-Me; d, 6.9); unit B 7.18 (5-H; d, 2.1), 7.04 (9-H; dd, 8.4/2.1), 6.84 (8-H; d, 8.4), 5.45 (NH; d, 7.8), 4.75 (2-H; ddd, 7.8/7.2/6.9), 3.88 (OMe; s), 3.08 (3-$H_b$/3-$H_a$; bm, $W_{1/2}$≈15 Hz); unit C 7.17 (NH; m), 3.40 (3-$H_b$; dd, −13.6/8.4), 3.13 (3-$H_a$; dd, −13.6/3.6), 1.23* (2-Me; s), 1.16* (2-Me'; s); unit D 4.86 (2-H; dd, 9.9/3.6), 1.6–1.8 (3-$H_b$/4-H, m), 1.43 (3-$H_a$; bm, $W_{1/2}$≈15 Hz), 0.92† (4-Me; d, 6.6), 0.88† (5-$H_3$; d, 6.6).

All publications and patent applications cited in this specification, but not individually and specifically incorporated by reference, are herein incorporated by reference as if they had been specifically and individually indicated to be incorporated by reference.

Although the foregoing invention has been described in some detail by way of illustration and example for purposes of clarity and understanding, it will be apparent to those of ordinary skill in the art in light of the teaching of this invention that certain changes and modifications may be made thereto without departing from the spirit or scope of the claims.

EXAMPLE 17

Structure-Activity Relationships (SAR)

Cryptophycin 51 and Cryptophycin 3 show comparable cytotoxicities against human tumor cell lines such as KB and LoVo ($IC_{50}$'s 2–4 ng/mL). Furthermore Cryptophycin 52 ($IC_{50}$'s 25–50 pg/mL) and Cryptophycin 1 ($IC_{50}$'s 5–20 ng/mL) show comparable cytotoxicities ($IC_{50}$'s 15–45 pg/mL. In mice the acute and chronic toxicities of Cryptophycin 52 are greater than Cryptophycin 1; however, antitumor activity is seen at sublethal levels.

Cryptophycin 52 shows comparable in vivo activity to Cryptophycin 1. Cryptophycin 52 is active against pancreatic ductal adenocarcinoma #03, at 8.1 mg/kg, showing a tumor burden T/C (mean tumor burden in treated animals/mean tumor burden untreated animals) of 16% and a gross (tumor cell) log kill <2. Cryptophycin 52 is active against early stage colon adenocarcinoma #33, at 8.1 mg/kg, showing a tumor burden T/C of 4% and a gross (tumor cell) log kill <2.

T/C values that are less than 42% are considered to be active by NCI standards; T/C values that are less than 10% are considered to have excellent activity and potential clinical activity by NCI standards. Gross log kill is defined as T-C/3.2 Td where T is the median time in days for the tumors of the treated group to reach 750 mg, C is the median time in days for the tumors of the control group to reach 750 mg, and Td is the tumor volume doubling time (T. H. Corbett et al., Cytotoxic Anticancer Drugs: Models and Concepts for Drug Discovery and Development, pp 35–87; Kluwer: Norwell, 1992). Gross log kill values of >2.8, 2.0–2.8, 1.3–1.9, 0.7–1.2, and <0.7 with duration of drug treatment of 5–20 days are scored ++++, +++, ++, + and − (inactive), respectively. An activity range of +++ to ++++, which is indicative of clinical activity, is needed to effect partial or complete regression of 100–300 mg size masses of most transplanted solid tumors or mice. Cryptophycin 1 shows T/C values ranging from 0 to 27% and log kill values ranging from <1 to 2. Cryptophycin 8 shows T/C values ranging from 0 to 18% and log kill values ranging from 1.8 to >4.6 (cures).

REFERENCES

1. Eglof, G., Organic Chemistry: An Advanced Treatise, Gilmar et al. (ed.), pp. 31–46, John Wiley & Sons (1943).
2. Kemp, et al., Organic Chemistry, Worth Publishers, Inc. (1980).
3. Patterson, G. M. L. et al. J. Phycol. 27:530–6 (1991).
4. Corbett, T. H. et al. Cytotoxic Anticancer Drugs: Models and Concepts for Drug Discovery and Development, pp 35–87; Kluwer Academic Publishers: Norwell, 1992.
5. Valeriote, F. A. et al. Discovery and Development of Anticancer Agents; Kluwer Academic Publishers: Norwell, 1993; in press.
6. Schwartz, R. E. et al. J. Ind. Microbiol. 5:113–24 (1990).
7. Hirsch, C. F. et al. U.S. Pat. No. 4,946,835, issued Aug. 7, 1990.
8. Sesin, D. F. U.S. Pat. No. 4,845,085, issued Jul. 4, 1989.
9. Sesin, D. F.; Liesch, J. M. U.S. Pat. No. 4,868,208, issued Sep. 19, 1989.
10. Sesin, D. F. U.S. Pat. No. 4,845,086, issued Jul. 4, 1989.
11. Skehan, P. et al., J. Natl. Cancer Inst. 82:1107–1112 (1990).
12. Bradley, G. et al. Cancer Res. 49:2790–2796 (1989).
13. Endicott, J. A. et al. Ann. Rev. Biochem. 58:137–171 (1989).
14. Beck, W. T. Biochem. Pharm. 36:2879–2887 (1987).
15. Moscow, J. A. et al. J. Natl. Cancer Inst. 80:14–20 (1988).
16. Trimurtulu, G. et al., "Total structures of cryptophycins, potent antitumor depsipeptides from the blue-green alga Nostoc sp. strain GSV 224", J. Am. Chem. Soc. 116:4729–4737 (1994).
17. Smith, C. D. et al., "Cryptophycin: a new microtubule depolymerizing agent active against drug resistant cells", Cancer Research 54:3779–3784 (1984).

What is claimed is:

1. A cryptophycin represented by the structure:

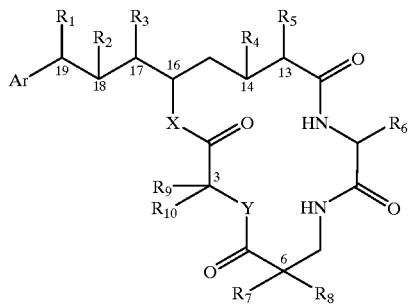

wherein:

Ar is phenyl or any unsubstituted or substituted aromatic or heteroaromatic group;

$R_1$ is a halogen, SH, amino, monoalkylamino, dialkylamino, trialkylammonium, alkythio, dialkysulfonium, sulfate, or phosphate;

$R_2$ is OH or SH; or $R_1$ and $R_2$ may be taken together to form an epoxide ring, an aziridene ring, an episulfide ring, a sulfate ring or a monoalkylphosphate ring; or $R_1$ and $R_2$ may be taken together to form a second bond between $C_{18}$ and $C_{19}$;

$R_3$ is a lower alkyl group;

$R_4$ is H;

$R_5$ is H;

$R_4$ and $R_5$ may be taken together to form a second bond between $C_{13}$ and $C_{14}$;

$R_6$ is a benzyl, hydroxybenzyl, alkoxybenzyl, halohydroxybenzyl, dihalohydroxybenzyl, haloalkoxybenzyl, or dihalohydroxybenzyl group;

$R_7$ is H or a lower alkyl group;

$R_8$ is H or a lower alkyl group;

$R_9$ is H or a lower alkyl group;

$R_{10}$ is H or a lower alkyl group;

X is O, NH or alkylamino; and

Y is O, NH or alkylamino wherein the following structures are excluded:

(1)

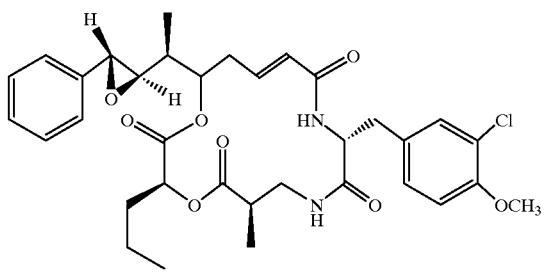

(2)

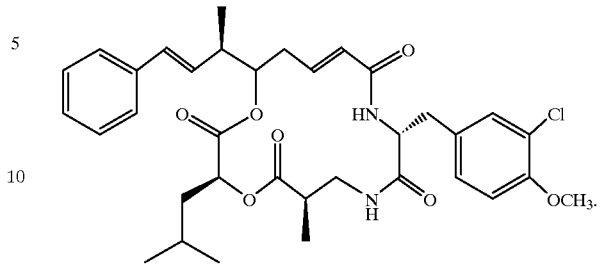

2. The cryptophycin of claim 1, wherein $R_8$ is ethyl, propyl, isopropyl, butyl, isobutyl, pentyl or isopentyl.

3. The cryptophycin of claim 1, wherein $R_7$ is ethyl, propyl, isopropyl, butyl, isobutyl, pentyl or isopentyl.

4. The cryptophycin of claim 1, wherein $R_7$ is H, $R_8$ is methyl, $R_3$ is methyl; X and Y are not both O.

5. The cryptophycin of claim 1, wherein $R_3$ is ethyl, propyl, isopropyl, butyl, isobutyl, pentyl or isopentyl.

6. The cryptophycin of claim 1, wherein $R_9$ is methyl, ethyl, propyl, isopropyl, butyl, isobutyl, pentyl or isopentyl.

7. The cryptophycin of claim 1, wherein $R_{10}$ is methyl, ethyl, propyl, isopropyl, butyl, isobutyl, pentyl or isopentyl.

8. The compound of claim 1, wherein at least one of the groups attached to $C_3$, $C_6$, $C_{10}$, $C_{16}$, $C_{17}$ and $C_{18}$ have R stereochemistry.

9. The compound of claim 1, wherein at least one of the groups attached to $C_3$, $C_6$, $C_{10}$, $C_{16}$, $C_{17}$ and $C_{18}$ have S stereochemistry.

10. The compound of claim 1, wherein $R_1$ and $R_2$ are taken together to form a second bond between $C_{18}$ and $C_{19}$, $R_3$, $R_7$ and $R_8$ are methyl, $R_4$ and $R_5$ are taken together to form a second bond between $C_{13}$ and $C_{14}$ such that there is a double bond, $R_6$ is 3-chloro-4-methoxybenzyl, $R_9$ is isobutyl, $R_{10}$ is hydrogen, and X and Y are oxygen.

11. The compound of claim 1, wherein $R_1$ and $R_2$ are taken together to form a R,R-epoxide ring, $R_3$, $R_7$ and $R_8$ are methyl, $R_4$ and $R_5$ are taken together to form a second bond between $C_{13}$ and $C_{14}$ such that there is a double bond, $R_6$ is 3-chloro-4-methoxybenzyl, $R_9$ is isobutyl, $R_{10}$ is hydrogen, and X and Y are oxygen.

12. The compound of claim 1, wherein $R_1$ and $R_2$ are taken together to form a S,S-epoxide ring, $R_3$, $R_7$ and $R_8$ are methyl, $R_4$ and $R_5$ are taken together to form a second bond between $C_{13}$ and $C_{14}$ such that there is a double bond, $R_6$ is 3-chloro-4-methoxybenzyl, $R_9$ is isobutyl, $R_{10}$ is hydrogen, and X and Y are oxygen.

13. The compound of claim 1, wherein $R_1$ is chloro, $R_2$ is hydroxyl, $R_3$, $R_7$ and $R_8$ are methyl, $R_4$ and $R_5$ are taken together to form a second bond between $C_{13}$ and $C_{14}$ such that there is a double bond, $R_6$ is 3-chloro-4-methoxybenzyl, $R_9$ is isobutyl, $R_{10}$ is hydrogen, and X and Y are oxygen.

14. The compound of claim 1, wherein $R_1$ and $R_2$ are taken together to form an epoxide ring, $R_3$, $R_7$ and $R_8$ are methyl, $R_4$ and $R_5$ are hydrogen, $R_6$ is 3-chloro-4-methoxybenzyl, $R_9$ is isobutyl, $R_{10}$ is hydrogen, and X and Y are oxygen.

15. The compound of claim 1, wherein $R_1$ is chloro, $R_2$ is hydroxyl, $R_3$, $R_7$ and $R_8$ are methyl, $R_4$ and $R_5$ are hydrogen, $R_6$ is 3-chloro-4-methoxybenzyl, $R_9$ is isobutyl, $R_{10}$ is hydrogen, and X and Y are oxygen.

16. The compound of claim 1, wherein $R_1$ and $R_2$ are taken together to form a R,R-episulfide ring, $R_3$, $R_7$ and $R_8$ are methyl, $R_4$ and $R_5$ are taken together to form a second bond between $C_{13}$ and $C_{14}$ such that there is a double bond, $R_6$ is 3-chloro-4-methoxybenzyl, $R_9$ is isobutyl, $R_{10}$ is hydrogen, and X and Y are oxygen.

17. A pharmaceutical composition for inhibiting proliferation of a hyperproliferative mammalian cell comprising an effective amount of a compound with the following structure:

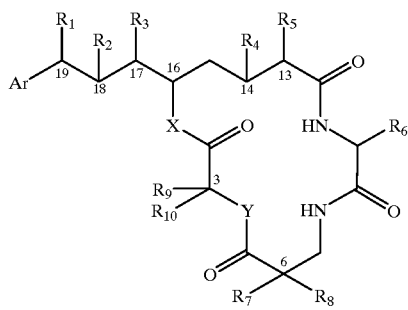

wherein:

Ar is phenyl or any unsubstituted or substituted aromatic or heteroaromatic group;

$R_1$ is a halogen, SH, amino, monoalkylamino, dialkylamino, trialkylammonium, alkythio, dialkysulfonium, sulfate, or phosphate;

$R_2$ is OH or SH; or $R_1$ and $R_2$ may be taken together to form an epoxide ring, an aziridene ring, an episulfide ring, a sulfate ring or a monoalkylphosphate ring; or $R_1$ and $R_2$ may be taken together to form a second bond between $C_{18}$ and $C_{19}$;

$R_3$ is a lower alkyl group;

$R_4$ is H;

$R_5$ is H;

$R_4$ and $R_5$ may be taken together to form a second bond between $C_{13}$ and $C_{14}$;

$R_6$ is a benzyl, hydroxybenzyl, alkoxybenzyl, halohydroxybenzyl, dihalohydroxybenzyl, haloalkoxybenzyl, or dihalohydroxybenzyl group;

$R_7$ is H or a lower alkyl group;

$R_8$ is H or a lower alkyl group;

$R_9$ is H or a lower alkyl group;

$R_{10}$ is H or a lower alkyl group;

X is O, NH or alkylamino; and

Y is O, NH or alkylamino wherein the following structures are excluded:

(1)

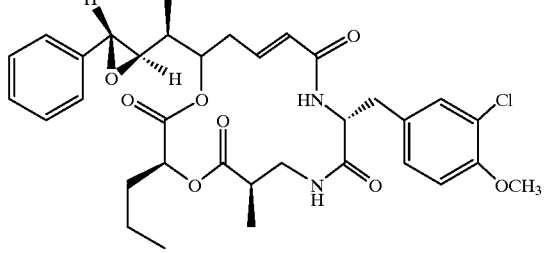

(2)

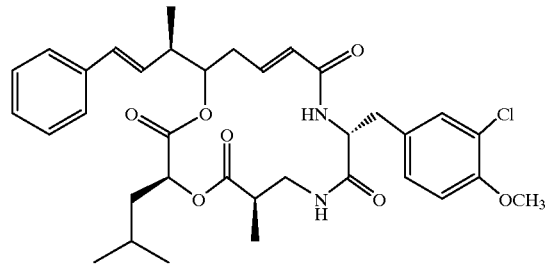

together with a pharmaceutically acceptable carrier.

18. The pharmaceutical composition of claim 17 further comprising at least one anti-mitotic antitumor agent in addition to said compound.

19. A method for inhibiting proliferation of a mammalian cell comprising contacting the mammalian cell with a cryptophycin compound in an amount sufficient to inhibit the proliferation of the cell, the cryptophycin compound having the following structure:

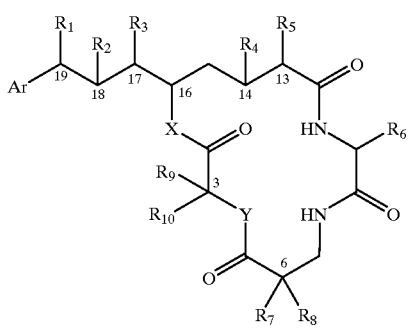

wherein:

Ar is phenyl or any simple unsubstituted or substituted aromatic or heteroaromatic group; $R_1$ is a halogen, SH, amino, monoalkylamino, dialkylamino, trialkylammonium, alkythio, dialkysulfonium, sulfate, or phosphate;

$R_2$ is OH or SH; or $R_1$ and $R_2$ may be taken together to form an epoxide ring, an aziridene ring, an episulfide ring, a sulfate ring or a monoalkylphosphate ring; or $R_1$ and $R_2$ may be taken together to form a second bond between $C_{18}$ and $C_{19}$;

$R_3$ is a lower alkyl group;

$R_4$ is H;

$R_5$ is H;

$R_4$ and $R_5$ may be taken together to form a second bond between $C_{13}$ and $C_{14}$;

$R_6$ is a benzyl, hydroxybenzyl, alkoxybenzyl, halohydroxybenzyl, dihalohydroxybenzyl, haloalkoxybenzyl, or dihalohydroxybenzyl group;

$R_7$ is H or a lower alkyl group;

$R_8$ is H or a lower alkyl group;

$R_9$ is H or a lower alkyl group;

$R_{10}$ is H or a lower alkyl group;

X is O, NH or alkylamino; and

Y is O, NH or alkylamino.

20. The method of claim 19 further comprising contacting the cell with at least one anti-mitotic antitumor agent in addition to said compound.

21. The method of claim 20, wherein said anti-mitotic antitumor agent is selected from agents which inhibit formation of microtubules by sequestering tubulin, agents with induce formation of paracrystalline aggregates of tubulin or agents which promote the polymerization of tubulin.

22. The method of claim 20, wherein said anti-mitotic antitumor agent is selected from colchicine, colcemid, vinblastine, vincristine or taxol.

23. The method of claim 19, wherein the mammalian cell is hyperproliferative.

24. The method of claim 23, wherein the hyperproliferative cell is human.

25. A method for inhibiting proliferation of a hyperproliferative mammalian having a multiple drug resistant phenotype comprising contacting the cell with an amount of a cryptophycin compound effective to disrupt the dynamic state of microtubule polymerization and depolymerization to arrest cell mitosis, thereby inhibiting the proliferation of the cell, the cryptophycin compound having the following structure:

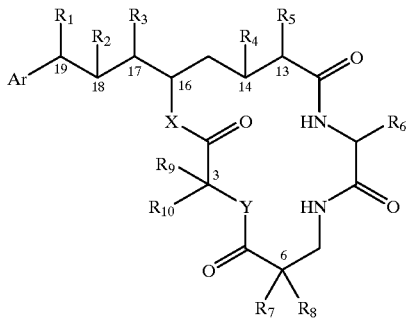

wherein:

Ar is phenyl or any simple unsubstituted or substituted aromatic or heteroaromatic group;

$R_1$ is a halogen, SH, amino, monoalkylamino, dialkylamino, trialkylammonium, alkythio, dialkysulfonium, sulfate, or phosphate;

$R_2$ is OH or SH; or $R_1$ and $R_2$ may be taken together to form an epoxide ring, an aziridene ring, an episulfide ring, a sulfate ring or a monoalkylphosphate ring; or $R_1$ and $R_2$ may be taken together to form a second bond between $C_{18}$ and $C_{19}$;

$R_3$ is a lower alkyl group;

$R_4$ is H;

$R_5$ is H;

$R_4$ and $R_5$ may be taken together to form a second bond between $C_{13}$ and $C_{14}$;

$R_6$ is a benzyl, hydroxybenzyl, alkoxybenzyl, halohydroxybenzyl, dihalohydroxybenzyl, haloalkoxybenzyl, or dihalohydroxybenzyl group;

$R_7$ is H or a lower alkyl group;

$R_8$ is H or a lower alkyl group;

$R_9$ is H or a lower alkyl group;

$R_{10}$ is H or a lower alkyl group;

X is O, NH or alkylamino; and

Y is O, NH or alkylamino.

* * * * *